(12) United States Patent
Kumamaru et al.

(10) Patent No.: US 11,773,369 B2
(45) Date of Patent: Oct. 3, 2023

(54) GENERATION OF HUMAN SPINAL CORD NEURAL STEM CELLS

(71) Applicant: THE REGENTS OF THE UNIVERSITY OF CALIFORNIA, Oakland, CA (US)

(72) Inventors: Hiromi Kumamaru, La Jolla, CA (US); Mark Tuszynski, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 970 days.

(21) Appl. No.: 16/530,777

(22) Filed: Aug. 2, 2019

(65) Prior Publication Data

US 2020/0087623 A1    Mar. 19, 2020

Related U.S. Application Data

(60) Provisional application No. 62/714,590, filed on Aug. 3, 2018.

(51) Int. Cl.
    *C12N 5/0797*    (2010.01)

(52) U.S. Cl.
    CPC ...... *C12N 5/0623* (2013.01); *C12N 2501/115* (2013.01); *C12N 2501/119* (2013.01); *C12N 2501/999* (2013.01); *C12N 2506/02* (2013.01); *C12N 2506/45* (2013.01)

(58) Field of Classification Search
    CPC .................................................. C12N 5/0623
    See application file for complete search history.

(56) References Cited

U.S. PATENT DOCUMENTS

2013/0183674 A1* 7/2013 Studer ............... G01N 33/5058
                                                                  435/7.1

OTHER PUBLICATIONS

Corral et al. (2017, Frontiers in Cell and Devl. Biol., vol. 5(58), pp. 1-18). (Year: 2017).*

* cited by examiner

*Primary Examiner* — Anoop K Singh
*Assistant Examiner* — David A Montanari
(74) *Attorney, Agent, or Firm* — K&L Gates LLP; Louis C. Cullman; Michelle Glasky Bergman

(57) ABSTRACT

Spinal cord neural stem cells (NSCs) have great potential to reconstitute damaged spinal neural circuitry. In some embodiments, derivation of spinal cord NSCs from human pluripotent stem cells (hPSCs) is described. These spinal cord NSCs can differentiate into a diverse population of spinal cord neurons comprising multiple positions in the dorso-ventral axis, and can be maintained for prolonged time periods. After grafting into injured spinal cords, grafts may be rich with excitatory neurons, extend large numbers of axons over long distances, innervate their target structures, and enable robust corticospinal regeneration. In some embodiments, hPSC-derived spinal cord NSCs enable a broad range of biomedical applications for in vitro disease modeling, and can provide a clinically-translatable cell source for spinal cord "replacement" strategies in several spinal cord disorders.

8 Claims, 44 Drawing Sheets

Figure 2A:
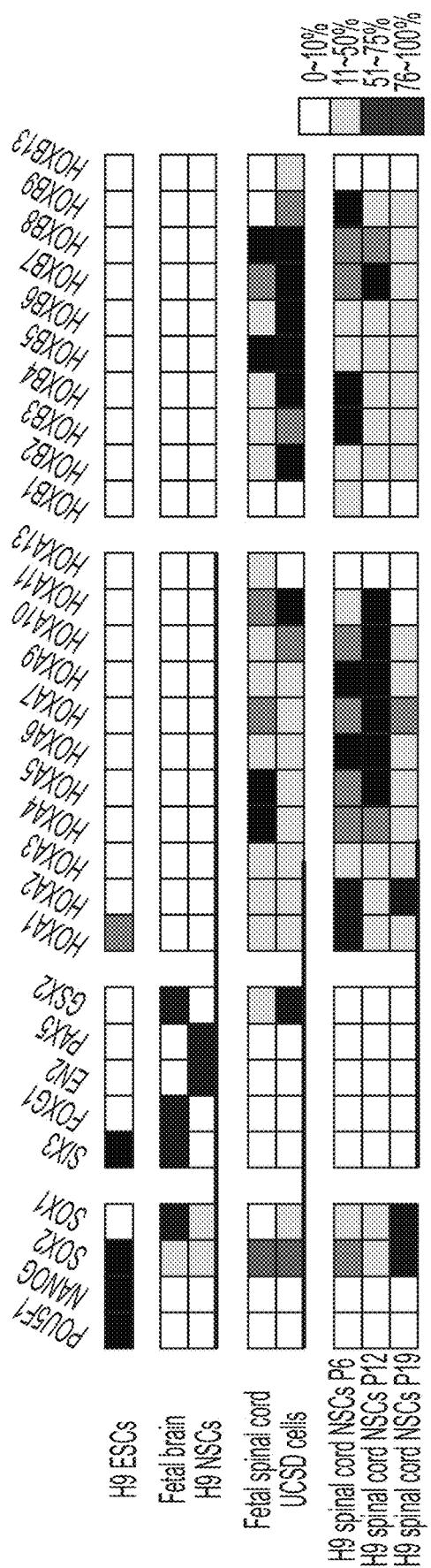

Specification includes a Sequence Listing.

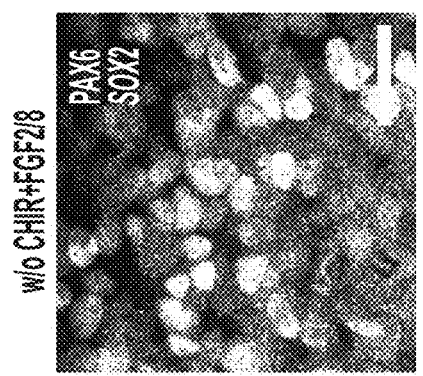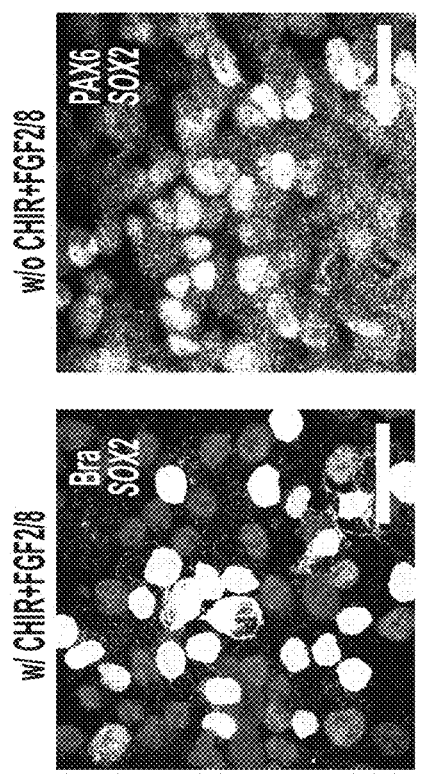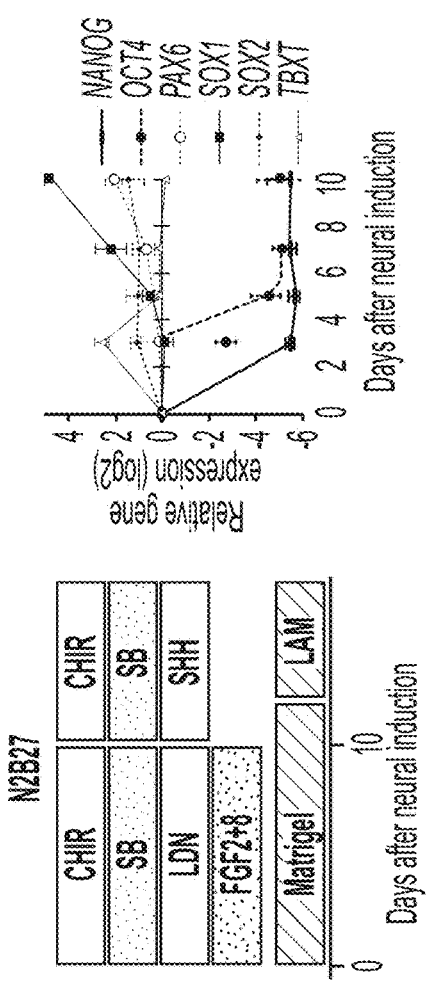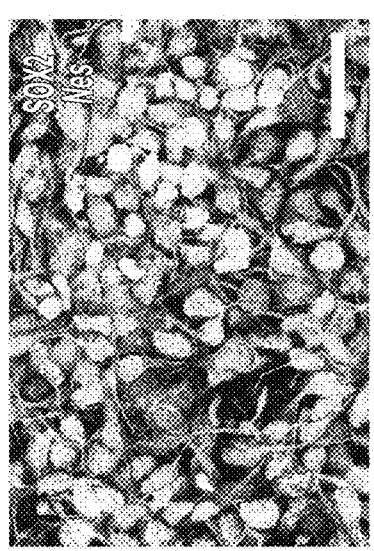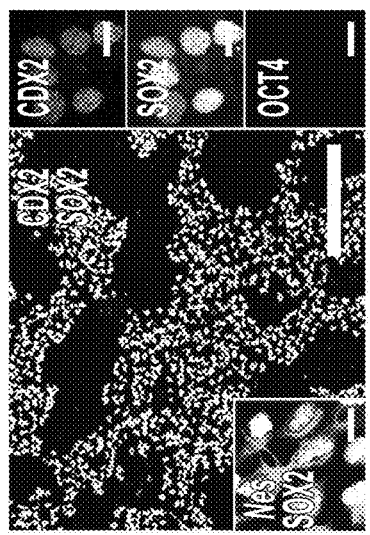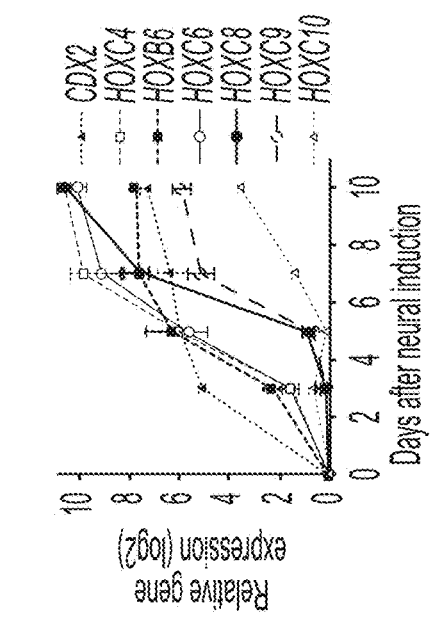

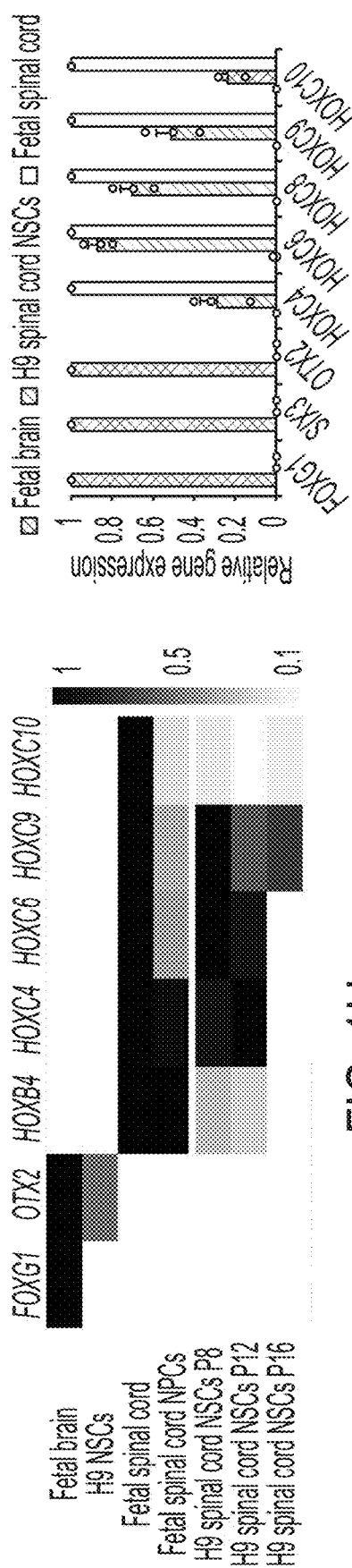
FIG. 1H
FIG. 1I
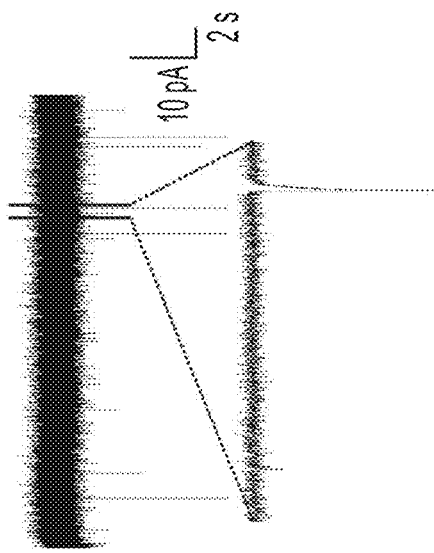
FIG. 1K
FIG. 1L
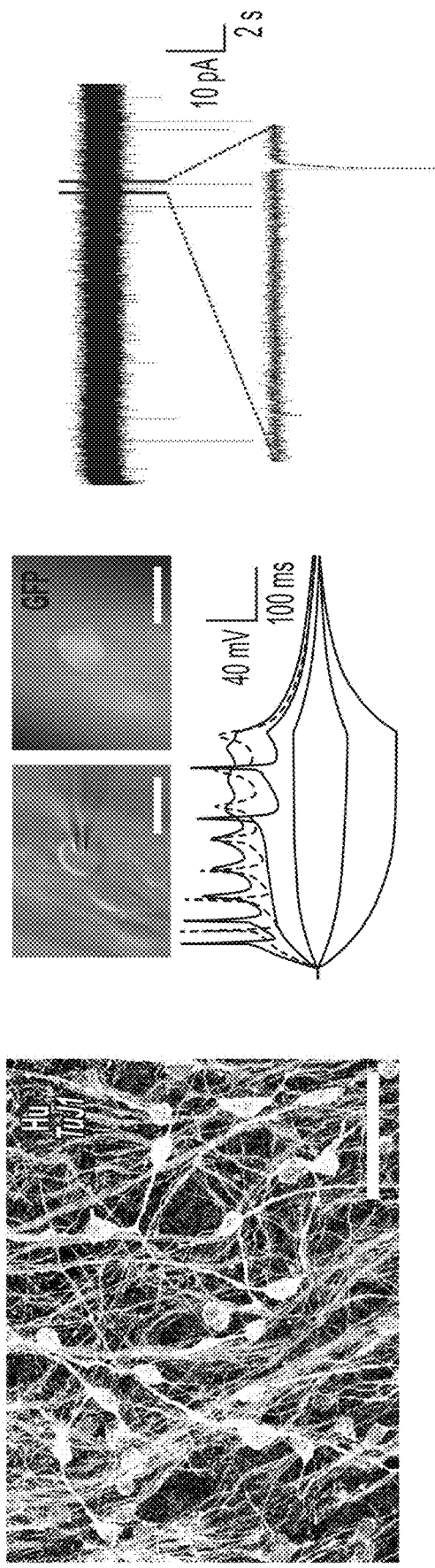
FIG. 1J

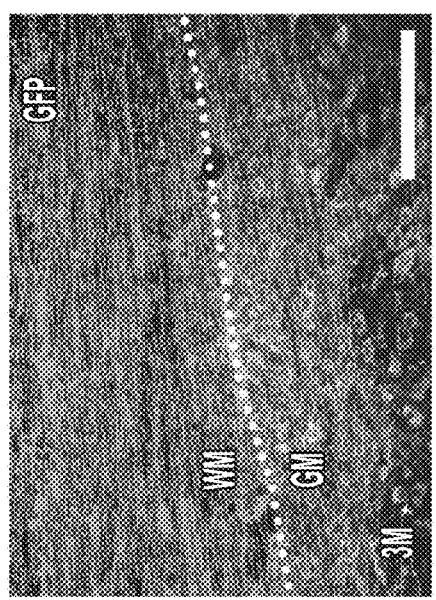
FIG. 3A
FIG. 3B
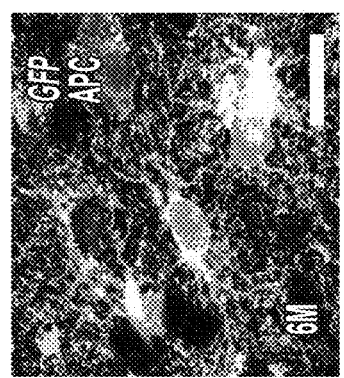
FIG. 3G
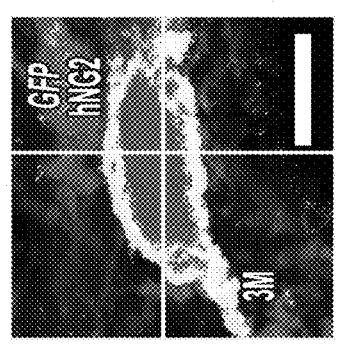
FIG. 3F
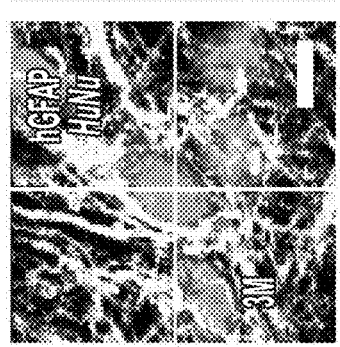
FIG. 3E
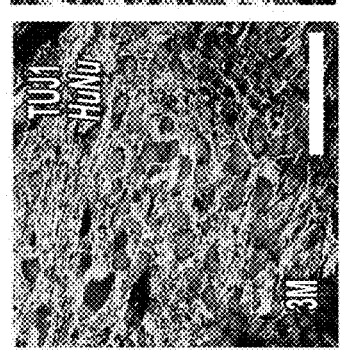
FIG. 3D
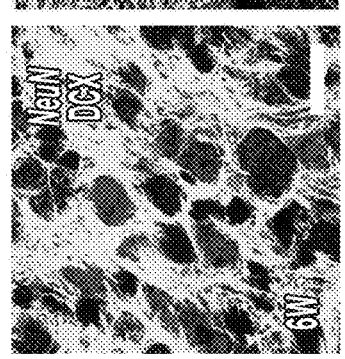
FIG. 3C

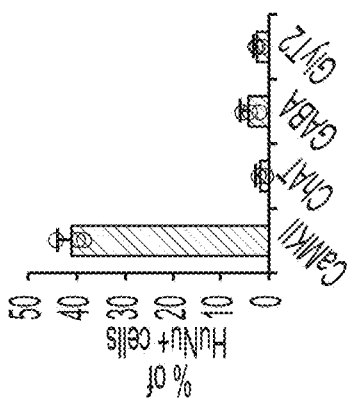
FIG. 3H  FIG. 3I  FIG. 3J  FIG. 3K  FIG. 3L
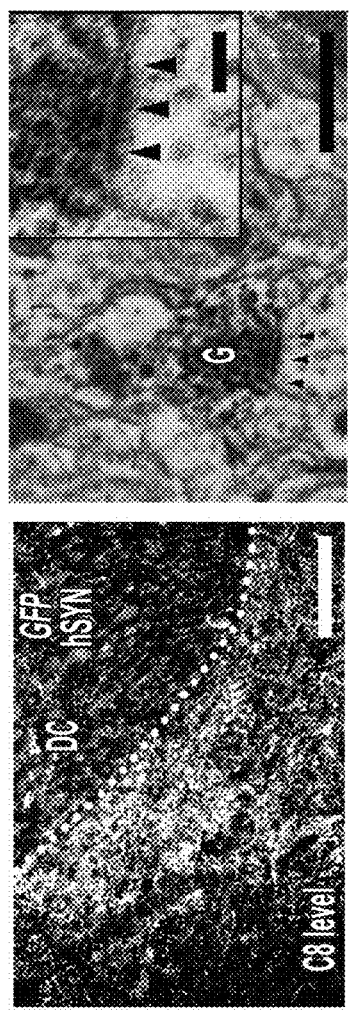
FIG. 3M
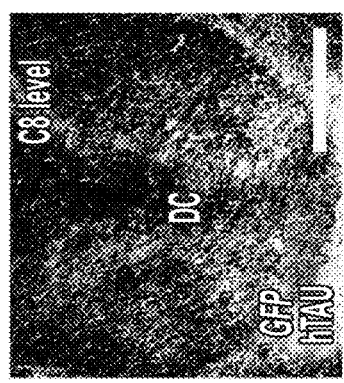
FIG. 3N
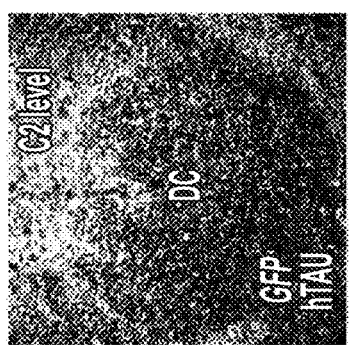
FIG. 3O
FIG. 3P

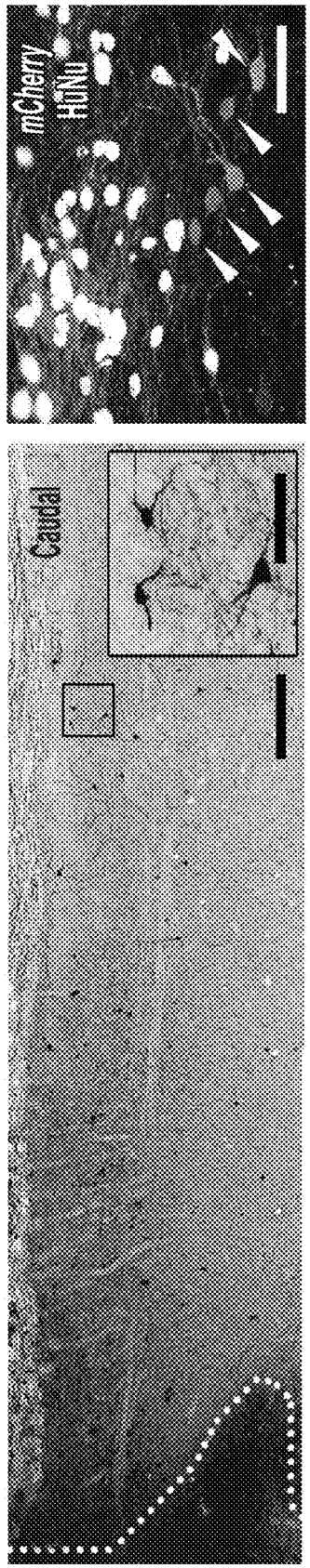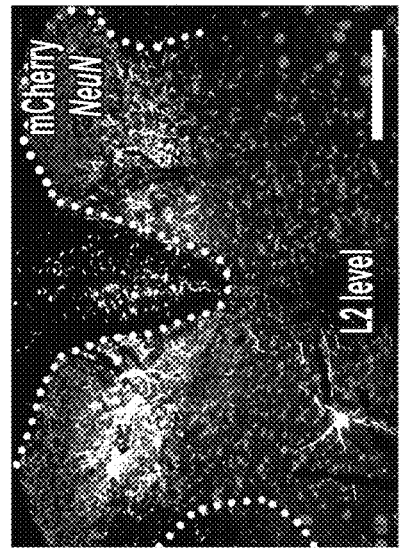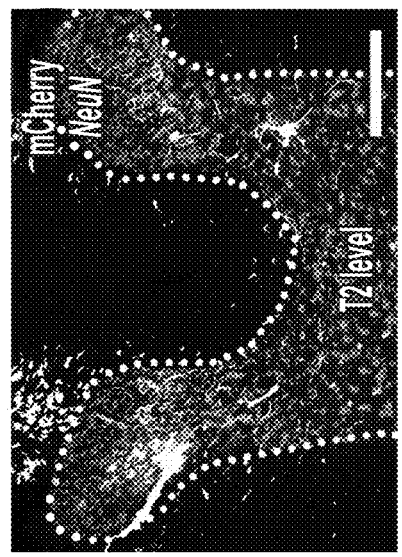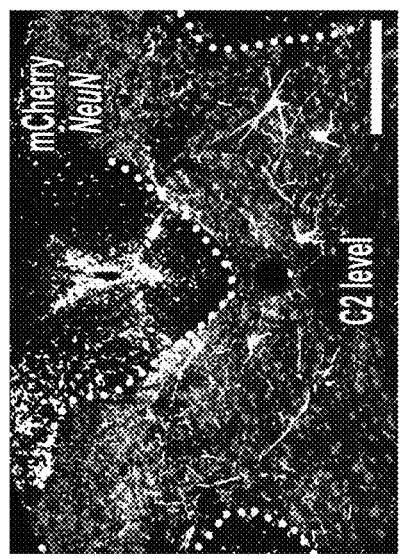
FIG. 4A
FIG. 4B
FIG. 4C
FIG. 4D
FIG. 4E

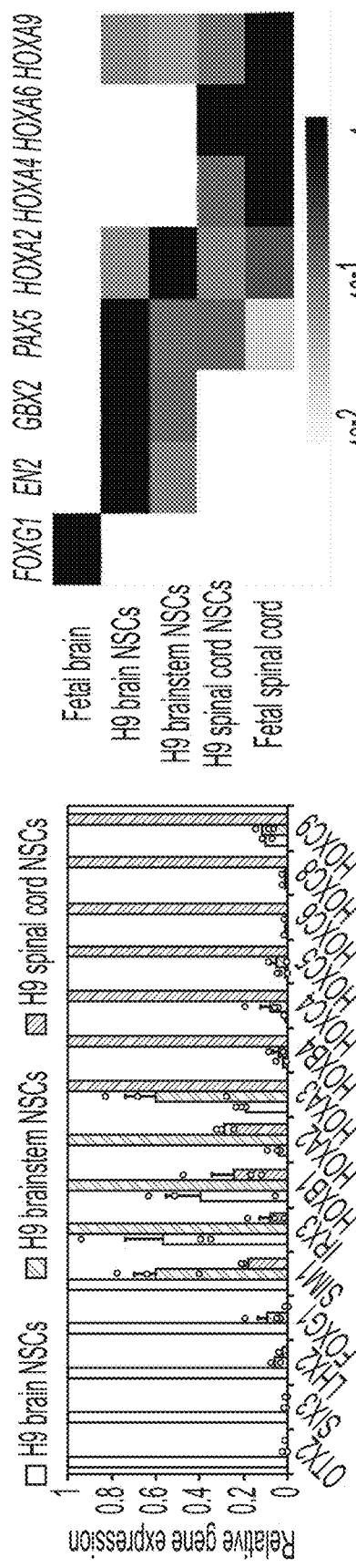
FIG. 5A
FIG. 5B
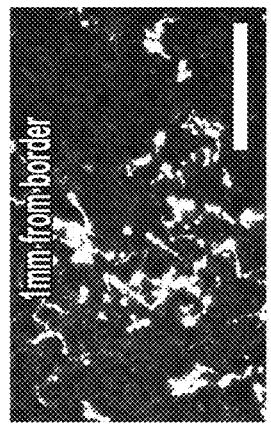
FIG. 5C
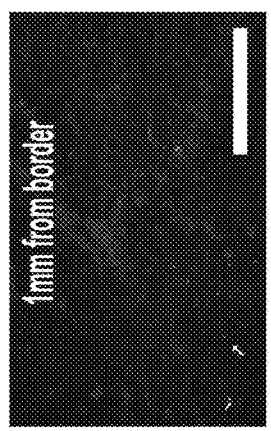
FIG. 5D
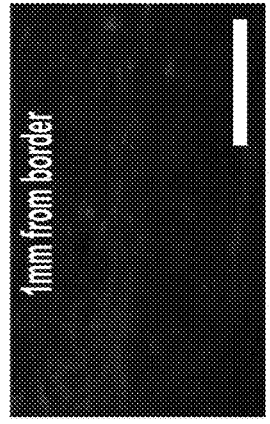
FIG. 5E
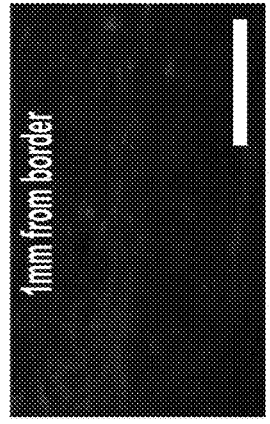
FIG. 5F
FIG. 5G
FIG. 5H

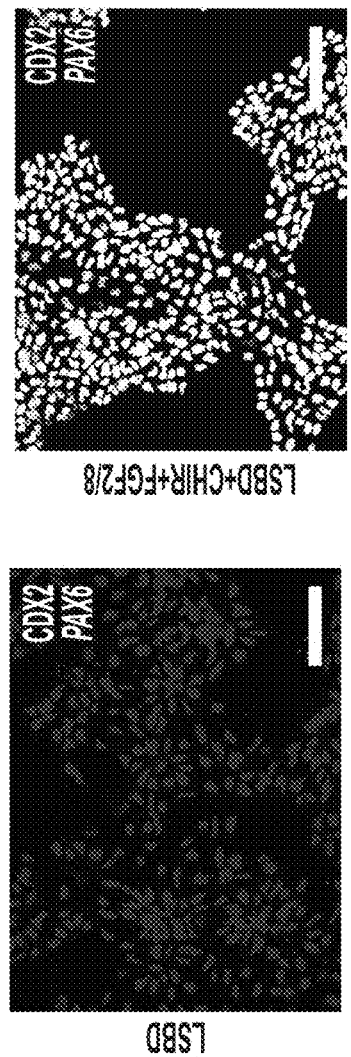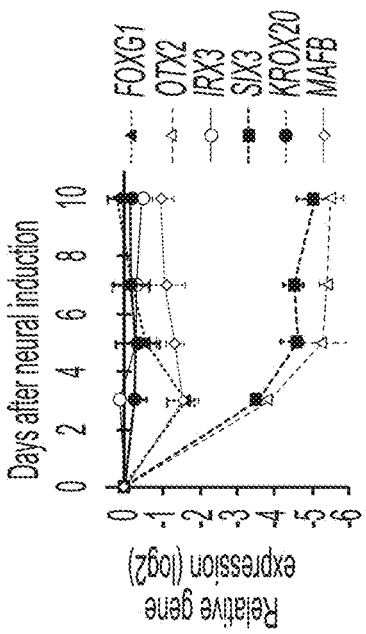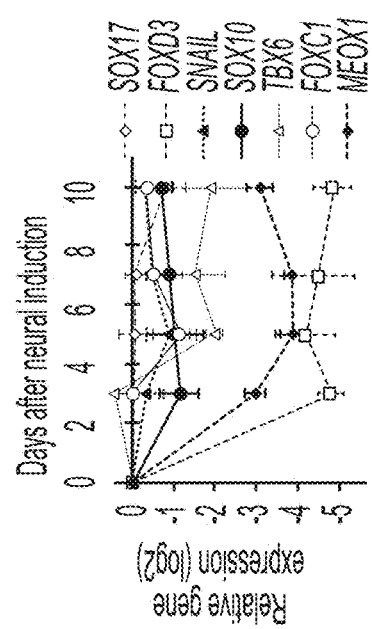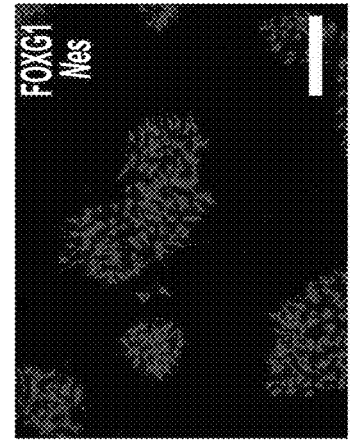
FIG. 7A  FIG. 7B  FIG. 7C  FIG. 7D  FIG. 7E  FIG. 7F

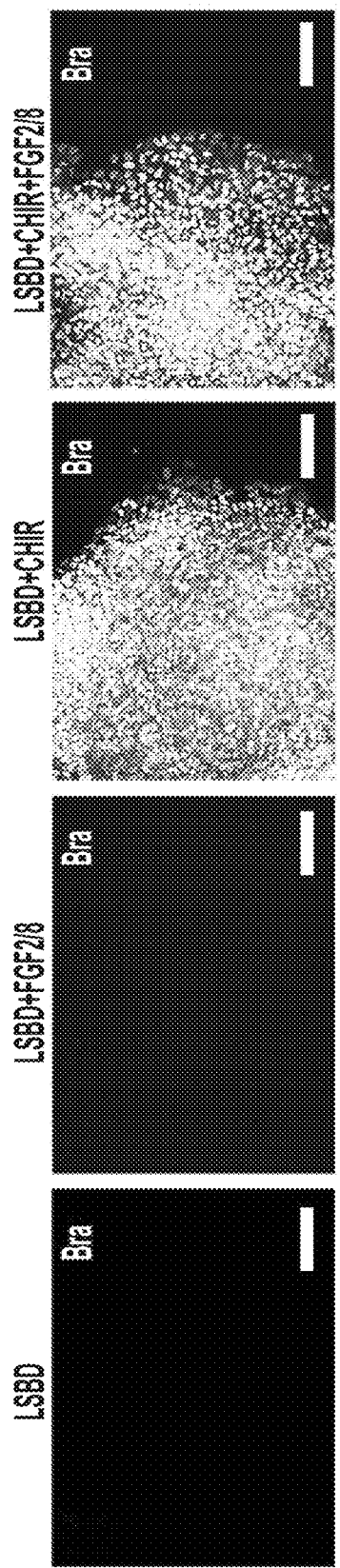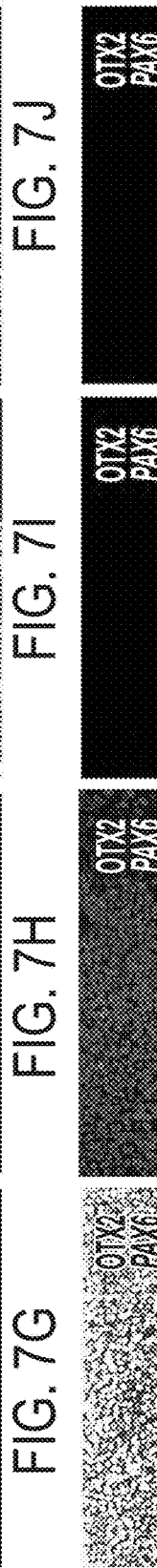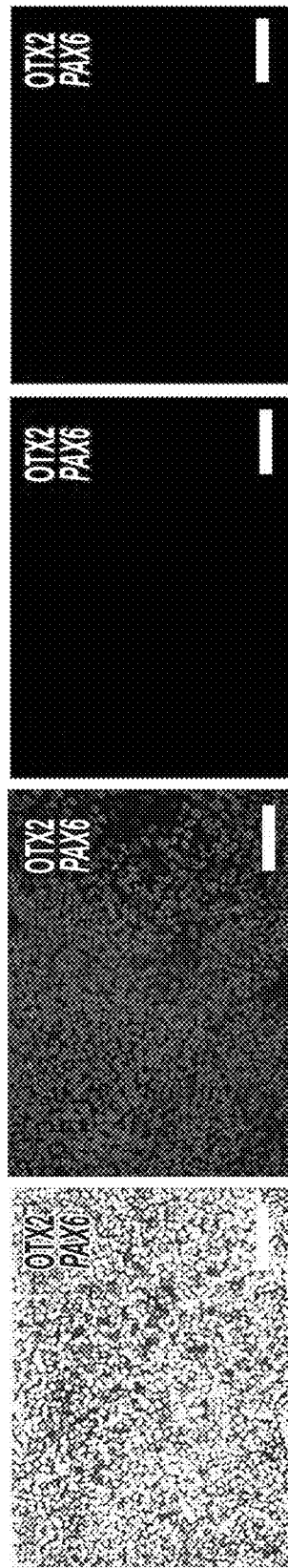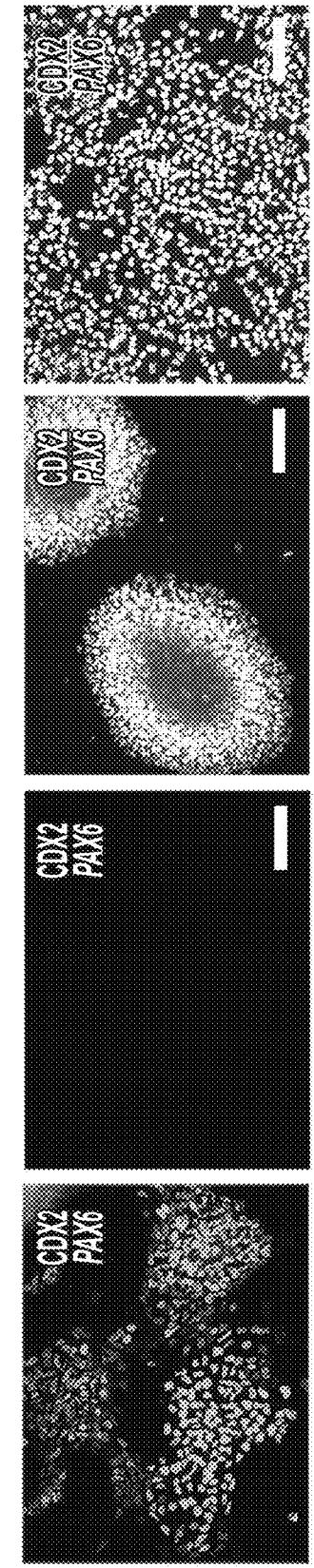

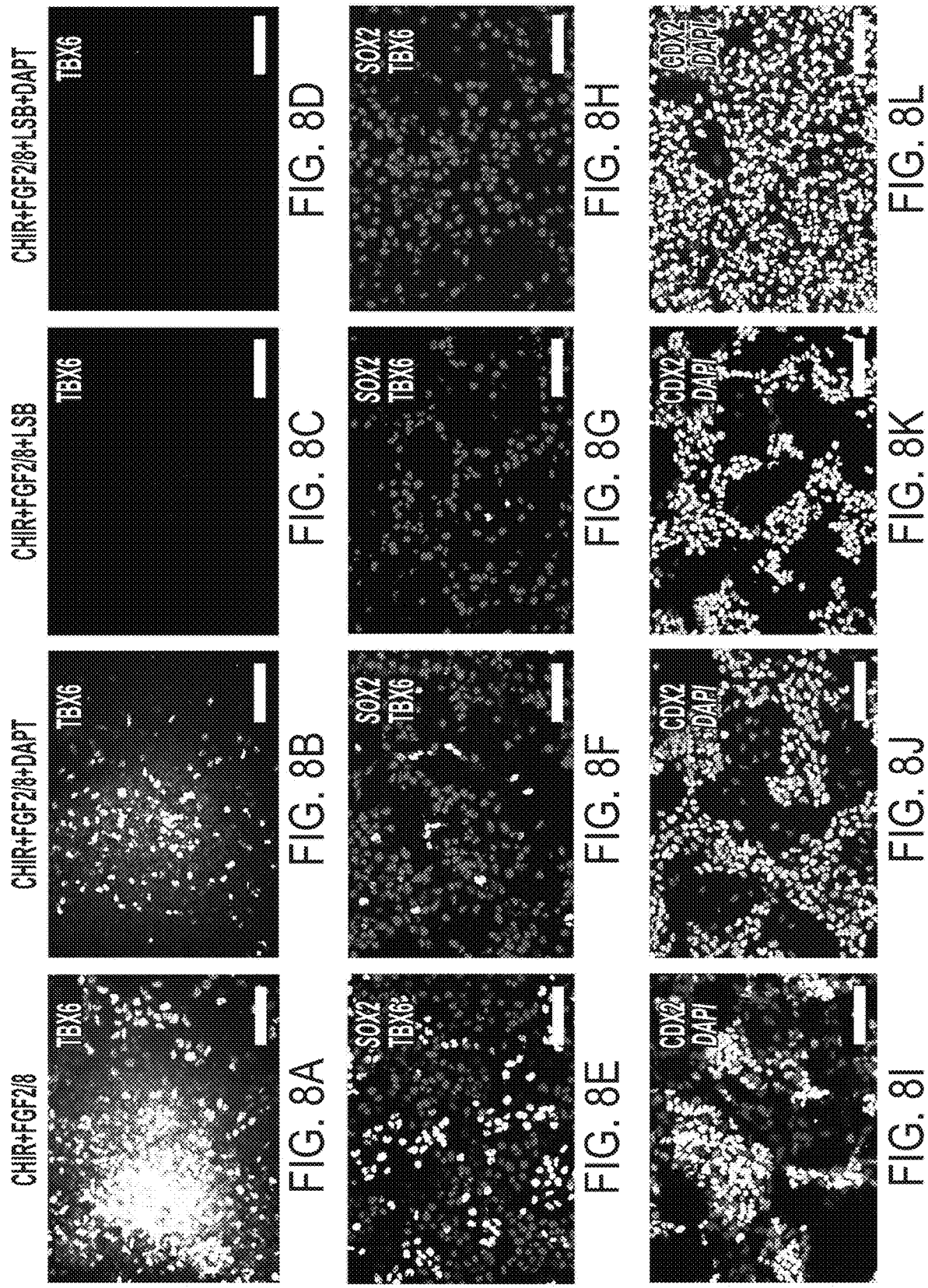

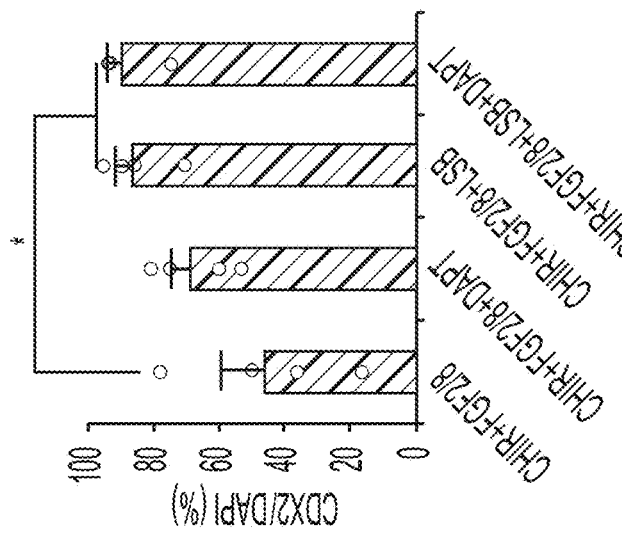
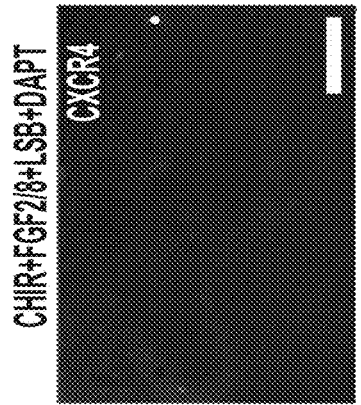
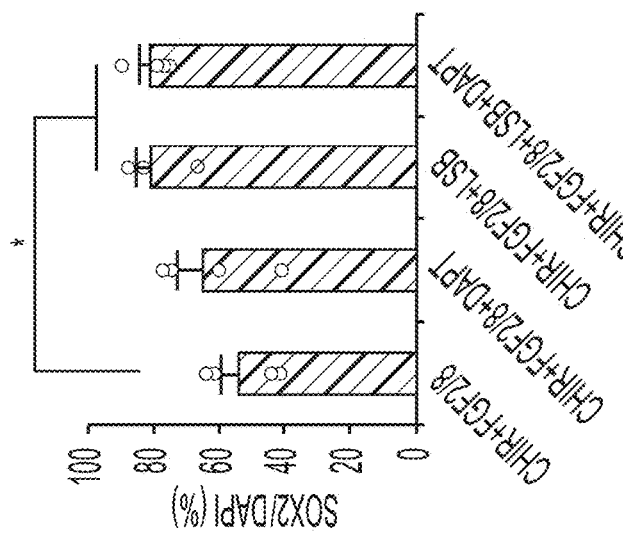
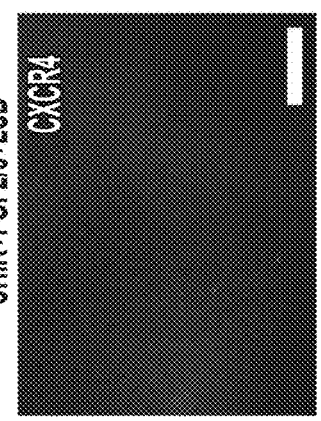
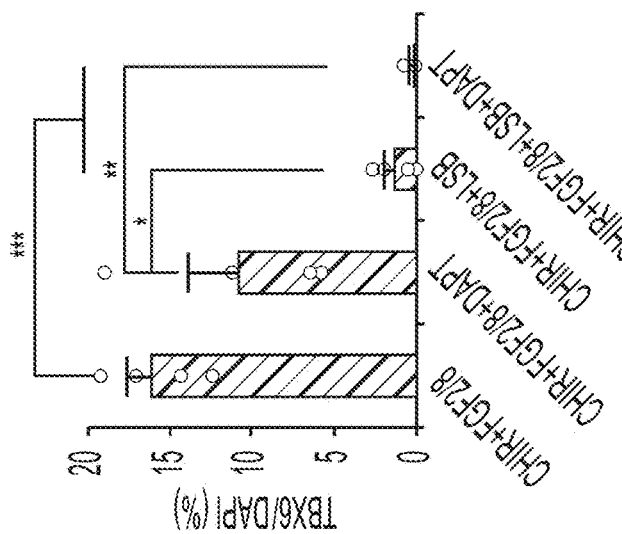
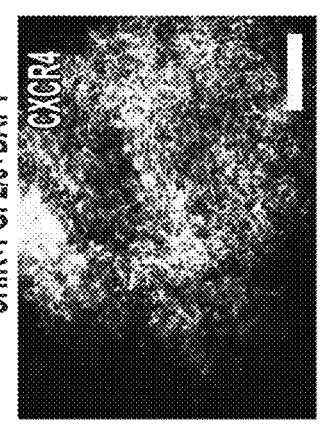
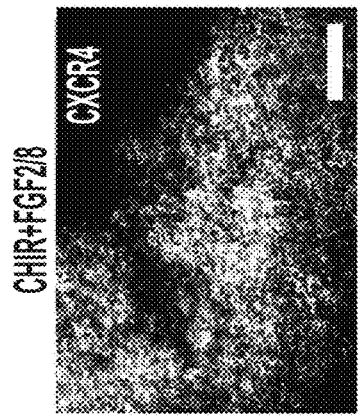

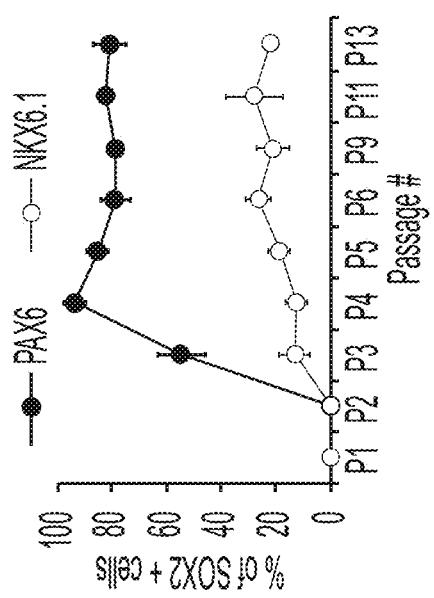
FIG. 9G
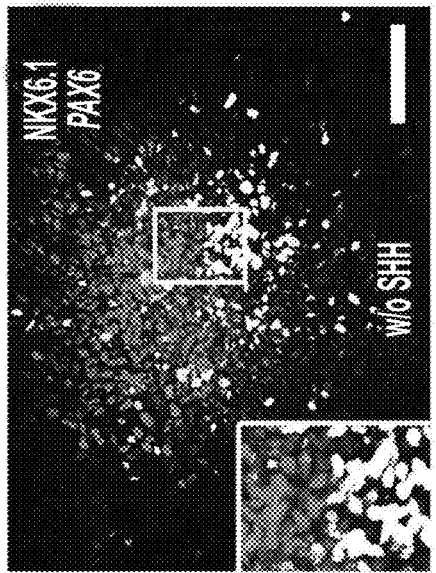
FIG. 9H
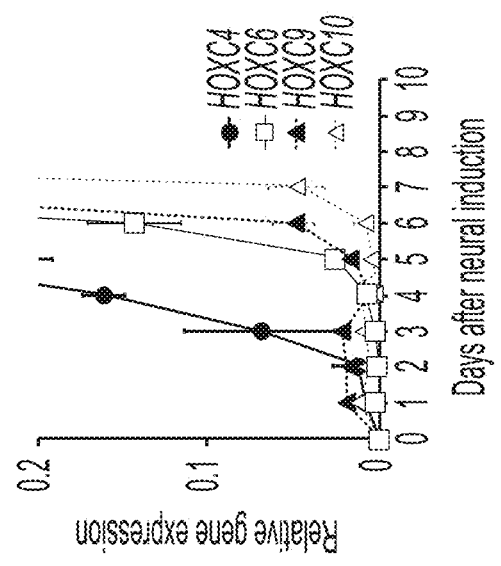
FIG. 9I
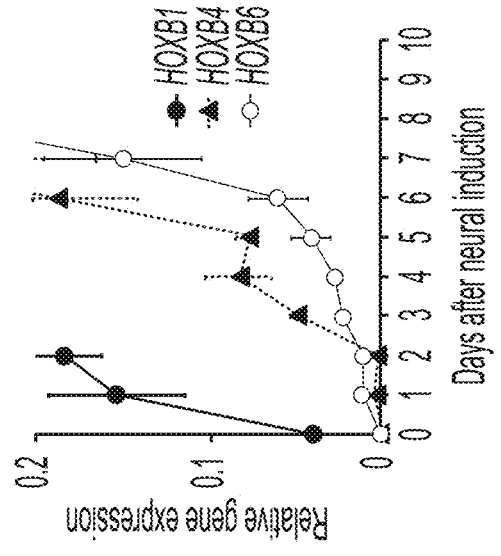
FIG. 9J
FIG. 9K
FIG. 9L

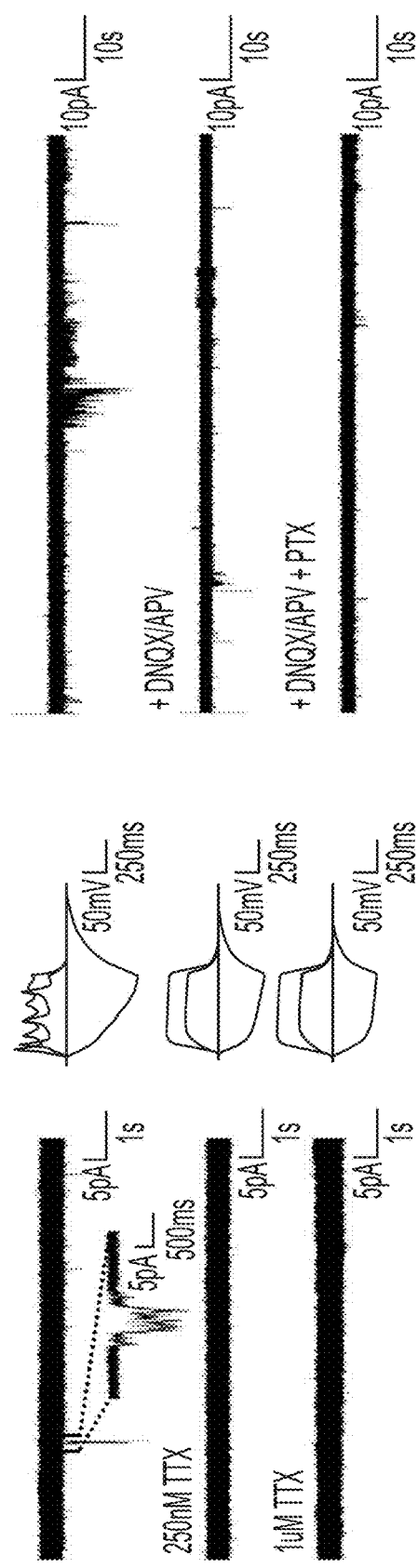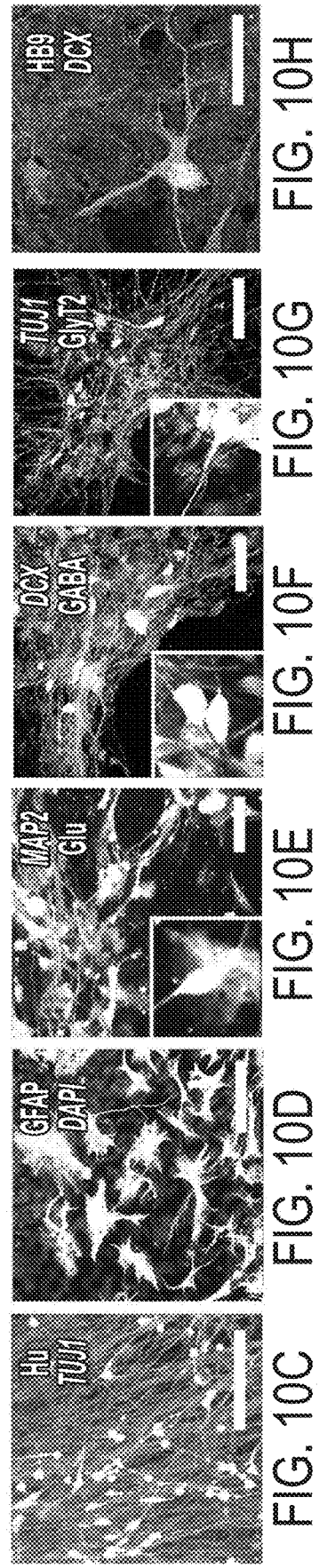

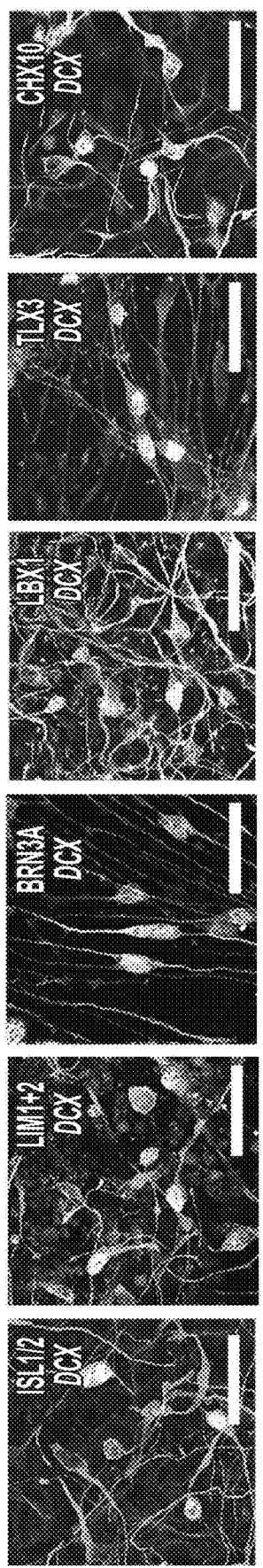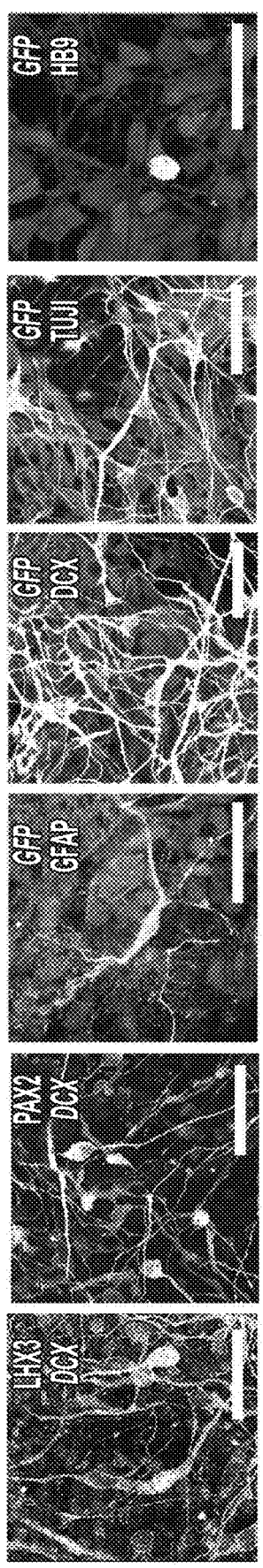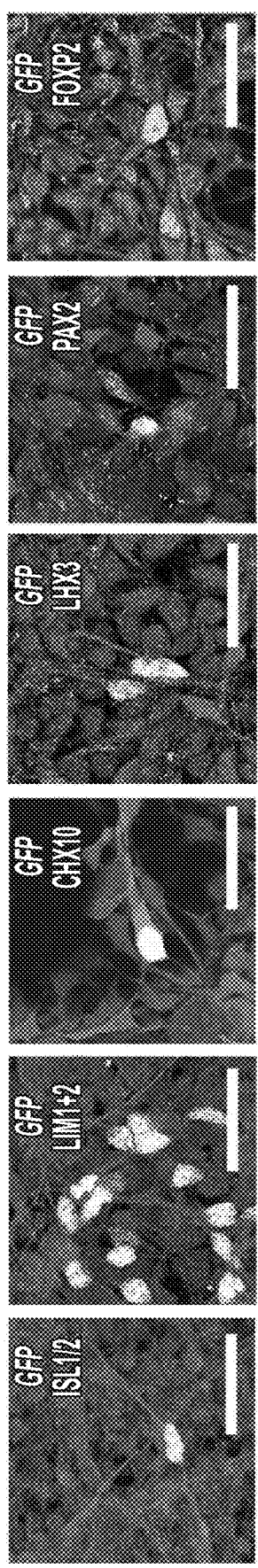

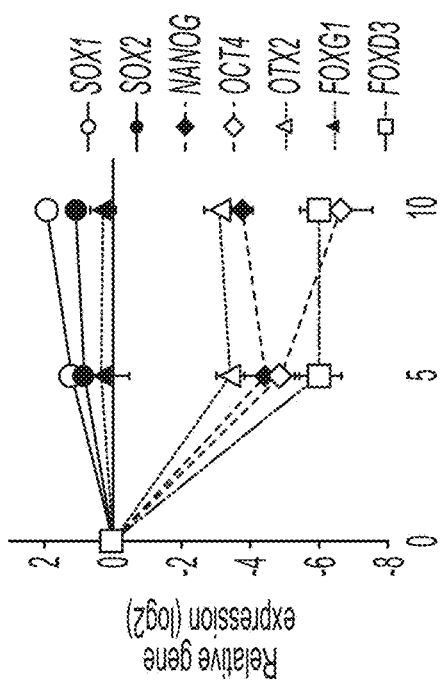
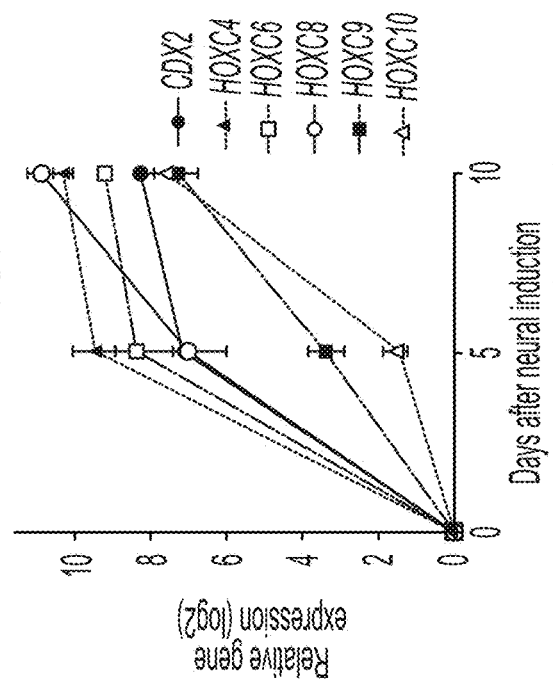
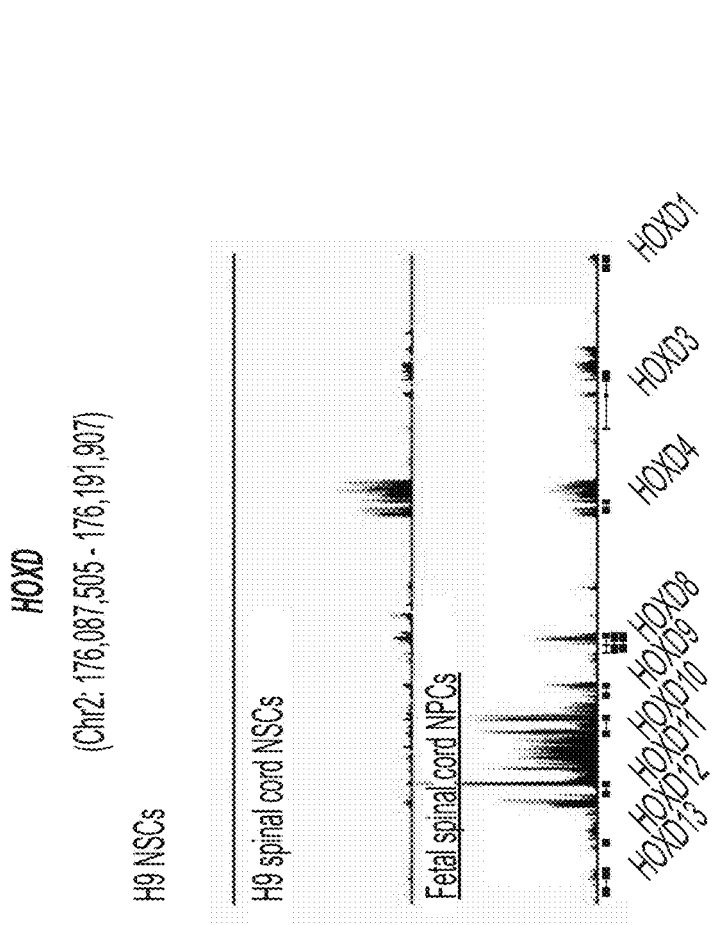
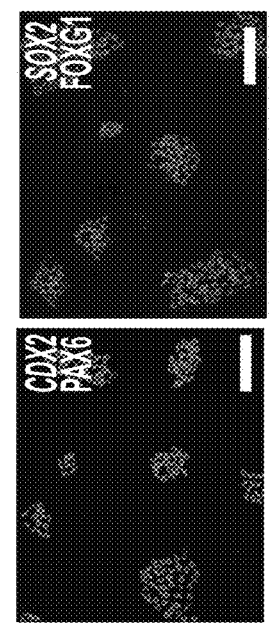
FIG. 11B
FIG. 11C   FIG. 11D   FIG. 11E

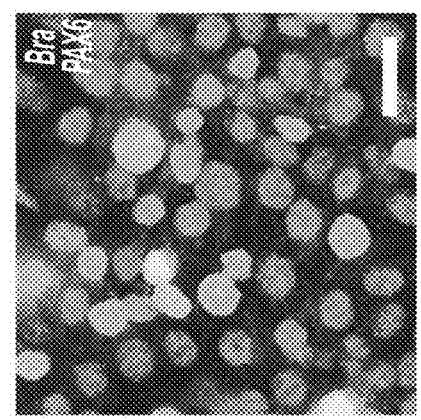
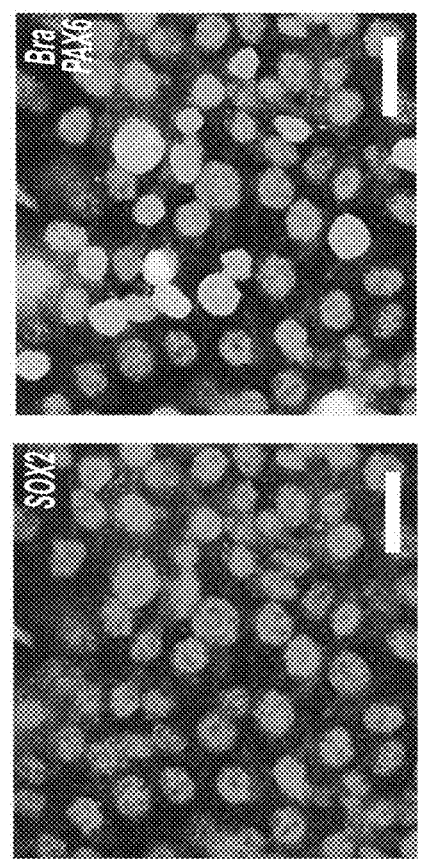
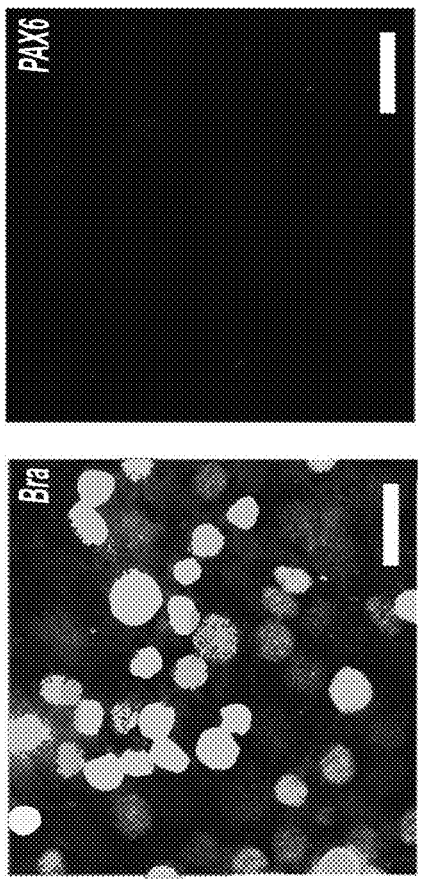
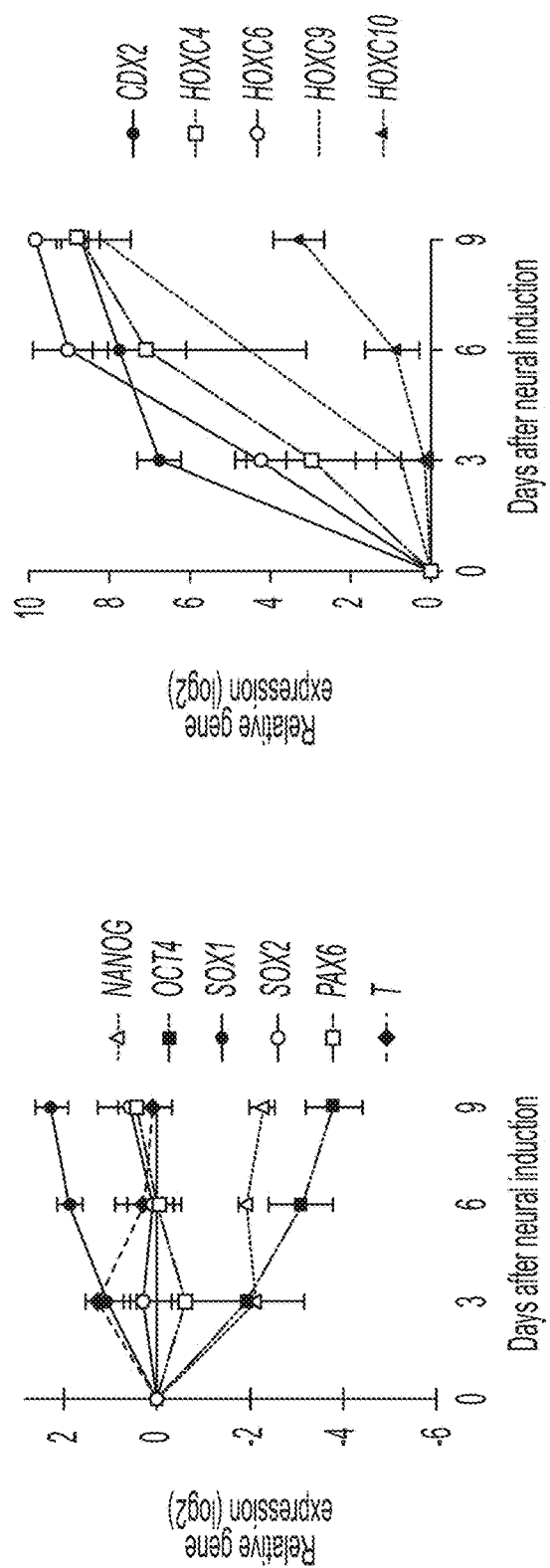
FIG. 12A  FIG. 12B  FIG. 12C  FIG. 12D  FIG. 12E  FIG. 12F

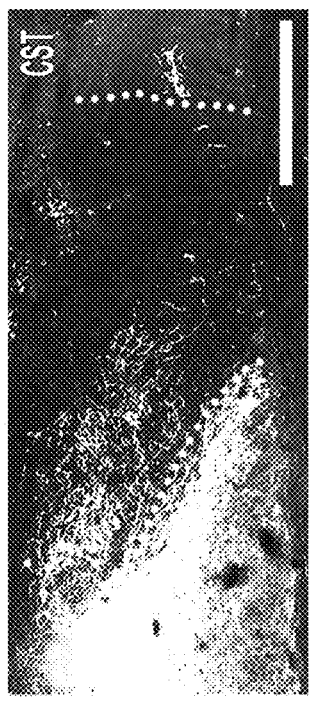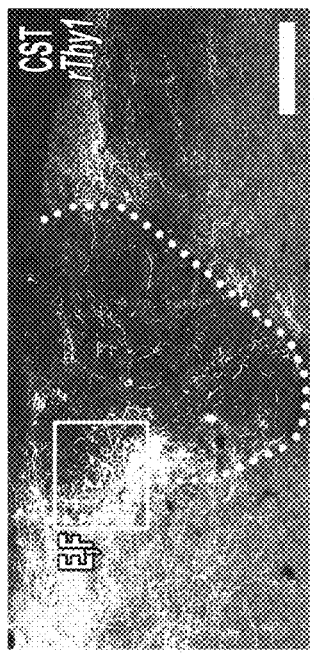
FIG. 19A  FIG. 19B
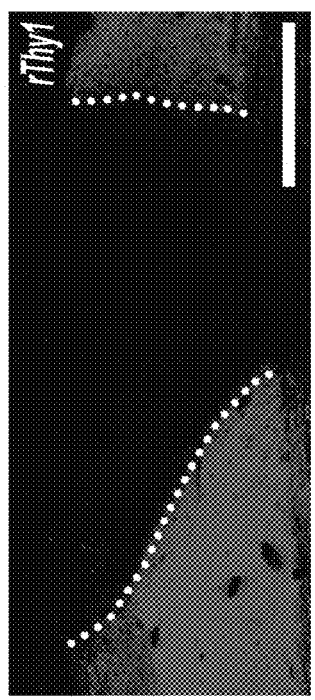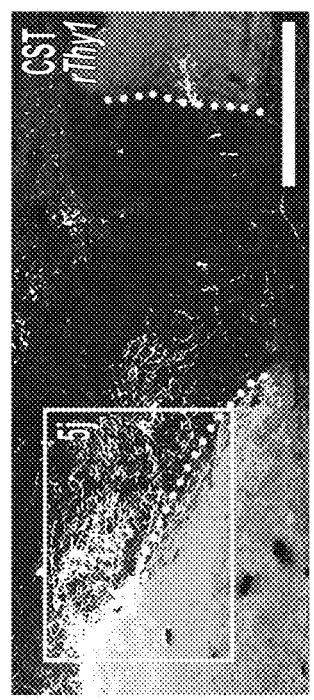
FIG. 19C  FIG. 19D

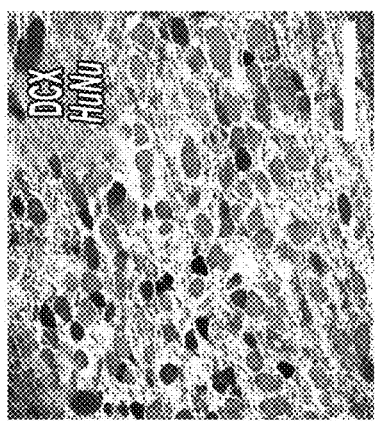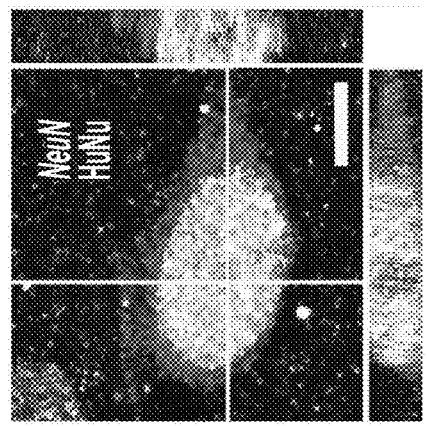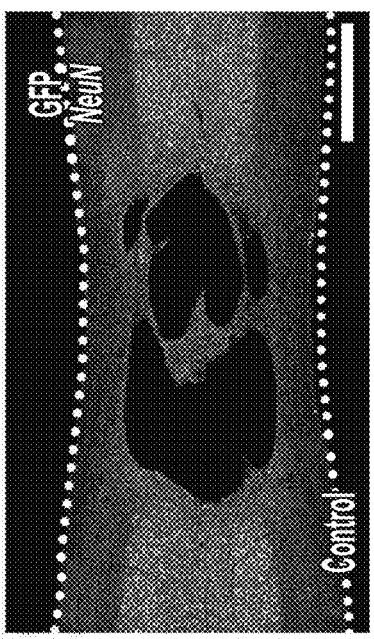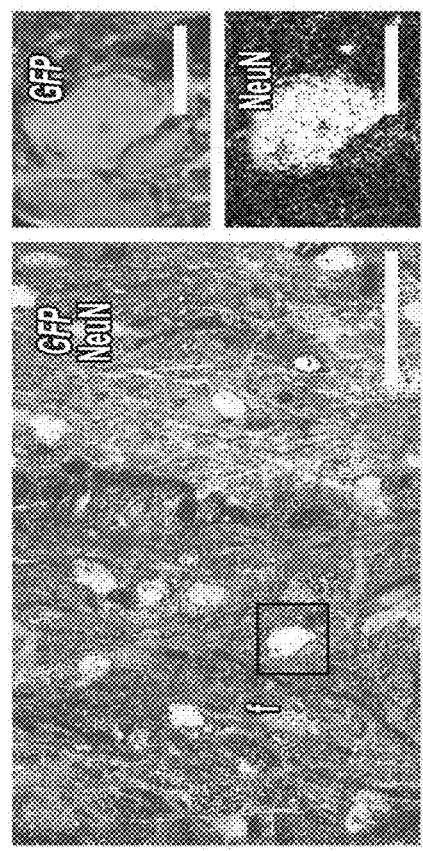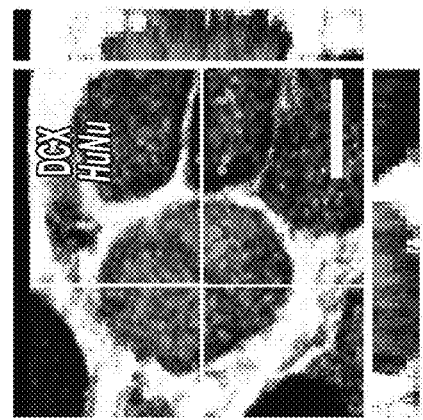

| Antibody | Species | Manufacturer | Catalog # / clone |
|---|---|---|---|
| 5-HT | Goat | ImmunoStar | 20079 |
| APC | Mouse | Millipore | OP80 / CC-1 |
| Bhlhb5 | Rat | A kind gift from Dr. Sarah Rose | |
| Brachyury (T) | Goat | R & D systems | AF2085 |
| Brn3a | Mouse | Millipore | MAB1585 / 5A3.2 |
| CaMKII | Rabbit | GeneTex | GTX61641 / EP1829Y |
| Cdx2 | Mouse | BioGenex | MU392A-100 / CDX2-88 |
| ChAT | Goat | Millipore | AB144P |
| Chx10 | Sheep | Abcam | ab16141 |
| c-Maf | Rabbit | BETHYL | A300-613A-T |
| CXCR4 | Mouse | BioLegend | 306509 / 12G5 |
| DCX | Goat | Santa Cruz Biotechnology | sc-8066 / C-18 |
| FoxG1 | Rabbit | Abcam | ab18259 |
| FoxP1 | Rabbit | Abcam | ab16645 |
| FoxP2 | Rabbit | Abcam | ab16046 |
| GABA | Rabbit | Sigma | A2052 |
| GFAP (Human) | Rabbit | Origine | AB-123-U-050 |
| GFP | Chicken | GeneTex | GTX13970 |
| Glutamate | Rabbit | Millipore | AB5018 |
| GlyT2 | Guinea pig | Millipore | AB1773 |
| Hb9 | Mouse | Developmental Studies Hybridoma Bank | 81.5C10-c |
| Hu | Human | A kind gift from Dr. Robert Darnell | |
| HuNu (Human) | Mouse | Millipore | MAB1281 / 235-1 |
| Islet 1/2 | Mouse | Developmental Studies Hybridoma Bank | 39.4D5-c |
| Ki67 | Rabbit | GeneTex | GTX16667 / SP6 |
| Lbx1 | Guinea pig | A kind gift from Dr. Thomas Müller and Dr. Carmen Birchmeier | |
| Lhx3 | Rabbit | GeneTex | GTX14555 |
| Lim1+2 | Mouse | Developmental Studies Hybridoma Bank | 4F2-c |
| MAP2 | Mouse | BD Bioscience | 556320 / Ap20 |
| Nestin | Mouse | Abcam | Ab18102 / 2C1.3A11 |
| NeuN | Mouse | Millipore | MAB377 / A60 |
| NF200 | Mouse | Millipore | AB5262 / RT97 |

TO FIG. 22B

FIG. 22A

FROM FIG. 22A

| | | | |
|---|---|---|---|
| NF66 | Mouse | Encor Biotechnology | MCA-3G8 |
| NF720 (Human) | Mouse | Millipore | MAB5294 / DP5 2.7.3 |
| NG2 (Human) | Mouse | Millipore | MAB2029 / 9.2.27 |
| Nkx2.2 | Mouse | Developmental Studies Hybridoma Bank | 74.5A5-c |
| Nkx6.1 | Mouse | Developmental Studies Hybridoma Bank | F55A12-c |
| Oct4 | Rabbit | LifeSpan BioSciences | LS-B4194 |
| Olig2 | Rabbit | IBL | 18953 |
| Otx2 | Goat | R & D systems | AF1979 |
| Pax6 | Rabbit | BioLegend | 901301 / Poly19013 |
| Pax2 | Rabbit | Life Technologies | 1557865A |
| PKCγ | Rabbit | Santa Cruz Biotechnology | sc-211 / c-19 |
| RFP | Goat | Sicgen | AB0040 |
| RFP | Rabbit | Abcam | ab62341 |
| S100β | Rabbit | Millipore | 04-1054 / EP1576Y |
| Sox1 | Goat | R & D systems | AF3369 |
| Sox2 | Rabbit | Abcam | ab97959 |
| Sox2 | Goat | Santa Cruz Biotechnology | sc-17320 / Y-17 |
| Sox2 | Mouse | R & D systems | MAB2018 |
| Synaptophysin (human) | Mouse | Novus Biologicals | NBP1-19222 |
| Synaptophysin | Mouse | Sigma | S5768 / SVP-38 |
| Tau (Human) | Mouse | BioLegend | 835201 / TAU-13 |
| Tbx6 | Goat | R & D Systems | AF4744 |
| Thy1 | Mouse | Millipore | MAB1406 / OX-7 |
| Tlx3 | Guinea pig | A kind gift from Dr. Thomas Müller and Dr. Carmen Birchmeier | |
| Tuj1 | Rabbit | BioLegend | 802001 / Poly18020 |
| VGluT1 | Guinea pig | Millipore | AB5905 |
| VGluT1 | Rabbit | Sigma | V0389 |
| VGluT2 | Guinea pig | Millipore | AB2251-I |
| VGluT2 | Mouse | Millipore | MAB5504 |
| VGluT2 | Rabbit | Sigma | V2514 / HY-19 |

Antibodies Used

FIG. 22B

| Gene symbol | Forward primer | SEQ ID NO: | Reverse primer | SEQ ID NO: |
|---|---|---|---|---|
| CDX2 | tcttctcttcctagatctgcaggc | 1 | gtccagctttctatcttagctgcc | 2 |
| EGR2 (KROX20) | actaggttttgctaccccacttcc | 3 | ttcactcactgtacaatgtcccc | 4 |
| EN2 | gggagatggcatcatctatcttcc | 5 | gtgtgtgtgtgttcacatgcatgc | 6 |
| FOXC1 | ttatcctatgttgaaggagggggg | 7 | ttgggaacactttctggcgtttgg | 8 |
| FOXO3 | taagctggtcgagcaaactcaccg | 9 | acaaagaatttccctcccatcccc | 10 |
| FOXG1 | tctaacaaggtgtggagtgtcagc | 11 | tactgcacacatggaaatctggcg | 12 |
| GAPDH | acatcaagaaggtggtgaagcagg | 13 | agcttgacaaagtggtcgttgagg | 14 |
| GBX2 | tcgctatcagaagtcagcatcagc | 15 | gttgcttcaaacacagtggagtcc | 16 |
| HOXA2 | actcctttgaccaggtggttttgc | 17 | actttcttgcaggcctcatactgc | 18 |
| HOXA3 | attgctccaaaaatctgcacgcgg | 19 | attcagcaggaagctaatgctggg | 20 |
| HOXA7 | actacctatttgtgctggctggc | 21 | gagaaggaggattgattctaggg | 22 |
| HOXA9 | cagggtctggtgttttgtataggg | 23 | acgcttgacactcacactttgtcc | 24 |
| HOXB1 | ggtcaagatttggttccagaaccg | 25 | attggtggctaggttcagttcagg | 26 |
| HOXB4 | aaaaagagagactcagagacccgg | 27 | ctgggaggggcacattttatttcc | 28 |
| HOXB6 | agcagagcaaaatgctcttgtccc | 29 | gaggctcctcttcttacttctagg | 30 |
| HOXC4 | gggtgaatttcaggggaaatgagg | 31 | ctcaaactgaacagctctgagagg | 32 |
| HOXC5 | atcaagatctggttccagaaccgc | 33 | aggaaaagcgcttttgtctgtggg | 34 |
| HOXC6 | ttagcaccgtcagtgttcctatcc | 35 | tatacaggagggtaacacgaaggg | 36 |
| HOXC8 | aggaacctgatggaaacctgaagg | 37 | atcaaacagcgaaggagagyaagg | 38 |
| HOXC9 | tagagttagttctacccagcgagg | 39 | acctggaccaaatacgatacaggg | 40 |
| HOXC10 | ctcacacacagcattctgttctcc | 41 | acacgaacactagccgaactttcc | 42 |
| IRX3 | aataaaaccagtcctcctcagccc | 43 | tacacacacacaaaggcagacacg | 44 |
| LHX2 | ccttttctaatgactcgcaaccc | 45 | atcttccaagttgttcctcggtcc | 46 |
| MAFB | aggaaaggaaaacagatcctcccc | 47 | tgagcatagcagttggttcagtgc | 48 |
| MEOX1 | acagtgtcctgtgactgcaaaagg | 49 | gcagtccacacacaaaaacctagc | 50 |
| NANOG | agtatggttggagcctaatcagcg | 51 | atcctggctaacacagtgaaaccc | 52 |
| OTX2 | ggtcatagccttcttaagcagagg | 53 | tcagtcacacaattcacacagccc | 54 |
| PAX6 | gtactgaatgactcaactgctcgg | 55 | cttagaaggaagcgacactctgc | 56 |
| POU5F1 (OCT4) | atgcattcaaactgaggtgcctgc | 57 | cccttttgtgttcccaattccttcc | 58 |
| SIM1 | ttgaccatttggggtcactcacc | 59 | gtgaactagggaaccaaatctggg | 60 |
| SIX3 | ttttctctccactctgtcactgcc | 61 | aagaaagagacagttgagcggg | 62 |
| SNAI1 (SNAIL) | tccacgaggtgtgactaactatgc | 63 | gaatagttctgggagacacatcgg | 64 |
| SOX1 | agaaccgaattcagcctgcattcg | 65 | ttatcccggactaagtcgtagtcc | 66 |
| SOX10 | acagatagtgagggtctgacatgc | 67 | agggatgagaactccactaagtcc | 68 |
| SOX17 | tgtctgccacttgaacagtttggg | 69 | gtgtgacagaggtactagtagagc | 70 |
| SOX2 | gctgcaaaagagaacaccaatccc | 71 | aaaacttcctgcaaagctcctaccg | 72 |
| TBX6 | tctttccatcgtgtcaagctcacc | 73 | ctcttacagtttctgccgttctcc | 74 |
| TBXT (T) | actggattgacctactaggtaccc | 75 | ttttttcaccgtcagtgaggttggg | 76 |

FIG. 23

SEQUENCE LISTING

```
<160> NUMBER OF SEQ ID NOS: 76

<210> SEQ ID NO 1
<211> LENGTH: 24
<212> TYPE: DNA
<213> ORGANISM: Artificial Sequence
<220> FEATURE:
<223> OTHER INFORMATION: CDX2 forward primer

<400> SEQUENCE: 1
tcttctcttc ctagatctgc aggc                                            24

<210> SEQ ID NO 2
<211> LENGTH: 24
<212> TYPE: DNA
<213> ORGANISM: Artificial Sequence
<220> FEATURE:
<223> OTHER INFORMATION: CDX2 reverse primer

<400> SEQUENCE: 2
gtccagcttt ctatcttagc tgcc                                            24
```

```
<210> SEQ ID NO 3
<211> LENGTH: 24
<212> TYPE: DNA
<213> ORGANISM: Artificial Sequence
<220> FEATURE:
<223> OTHER INFORMATION: EGR2 forward primer

<400> SEQUENCE: 3
actaggtttt gctacccccac ttcc                                            24

<210> SEQ ID NO 4
<211> LENGTH: 24
<212> TYPE: DNA
<213> ORGANISM: Artificial Sequence
<220> FEATURE:
<223> OTHER INFORMATION: EGR2 reverse primer

<400> SEQUENCE: 4
ttcactcact gtacaatgtc cccc                                             24

<210> SEQ ID NO 5
<211> LENGTH: 24
<212> TYPE: DNA
<213> ORGANISM: Artificial Sequence
<220> FEATURE:
<223> OTHER INFORMATION: EN2 forward primer

<400> SEQUENCE: 5
gggagatggc atcatctatc ttcc                                             24

<210> SEQ ID NO 6
<211> LENGTH: 24
<212> TYPE: DNA
<213> ORGANISM: Artificial Sequence
<220> FEATURE:
<223> OTHER INFORMATION: EN2 reverse primer

<400> SEQUENCE: 6
gtgtgtgtgt gttcacatgc atgc                                             24

<210> SEQ ID NO 7
<211> LENGTH: 24
<212> TYPE: DNA
<213> ORGANISM: Artificial Sequence
<220> FEATURE:
<223> OTHER INFORMATION: FOXC1 forward primer

<400> SEQUENCE: 7
ttatcctatg ttgaagggag gggg                                             24

<210> SEQ ID NO 8
<211> LENGTH: 24
<212> TYPE: DNA
<213> ORGANISM: Artificial Sequence
<220> FEATURE:
<223> OTHER INFORMATION: FOXC1 reverse primer

<400> SEQUENCE: 8
ttgggaacac tttctggcgt ttgg                                             24

<210> SEQ ID NO 9
<211> LENGTH: 24
<212> TYPE: DNA
<213> ORGANISM: Artificial Sequence
<220> FEATURE:
<223> OTHER INFORMATION: FOXD3 forward primer
```

```
<400> SEQUENCE: 9
taagctggtc gagcaaactc accg                                              24

<210> SEQ ID NO 10
<211> LENGTH: 24
<212> TYPE: DNA
<213> ORGANISM: Artificial Sequence
<220> FEATURE:
<223> OTHER INFORMATION: FOXD3 reverse primer

<400> SEQUENCE: 10
acaaagaatt tccctcccat cccc                                              24

<210> SEQ ID NO 11
<211> LENGTH: 24
<212> TYPE: DNA
<213> ORGANISM: Artificial Sequence
<220> FEATURE:
<223> OTHER INFORMATION: FOXG1 forward primer

<400> SEQUENCE: 11
tctaacaagg tgtggagtgt cagc                                              24

<210> SEQ ID NO 12
<211> LENGTH: 24
<212> TYPE: DNA
<213> ORGANISM: Artificial Sequence
<220> FEATURE:
<223> OTHER INFORMATION: FOXG1 reverse primer

<400> SEQUENCE: 12
tactgcacac atggaaatct ggcg                                              24

<210> SEQ ID NO 13
<211> LENGTH: 24
<212> TYPE: DNA
<213> ORGANISM: Artificial Sequence
<220> FEATURE:
<223> OTHER INFORMATION: GAPDH forward primer

<400> SEQUENCE: 13
acatcaagaa ggtggtgaag cagg                                              24

<210> SEQ ID NO 14
<211> LENGTH: 24
<212> TYPE: DNA
<213> ORGANISM: Artificial Sequence
<220> FEATURE:
<223> OTHER INFORMATION: GAPDH reverse primer

<400> SEQUENCE: 14
agcttgacaa agtggtcgtt gagg                                              24

<210> SEQ ID NO 15
<211> LENGTH: 24
<212> TYPE: DNA
<213> ORGANISM: Artificial Sequence
<220> FEATURE:
<223> OTHER INFORMATION: GBX2 forward primer

<400> SEQUENCE: 15
tcgctatcag aagtcagcat cagc                                              24

<210> SEQ ID NO 16
<211> LENGTH: 24
```

```
<212> TYPE: DNA
<213> ORGANISM: Artificial Sequence
<220> FEATURE:
<223> OTHER INFORMATION: GBX2 reverse primer

<400> SEQUENCE: 16
gttgcttcaa acacagtgga gtcc                                              24

<210> SEQ ID NO 17
<211> LENGTH: 24
<212> TYPE: DNA
<213> ORGANISM: Artificial Sequence
<220> FEATURE:
<223> OTHER INFORMATION: HOXA2 forward primer

<400> SEQUENCE: 17
actcctttga ccaggtggtt ttgc                                              24

<210> SEQ ID NO 18
<211> LENGTH: 24
<212> TYPE: DNA
<213> ORGANISM: Artificial Sequence
<220> FEATURE:
<223> OTHER INFORMATION: HOXA2 reverse primer

<400> SEQUENCE: 18
actttcttgc aggcctcata ctgc                                              24

<210> SEQ ID NO 19
<211> LENGTH: 24
<212> TYPE: DNA
<213> ORGANISM: Artificial Sequence
<220> FEATURE:
<223> OTHER INFORMATION: HOXA3 forward primer

<400> SEQUENCE: 19
attgctccaa aaatctgcac gcgg                                              24

<210> SEQ ID NO 20
<211> LENGTH: 24
<212> TYPE: DNA
<213> ORGANISM: Artificial Sequence
<220> FEATURE:
<223> OTHER INFORMATION: HOXA3 reverse primer

<400> SEQUENCE: 20
attcagcagg aagctaatgc tggg                                              24

<210> SEQ ID NO 21
<211> LENGTH: 24
<212> TYPE: DNA
<213> ORGANISM: Artificial Sequence
<220> FEATURE:
<223> OTHER INFORMATION: HOXA7 forward primer

<400> SEQUENCE: 21
actacctatt ttgtgctggc tggc                                              24

<210> SEQ ID NO 22
<211> LENGTH: 24
<212> TYPE: DNA
<213> ORGANISM: Artificial Sequence
<220> FEATURE:
<223> OTHER INFORMATION: HOXA7 reverse primer

<400> SEQUENCE: 22
```
gagaaggagg gattgattct aggg            24

<210> SEQ ID NO 23
<211> LENGTH: 24
<212> TYPE: DNA
<213> ORGANISM: Artificial Sequence
<220> FEATURE:
<223> OTHER INFORMATION: HOXA9 forward primer

<400> SEQUENCE: 23
cagggtctgg tgttttgtat aggg            24

<210> SEQ ID NO 24
<211> LENGTH: 24
<212> TYPE: DNA
<213> ORGANISM: Artificial Sequence
<220> FEATURE:
<223> OTHER INFORMATION: HOXA9 reverse primer

<400> SEQUENCE: 24
acgcttgaca ctcacacttt gtcc            24

<210> SEQ ID NO 25
<211> LENGTH: 24
<212> TYPE: DNA
<213> ORGANISM: Artificial Sequence
<220> FEATURE:
<223> OTHER INFORMATION: HOXB1 forward primer

<400> SEQUENCE: 25
ggtcaagatt tggttccaga accg            24

<210> SEQ ID NO 26
<211> LENGTH: 24
<212> TYPE: DNA
<213> ORGANISM: Artificial Sequence
<220> FEATURE:
<223> OTHER INFORMATION: HOXB1 reverse primer

<400> SEQUENCE: 26
attggtggct aggttcagtt cagg            24

<210> SEQ ID NO 27
<211> LENGTH: 24
<212> TYPE: DNA
<213> ORGANISM: Artificial Sequence
<220> FEATURE:
<223> OTHER INFORMATION: HOXB4 forward primer

<400> SEQUENCE: 27
aaaaagagag actcagagac ccgg            24

<210> SEQ ID NO 28
<211> LENGTH: 24
<212> TYPE: DNA
<213> ORGANISM: Artificial Sequence
<220> FEATURE:
<223> OTHER INFORMATION: HOXB4 reverse primer

<400> SEQUENCE: 28
ctgggagggg cacattttat ttcc            24

<210> SEQ ID NO 29
<211> LENGTH: 24
<212> TYPE: DNA
<213> ORGANISM: Artificial Sequence

```
<220> FEATURE:
<223> OTHER INFORMATION: HOXB6 forward primer

<400> SEQUENCE: 29
agcagagcaa aatgctcttg tccc                                          24

<210> SEQ ID NO 30
<211> LENGTH: 24
<212> TYPE: DNA
<213> ORGANISM: Artificial Sequence
<220> FEATURE:
<223> OTHER INFORMATION: HOXB6 reverse primer

<400> SEQUENCE: 30
gaggctcctc ttcttacttc tagg                                          24

<210> SEQ ID NO 31
<211> LENGTH: 24
<212> TYPE: DNA
<213> ORGANISM: Artificial Sequence
<220> FEATURE:
<223> OTHER INFORMATION: HOXC4 forward primer

<400> SEQUENCE: 31
gggtgaattt cagggaaat gagg                                           24

<210> SEQ ID NO 32
<211> LENGTH: 24
<212> TYPE: DNA
<213> ORGANISM: Artificial Sequence
<220> FEATURE:
<223> OTHER INFORMATION: HOXC4 reverse primer

<400> SEQUENCE: 32
ctcaaactga acagctctga gagg                                          24

<210> SEQ ID NO 33
<211> LENGTH: 24
<212> TYPE: DNA
<213> ORGANISM: Artificial Sequence
<220> FEATURE:
<223> OTHER INFORMATION: HOXC5 forward primer

<400> SEQUENCE: 33
atcaagatct ggttccagaa ccgc                                          24

<210> SEQ ID NO 34
<211> LENGTH: 24
<212> TYPE: DNA
<213> ORGANISM: Artificial Sequence
<220> FEATURE:
<223> OTHER INFORMATION: HOXC5 reverse primer

<400> SEQUENCE: 34
aggaaaagcg cttttgtctg tggg                                          24

<210> SEQ ID NO 35
<211> LENGTH: 24
<212> TYPE: DNA
<213> ORGANISM: Artificial Sequence
<220> FEATURE:
<223> OTHER INFORMATION: HOXC6 forward primer

<400> SEQUENCE: 35
ttagcaccgt cagtgttcct atcc                                          24
```

<210> SEQ ID NO 36
<211> LENGTH: 24
<212> TYPE: DNA
<213> ORGANISM: Artificial Sequence
<220> FEATURE:
<223> OTHER INFORMATION: HOXC6 reverse primer

<400> SEQUENCE: 36
tatacaggag ggtaacacga aggg                                            24

<210> SEQ ID NO 37
<211> LENGTH: 24
<212> TYPE: DNA
<213> ORGANISM: Artificial Sequence
<220> FEATURE:
<223> OTHER INFORMATION: HOXC8 forward primer

<400> SEQUENCE: 37
aggaacctga tggaaacctg aagg                                            24

<210> SEQ ID NO 38
<211> LENGTH: 24
<212> TYPE: DNA
<213> ORGANISM: Artificial Sequence
<220> FEATURE:
<223> OTHER INFORMATION: HOXC8 reverse primer

<400> SEQUENCE: 38
atcaaacagc gaaggagagg aagg                                            24

<210> SEQ ID NO 39
<211> LENGTH: 24
<212> TYPE: DNA
<213> ORGANISM: Artificial Sequence
<220> FEATURE:
<223> OTHER INFORMATION: HOXC9 forward primer

<400> SEQUENCE: 39
tagagttagt tctacccagc gagg                                            24

<210> SEQ ID NO 40
<211> LENGTH: 24
<212> TYPE: DNA
<213> ORGANISM: Artificial Sequence
<220> FEATURE:
<223> OTHER INFORMATION: HOXC9 reverse primer

<400> SEQUENCE: 40
acctggacca aatacgatac aggg                                            24

<210> SEQ ID NO 41
<211> LENGTH: 24
<212> TYPE: DNA
<213> ORGANISM: Artificial Sequence
<220> FEATURE:
<223> OTHER INFORMATION: HOXC10 forward primer

<400> SEQUENCE: 41
ctcacacaca gcattctgtt ctcc                                            24

<210> SEQ ID NO 42
<211> LENGTH: 24
<212> TYPE: DNA
<213> ORGANISM: Artificial Sequence
<220> FEATURE:
<223> OTHER INFORMATION: HOXC10 reverse primer

```
<400> SEQUENCE: 42
acacgaacac tagccgaact ttcc                                              24

<210> SEQ ID NO 43
<211> LENGTH: 24
<212> TYPE: DNA
<213> ORGANISM: Artificial Sequence
<220> FEATURE:
<223> OTHER INFORMATION: IRX3 forward primer

<400> SEQUENCE: 43
aataaaacca gtcctcctca gccc                                              24

<210> SEQ ID NO 44
<211> LENGTH: 24
<212> TYPE: DNA
<213> ORGANISM: Artificial Sequence
<220> FEATURE:
<223> OTHER INFORMATION: IRX3 reverse primer

<400> SEQUENCE: 44
tacacacaca caaaggcaga cacg                                              24

<210> SEQ ID NO 45
<211> LENGTH: 24
<212> TYPE: DNA
<213> ORGANISM: Artificial Sequence
<220> FEATURE:
<223> OTHER INFORMATION: LHX2 forward primer

<400> SEQUENCE: 45
ccttttctaa tgactcgcaa cccc                                              24

<210> SEQ ID NO 46
<211> LENGTH: 24
<212> TYPE: DNA
<213> ORGANISM: Artificial Sequence
<220> FEATURE:
<223> OTHER INFORMATION: LHX2 reverse primer

<400> SEQUENCE: 46
atcttccaag ttgttcctcg gtcc                                              24

<210> SEQ ID NO 47
<211> LENGTH: 24
<212> TYPE: DNA
<213> ORGANISM: Artificial Sequence
<220> FEATURE:
<223> OTHER INFORMATION: MAFB forward primer

<400> SEQUENCE: 47
aggaaaggaa aacagatcct cccc                                              24

<210> SEQ ID NO 48
<211> LENGTH: 24
<212> TYPE: DNA
<213> ORGANISM: Artificial Sequence
<220> FEATURE:
<223> OTHER INFORMATION: MAFB reverse primer

<400> SEQUENCE: 48
tgagcatagc agttggttca gtgc                                              24

<210> SEQ ID NO 49
```

```
<211> LENGTH: 24
<212> TYPE: DNA
<213> ORGANISM: Artificial Sequence
<220> FEATURE:
<223> OTHER INFORMATION: MEOX1 forward primer

<400> SEQUENCE: 49
acagtgtcct gtgactgcaa aagg                                              24

<210> SEQ ID NO 50
<211> LENGTH: 24
<212> TYPE: DNA
<213> ORGANISM: Artificial Sequence
<220> FEATURE:
<223> OTHER INFORMATION: MEOX1 reverse primer

<400> SEQUENCE: 50
gcagtccaca cacaaaaacc tagc                                              24

<210> SEQ ID NO 51
<211> LENGTH: 24
<212> TYPE: DNA
<213> ORGANISM: Artificial Sequence
<220> FEATURE:
<223> OTHER INFORMATION: NANOG forward primer

<400> SEQUENCE: 51
agtatggttg gagcctaatc agcg                                              24

<210> SEQ ID NO 52
<211> LENGTH: 24
<212> TYPE: DNA
<213> ORGANISM: Artificial Sequence
<220> FEATURE:
<223> OTHER INFORMATION: NANOG reverse primer

<400> SEQUENCE: 52
atcctggcta acacagtgaa accc                                              24

<210> SEQ ID NO 53
<211> LENGTH: 24
<212> TYPE: DNA
<213> ORGANISM: Artificial Sequence
<220> FEATURE:
<223> OTHER INFORMATION: OTX2 forward primer

<400> SEQUENCE: 53
ggtcatagcc ttcttaagca gagg                                              24

<210> SEQ ID NO 54
<211> LENGTH: 24
<212> TYPE: DNA
<213> ORGANISM: Artificial Sequence
<220> FEATURE:
<223> OTHER INFORMATION: OTX2 reverse primer

<400> SEQUENCE: 54
tcagtcacac aattcacaca gccc                                              24

<210> SEQ ID NO 55
<211> LENGTH: 24
<212> TYPE: DNA
<213> ORGANISM: Artificial Sequence
<220> FEATURE:
<223> OTHER INFORMATION: PAX6 forward primer

<400> SEQUENCE: 55
```
gtactgaatg actcaactgc tcgg                                          24

<210> SEQ ID NO 56
<211> LENGTH: 24
<212> TYPE: DNA
<213> ORGANISM: Artificial Sequence
<220> FEATURE:
<223> OTHER INFORMATION: PAX6 reverse primer

<400> SEQUENCE: 56
ctttagaagg aagcgacact ctgc                                          24

<210> SEQ ID NO 57
<211> LENGTH: 24
<212> TYPE: DNA
<213> ORGANISM: Artificial Sequence
<220> FEATURE:
<223> OTHER INFORMATION: POU4F1 (OCT4) forward primer

<400> SEQUENCE: 57
atgcattcaa actgaggtgc ctgc                                          24

<210> SEQ ID NO 58
<211> LENGTH: 24
<212> TYPE: DNA
<213> ORGANISM: Artificial Sequence
<220> FEATURE:
<223> OTHER INFORMATION: POU5F1 (OCT4) reverse primer

<400> SEQUENCE: 58
ccctttgtgt tcccaattcc ttcc                                          24

<210> SEQ ID NO 59
<211> LENGTH: 24
<212> TYPE: DNA
<213> ORGANISM: Artificial Sequence
<220> FEATURE:
<223> OTHER INFORMATION: SIM1 forward primer

<400> SEQUENCE: 59
ttgaccattt tggggtcact cacc                                          24

<210> SEQ ID NO 60
<211> LENGTH: 24
<212> TYPE: DNA
<213> ORGANISM: Artificial Sequence
<220> FEATURE:
<223> OTHER INFORMATION: SIM1 reverse primer

<400> SEQUENCE: 60
gtgaactagg gaaccaaatc tggg                                          24

<210> SEQ ID NO 61
<211> LENGTH: 24
<212> TYPE: DNA
<213> ORGANISM: Artificial Sequence
<220> FEATURE:
<223> OTHER INFORMATION: SIX3 forward primer

<400> SEQUENCE: 61
ttttctctcc actctgtcac tgcc                                          24

<210> SEQ ID NO 62
<211> LENGTH: 24
<212> TYPE: DNA

<213> ORGANISM: Artificial Sequence
<220> FEATURE:
<223> OTHER INFORMATION: SIX3 reverse primer

<400> SEQUENCE: 62
aagaaaagag acagttgagc gggg							24

<210> SEQ ID NO 63
<211> LENGTH: 24
<212> TYPE: DNA
<213> ORGANISM: Artificial Sequence
<220> FEATURE:
<223> OTHER INFORMATION: SNAI1 forward primer

<400> SEQUENCE: 63
tccacgaggt gtgactaact atgc							24

<210> SEQ ID NO 64
<211> LENGTH: 24
<212> TYPE: DNA
<213> ORGANISM: Artificial Sequence
<220> FEATURE:
<223> OTHER INFORMATION: SNAI1 reverse primer

<400> SEQUENCE: 64
gaatagttct gggagacaca tcgg							24

<210> SEQ ID NO 65
<211> LENGTH: 24
<212> TYPE: DNA
<213> ORGANISM: Artificial Sequence
<220> FEATURE:
<223> OTHER INFORMATION: SOX1 forward primer

<400> SEQUENCE: 65
agaaccgaat tcagcctgca ttcg							24

<210> SEQ ID NO 66
<211> LENGTH: 24
<212> TYPE: DNA
<213> ORGANISM: Artificial Sequence
<220> FEATURE:
<223> OTHER INFORMATION: SOX1 reverse primer

<400> SEQUENCE: 66
ttatcccgga ctaagtcgta gtgg							24

<210> SEQ ID NO 67
<211> LENGTH: 24
<212> TYPE: DNA
<213> ORGANISM: Artificial Sequence
<220> FEATURE:
<223> OTHER INFORMATION: SOX10 forward primer

<400> SEQUENCE: 67
acagatagtg agggtctgac atgc							24

<210> SEQ ID NO 68
<211> LENGTH: 24
<212> TYPE: DNA
<213> ORGANISM: Artificial Sequence
<220> FEATURE:
<223> OTHER INFORMATION: SOX10 reverse primer

<400> SEQUENCE: 68
agggatgaga actccactaa gtcc							24

<210> SEQ ID NO 69
<211> LENGTH: 24
<212> TYPE: DNA
<213> ORGANISM: Artificial Sequence
<220> FEATURE:
<223> OTHER INFORMATION: SOX17 forward primer

<400> SEQUENCE: 69
tgtctgccac ttgaacagtt tggg                                          24

<210> SEQ ID NO 70
<211> LENGTH: 24
<212> TYPE: DNA
<213> ORGANISM: Artificial Sequence
<220> FEATURE:
<223> OTHER INFORMATION: SOX17 reverse primer

<400> SEQUENCE: 70
gtgtgacaga ggtactagta gagc                                          24

<210> SEQ ID NO 71
<211> LENGTH: 24
<212> TYPE: DNA
<213> ORGANISM: Artificial Sequence
<220> FEATURE:
<223> OTHER INFORMATION: SOX2 forward primer

<400> SEQUENCE: 71
gctgcaaaag agaacaccaa tccc                                          24

<210> SEQ ID NO 72
<211> LENGTH: 24
<212> TYPE: DNA
<213> ORGANISM: Artificial Sequence
<220> FEATURE:
<223> OTHER INFORMATION: SOX2 reverse primer

<400> SEQUENCE: 72
aaacttcctg caaagctcct accg                                          24

<210> SEQ ID NO 73
<211> LENGTH: 24
<212> TYPE: DNA
<213> ORGANISM: Artificial Sequence
<220> FEATURE:
<223> OTHER INFORMATION: TBX6 forward primer

<400> SEQUENCE: 73
tctttccatc gtgtcaagct cacc                                          24

<210> SEQ ID NO 74
<211> LENGTH: 24
<212> TYPE: DNA
<213> ORGANISM: Artificial Sequence
<220> FEATURE:
<223> OTHER INFORMATION: TBX6 reverse primer

<400> SEQUENCE: 74
ctcttacagt ttctgccgtt ctcc                                          24

<210> SEQ ID NO 75
<211> LENGTH: 24
<212> TYPE: DNA
<213> ORGANISM: Artificial Sequence
<220> FEATURE:

```
<223> OTHER INFORMATION: TBXT forward primer

<400> SEQUENCE: 75
actggattga cctactaggt accc                                              24

<210> SEQ ID NO 76
<211> LENGTH: 24
<212> TYPE: DNA
<213> ORGANISM: Artificial Sequence
<220> FEATURE:
<223> OTHER INFORMATION: TBXT reverse primer

<400> SEQUENCE: 76
tttttcaccg tcagtgaggt tggg                                              24
```

GENERATION OF HUMAN SPINAL CORD NEURAL STEM CELLS

RELATED APPLICATIONS

This application claims priority to U.S. Provisional Application No. 62/714,590 filed on Aug. 3, 2018; the entire content of which is incorporated herein by reference.

BACKGROUND

Worldwide, over 2.5 million people live with spinal cord injury, with over 100,000 new cases occurring annually. Spinal cord injury often causes motor dysfunction below the level of the injury. For example, thoracic and lumbar spinal cord injury can cause paraplegia and cervical spinal cord injury can cause quadriplegia. Such injury is permanent and often severe and there is no effective treatment. Various neurologic diseases also involve damaged or dysfunctional spinal cord neurons. Neural stem cell grafts have potential for treating such conditions. However, it has not been possible to obtain sufficient numbers of appropriately patterned neural stem cells, having a spinal cord positional identity, for implanted cells to survive and functionally engraft.

SUMMARY

Disclosed herein are methods of inducing and maintaining spinal cord neural stem cells (NSC) and spinal cord neural progenitor cells, staring with human pluripotent stem cells. In some embodiments the hPSC are human embryonic stem cells (hESC). In some embodiments the hPSC are induced pluripotent stem cells (iPSC).

Maintaining the spinal cord NSC includes expansion, that is, increasing their number. Maintaining the spinal cord NSC can include their differentiation into spinal cord neural progenitor cells. In some embodiments differentiation into spinal cord neural progenitor cells includes obtaining all three neuronal progenitor lineages: neuronal, astrocytic, and oligodendrocytic. Maintaining the spinal cord NSC includes retaining the spinal cord positional identity (patterning).

Inducing spinal cord NSC comprises culturing the cells in the presence of caudalizing morphogens (compounds causing development of spinal cord patterning, rather than, for example, brain patterning) and SMAD inhibitors (SMAD is an allusion to this family of proteins' homology with the *Caenorhabditis elegans* SMA ("small" worm phenotype) and *Drosophila* MAD ("Mothers Against Decapentaplegic") family of genes). Some embodiments use dual SMAD inhibitors. In some embodiments, the SMAD inhibitors are inhibitors of bone morphogenetic protein (BMP), activin, and transforming growth factor β (TGF-β). In some embodiments, the caudalizing morphogens are fibroblast growth factor 2 (FGF2) and FGF8 (FGF2/8), and an activator of WNT signaling. In some embodiments, the activator of WNT signaling is CHIR99021. In some embodiments, the inhibitor of BMP is LDN-19318. In some embodiments, the inhibitor of activin and TGF-β is SB-431542.

Maintaining spinal cord NSC comprises culturing the NSC in the presence of inhibitors of activin and TGF-β, and activators of WNT signaling, and sonic hedgehog signaling (SHH). In some embodiments, the inhibitor of activin and TGF-β is SB-431542. In some embodiments, the activator of WNT signaling is CHIR99021. In some embodiments, the activator of SHH is Hh-Ag1.5.

Some embodiments comprise a method of inducing spinal cord NSC. Some embodiments comprise a method maintaining spinal cord NSC. Some embodiments comprise an integrated method of inducing and maintaining spinal cord NSC.

Some embodiments comprise an ex vivo population of cells generated by the herein disclosed methods. Some embodiments comprise an ex vivo population of cells enriched in spinal cord NSC. Some embodiments comprise an ex vivo near-homogeneous population of spinal cord NSC (in the sense that the population is highly enriched for spinal cord NSC, but not that the NSC are all of the same kind). Some embodiments consist essentially of an ex vivo spinal cord NSC and spinal cord neuronal progenitor cells. Some embodiments predominantly comprise an ex vivo spinal cord neuronal progenitor cells. In aspects of these embodiments, the spinal cord neuronal progenitor cells comprise neural, astrocytic, and oligodendrocytic spinal cord progenitor cells. In further aspects, the neural spinal cord progenitor cells can comprise motor neuron and/or p3 progenitor cells, in further aspects the neural spinal cord progenitor cells can comprise dorsal and ventral spinal cord progenitor cells To be suitable for implantation with survival and engraftment, the various cellular compositions herein disclosed should comprise at least 50-200 million cells. Thus various embodiments are cell cultures and populations comprising at least 50 million, or 100 million, or 150 million, or 200 million cells. In some embodiments, the culture or population does not comprise more than 500 million or 750 million, or one billion cells.

BRIEF DESCRIPTIONS OF THE DRAWINGS

FIGS. 1A-L: Induction of Spinal Cord NSCs from H9 ES Cells. FIG. 1A) Schematic representation of the spinal cord neural induction protocol. (FIG. 1B) qPCR for pluripotent cell markers NANOG and OCT4, neural markers SOX1 and SOX2, mesodermal marker TBXT, and ectodermal marker PAX6, ten days after neural induction (n=3 for each gene, three independent experiments). Gene expression levels were normalized to expression in H9 ESCs for each gene. (FIGS. 1C,D) Immunolabeling for Brachurry (Bra or T), PAX6, and SOX2, three days after neural induction with (FIG. 1C) or (FIG. 1D) without CHIR and FGF2/8. PAX6 (FIG. 1C) or Bra (FIG. 1D)) staining is not included in the greyscale images to make them more interpretable; expression of these markers was not observed. Scale bars=20 µm. (FIG. 1E) qPCR for spinal cord markers CDX2 and HOX genes, ten days after neural induction (n=3 for each gene, three independent experiments). Gene expression levels were normalized to the expression of H9 ESCs for each gene. (FIG. 1F) Immunolabeling for SOX2, OCT4, and CDX2 ten days after induction. 90.1±3.1% of cells acquired a regional phenotype of the spinal cord (SOX2$^+$/CDX2$^+$). Scale bar=250 µm. Right panels show high magnification images of CDX2, SOX2, and OCT4. Scale bars=10 µm. OCT4 staining is included only in the lower right sub-panel to simplify interpretation of the greyscale images; OCT4 expression is not observed at this time point. Inset shows neural stem marker SOX2 and Nestin (Nes) expression, ten days after neural induction. Scale bar=10 µm. (FIG. 1G) Immunolabeling for SOX1, SOX2, and Nestin (Nes) at passage 15. SOX1 staining is not included to simplify interpretation of the greyscale images. Scale bar=50 µm. (FIG. 1H) qPCR for patterning genes in long term culture (>1 mo.). Default H9-NSCs do not express HOX genes, but H9 spinal cord NSCs persistently express HOX genes, indicating that induced NSCs maintain a spinal cord regional identity over prolonged passages (n=3 independent experiments). For each gene, expression levels were normalized to the sample with the highest level of expression (which was set at a value of 1.0). (FIG. 1I) Gene expression in induced cells, two months after neural induction was compared to that of human fetal brain and spinal cord by qPCR (n=3 independent experiments). For each gene, expression levels were normalized to fetal whole brain or spinal cord samples exhibiting the highest level of expression (which was set at a value of 1.0). (FIG. 1J) Immunolabeling for the neuronal markers NeuN, Hu, and TUJ1, ten weeks after neuronal differentiation. NeuN staining is not included to simplify interpretation of the greyscale images. Scale bar=100 µm. (FIGS. 1K,L) Phase contrast image of a patched neuron and corresponding traces of evoked action potentials (whole-cell recording, current-clamp mode) in neurons (FIG. 1K) and traces of spontaneous excitatory postsynaptic currents (FIG. 1L) ten weeks after neuronal differentiation. Scale bars=20 um. Data are presented as mean±SEM. Immunocytochemistry was independently repeated at least three times by two independent observers with similar results (FIGS. 11C,D,F, and G) and twice for FIG. 1J.

Figure 2C:
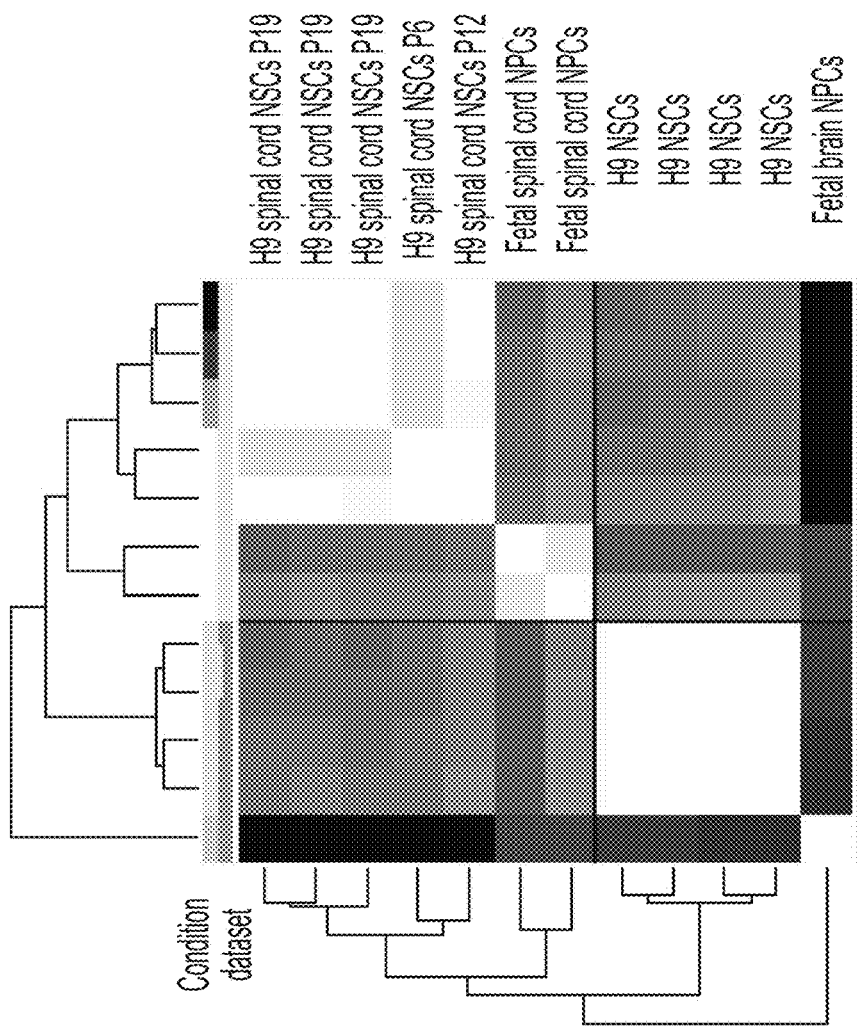
Figure 2B:
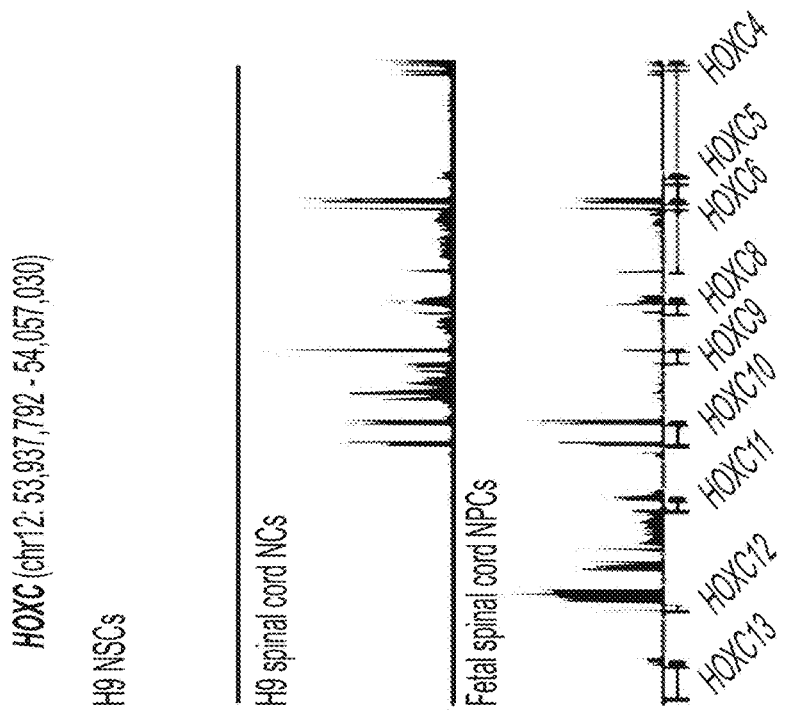

FIGS. 2A-C: RNA-Sequencing of H9-Derived Spinal Cord NSCs. (FIG. 2A) mRNA expression of HOXA and HOXB clusters in each sample by RNA-Sequencing. For each gene, expression levels were normalized to the cell sample with the highest level (=100), and the values have been color-coded as shown. (FIG. 2B) Transcriptional activities of HOXC cluster in default (brain fate) H9-NSCs, H9-derived spinal cord NSCs, and fetal spinal cord-derived NPCs. H9-derived spinal cord NSCs clearly express spinal cord-specific HOX genes. (FIG. 2C) Hierarchical clustering analysis on four human NSC lines (H9-derived spinal cord NSCs, default H9-NSCs, fetal brain- and spinal cord-derived NPCs) classified two major clusters, with H9-derived spinal cord NSCs exhibiting gene expression profiles more closely related to fetal spinal cord-derived NPCs, but not fetal brain-derived NPCs.

FIGS. 3A-P: Survival, Differentiation, and Axonal Extension of H9-Derived Spinal Cord NSCs in Sites of Spinal Cord Injury. (FIGS. 3A,B) GFP immunolabeling in spinal cord sagittal section reveal that GFP-expressing H9-derived spinal cord NSC grafts robustly extend axons into the host spinal cord rostral and caudal to the C4 dorsal column SCI site (caudal shown), three months post-grafting. Axonal entry into gray matter (GM) from white matter (WM) is evident in FIG. 3B. Inset shows that GFP-labeled projections arising from grafts express the human-specific axonal marker neurofilament70 (NF70), confirming their identity as axons. CAMKII and ChAT staining is not included to simplify interpretation of the greyscale image. Scale bars=1 mm (FIG. 3A) and 200 µm (FIG. 3B). (FIG. 3C) Confocal image of graft center, six weeks post-grafting, reveals that grafted cells express the neuronal markers DCX and NeuN. Scar bar=10 µm. (FIGS. 3D-F) Confocal images three months post-grafting show the human-specific nuclear marker, HuNu, co-localizing with the neuronal marker TUJ1 (FIG. 3D), the astrocyte marker GFAP (human specific, FIG. 3E), and the oligodendrocyte progenitor cell marker human NG2 (hNG2, FIG. 3F). Scale bars=100 um (FIG. 3D), 10 um (FIG. 3E), and 5 um (FIG. 3F). (FIG. 3G) Migrating GFP-expressing cells differentiate into APC-expressing mature oligodendrocytes, six months post-grafting. GFAP staining is not included to simplify interpretation of the greyscale image. Scale bar=20 µm. (FIGS. 3H-K) Confocal images of graft-derived cells, six months post-grafting. HuNu$^+$ human cells express neuronal subtype markers (FIG. 3H) CaMKII, (FIG. 3I) ChAT, (FIG. 3J) GABA, or (FIG. 3K) GlyT2 showing that the graft differentiates into four spinal cord neuronal subtypes. Z-stack images for FIGS. 3E,F,H-K not shown. Scale bars=20 µm. (FIG. 3L) Quantification of graft-derived neuronal subtypes shows that the majority of grafted neurons differentiate into CaMKII-expressing excitatory neurons six months post-grafting (n=3). (FIGS. 3M-O) Confocal images of transverse sections of host spinal cords at (FIG. 3M) C2 or (FIG. 3N) C8 level. Grafts extend very large numbers of axons directly into the host spinal cord that co-localize with human-specific axonal TAU (hTAU). DC; dorsal column. COMET expression (RFP staining for CST) is not included in m and n to simplify interpretation of the greyscale images. Scale bars=200 um (FIGS. 3M,N). (FIG. 3O) Immunolabeling for GFP, CaMKII, and human synaptophysin (hSYN) in transverse section at C8. Dotted line indicates boundary between host dorsal column (DC) and host gray matter. CaMKII staining is not depicted to simplify interpretation of the greyscale image. Scale bar=50 µm. (FIG. 3P) Electron microscopy shows that DAB-labeled GFP-expressing human axon terminals (G) form synapses (arrowheads) with host dendrites. Scale bar=400 nm. Data are presented as mean±SEM. Immunohistochemistry was independently repeated at least twice with similar results.

Figure 4F:
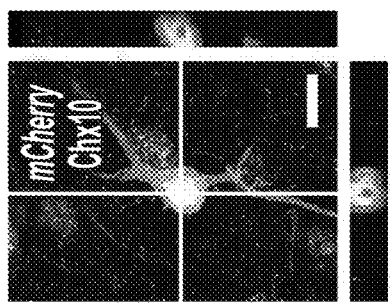
Figure 4G:
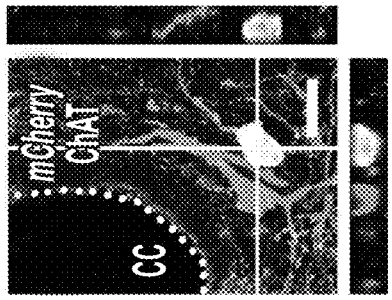
Figure 4H:
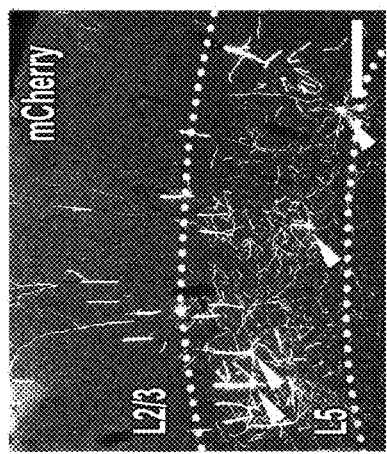
Figure 4I:
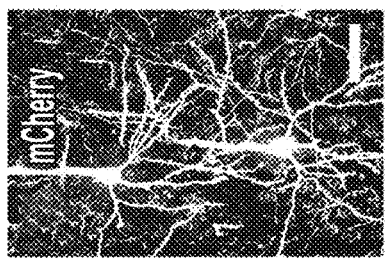

FIGS. 4A-M: Graft-Initiated Trans-Synaptic Rabies Virus Retrograde Labeling of Host Connectivity. (FIGS. 4A,B) Sagittal sections showing retrogradely, trans-synaptically traced host mCherry-expressing cells in the cervical spinal cord caudal to the C4 lesion site. Host neurons only express mCherry if they are synaptically connected with the grafted human spinal cord neurons. Numerous connected host neurons are scattered throughout gray matter. Scale bar=500 µm. Inset shows high magnification of boxed area. Scale bar=100 um. (FIG. 4C) mCherry$^+$/HuNu$^-$ host neurons synaptically connected to graft are present in the host spinal cord surrounding grafts. Scale bar=50 µm. (FIGS. 4E-F) Transverse sections labeled for mCherry and NeuN at C2 (FIG. 4D), T2 (FIG. 4E), and L2 (FIG. 4F) host spinal cord level, showing that host neurons mono-synaptically connected to grafts are detected over long lengths of the rat spinal cord. At the lumbar level, a trans-synaptically labeled cell is present in lamina VII (boxed area). Inset shows high magnification of boxed area. Scale bars=400 um (FIGS. 4D,F) and 200 µm (FIG. 4E). (FIGS. 4F-J) Characterization of mCherry$^+$ host cells in the cervical spinal cord. Synaptically connected mCherry$^+$ host neurons include (FIG. 4F) CHX10$^+$ V2a interneurons and (FIG. 4G) ChAT$^+$ V0c interneurons. Scale bars=20 µm. (FIGS. 4H,I) Traced neurons (arrowheads) in frontal motor cortex (layer V, FIG. 4H) display a classical pyramidal cell morphology (FIG. 4I). Scale bars=250 µm (FIG. 4H) and 50 µm (FIG. 4I). L2/3; Layer L5; Layer V. (FIG. 4J) 5-HT$^+$ serotonergic neurons in caudal raphe magnus nucleus (RMg) are synaptically connected to human NSC graft. NeuN staining is not included to simplify interpretation of the greyscale image. Scale bar=40 µm. (FIG. 4K) In the reticular formation, host neurons in the gigantocellular reticular nucleus (Gi) are synaptically connected to the human graft. Arrowheads indicate trans-synaptically labeled cells are shown in insets. PY; pyramidal tract. Scale bar=250 µm. (FIG. 4L) In the reticular formation, host neurons in the medullary reticular nucleus ventral part (MdV) and medullary reticular nucleus dorsal part (MdD) are synaptically connected to the human graft. Arrowheads indicate trans-synaptically labeled cells are shown in insets. CVL; caudoventrolateral reticular nucleus, LRt; lateral reticular nucleus. Scale bar=250 µm. (FIG. 4M) Trans-synaptically labeled mCherry+ host neurons in the lateral vestibular nucleus (LVe). Scale bars=50 µm (FIG. 4D). V4; fourth ventricle, MVeP, medial vestibular nucleus parvocellular part, MVeM; medial vestibular nucleus magnocellular part. Immunohistochemistry was independently repeated at least twice with similar results.

Figure 5J:
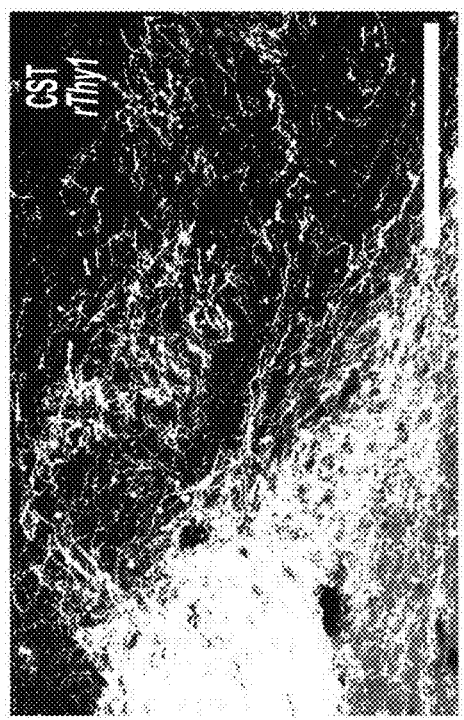
Figure 5I:
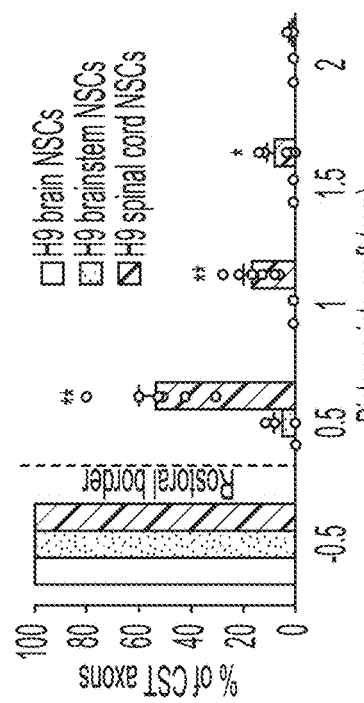
Figure 5M:
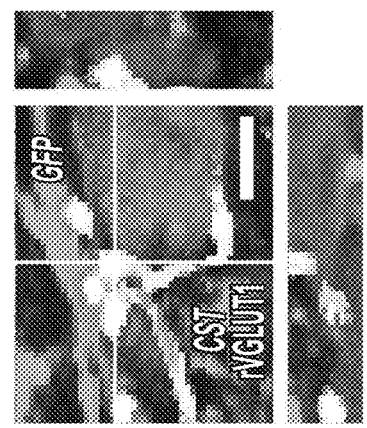
Figure 5L:
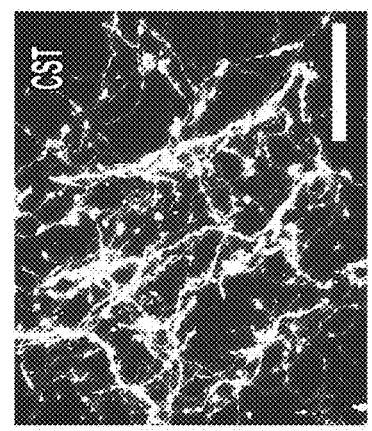
Figure 5K:
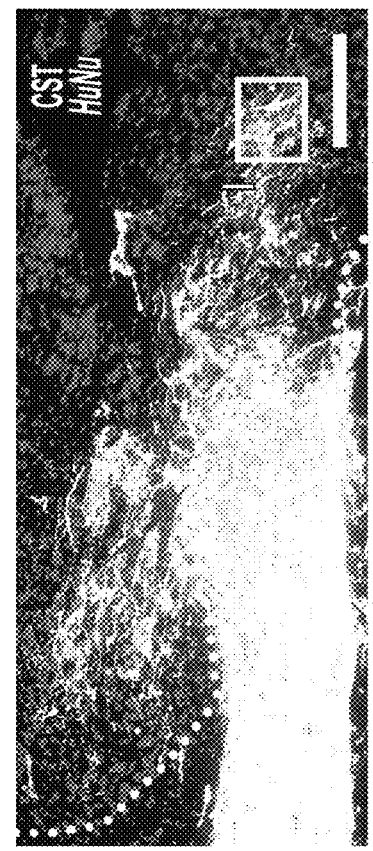
Figure 6A:
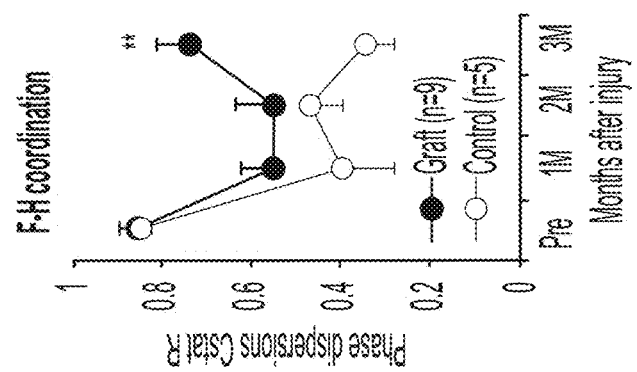
Figure 6B:
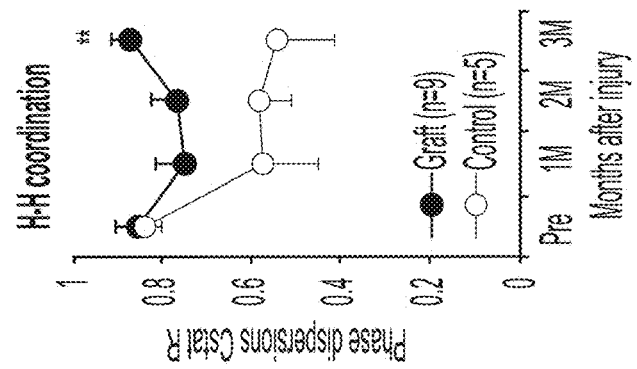
Figure 6C:
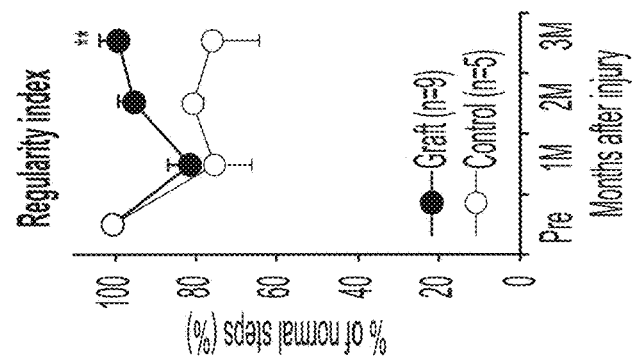
Figure 6D:
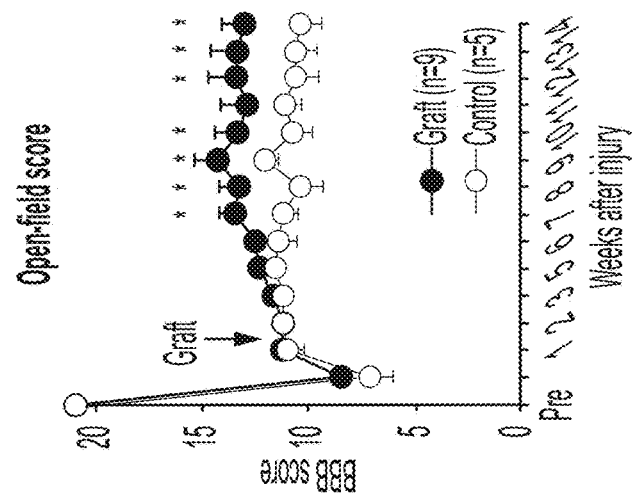

FIGS. 5A-M: Robust Corticospinal Regeneration into H9-Derived Spinal Cord NSC Grafts. (FIG. 5A) Gene expression by qPCR of H9-derived brain, brainstem, and spinal cord NSCs, nine days after neural induction (n=3). Gene expression was normalized to the highest expressing sample (which was set at a value of 1.0). (FIG. 5B) Gene expression of H9-derived cells at 15 passages by qPCR, showing that NSCs maintain their rostro-caudal regional identity (n=3). Gene expression was normalized to the highest gene expressing sample (which was set at a value of 1.0). (FIG. 5-H) Sagittal views of H9-derived NSC grafts of either brain (top row; FIGS. 5C,F), brainstem (middle row; FIGS. 5D,G), or spinal cord (bottom row; FIG. 5E,H) identity. Grafts were placed into C4-corticospinal lesion sites. Corticospinal axonal regeneration occurs into spinal cord NSCs, but not brain NSCs. Scale bars=100 µm. (FIG. 5) Quantification of the proportion of corticospinal axons in NSC grafts, normalized to the total number of corticospinal axons located 0.5 mm rostral to the lesion site. n=4 brain-NSC recipients, n=5 brainstem-NSC recipients, and n=6 spinal cord-NSC recipients. One-way ANOVA (+0.5 mm; $F(2,12)=37.2$, $P<0.001$.+1.0 mm; $F(2,12)=16.6$, $P=0.013$.+1.5 mm; $F(2,12)=6.0$, $P=0.016$) with Tukey's multiple comparisons; *$P<0.05$, **$P<0.01$ to H9 brain and brainstem NSCs. (FIG. 5J) Robust corticospinal regeneration (CST) into human neural stem cell graft in the lesion site, two months post-transplantation. Host (rat) neural gray matter is labeled with rat Thy1 (rThy1), which is absent from the lesion site, clearly establishing that host CST axons are migrating into the graft. Scale bars=250 µm. (FIGS. 5K-M) Sagittal views of corticospinal axons and HuNu+ H9-spinal cord NSC grafts. Dashed lines in FIG. 5K indicate rostral host-graft border. Right image (FIG. 5L) is high-magnification view of boxed area in FIG. 5K. Scale bars=250 µm (FIG. 5K) and 50 µm (FIG. 5L). (FIG. 5M) Triple labeling for GFP, corticospinal axons, and rat VGLUT1 reveals co-localization of regenerating corticospinal axon terminals with rat VGLUT1, suggesting synaptic connectivity. Scale bar=5 µm. Data are presented as mean±SEM. Corticospinal tracing experiments were independently repeated twice with similar results.

FIGS. 6A-D: Significant Functional Improvement after Contusive SCI. (FIG. 6A) Hindlimb locomotion: Significant improvements in BBB scores after grafts of H9-scNSCs (grafted animals n=9, control animals n=5). Two-way repeated measures ANOVA, $P<0.0001$, $F (1, 180)=31.3$; post hoc Fischer's *$P<0.05$ on weeks 7-10, 12-14. $P=0.040$ (week 7), 0.011 (week 8), 0.047 (week 9), 0.021 (week 10), 0.013 (week 12), 0.013 (week 13), and 0.018 (week 14). (FIGS. 6B-D) Catwalk automated quantitative gait analysis: % of normal steps (regularity index (RI)), hindlimb-hindlimb (H-H) coordination, and forelimb-hindlimb (F-H) coordination significantly improve in grafted animals (n=9) compared to controls (n=5), three months post-grafting. Two-way repeated measures ANOVA (RI; $F (1, 12)=5.7$, $P=0.035$. H-H coordination; $F (1, 12)=7.8$, $P=0.002$. F-H coordination; $F (1, 12)=5.3$, $P=0.001$); post hoc Fischer's **$P<0.01$. $P=0.0065$ (RI), 0.0023 (H-H coordination), and 0.0009 (F-H coordination). Data are presented as mean±SEM.

Figure 7S:
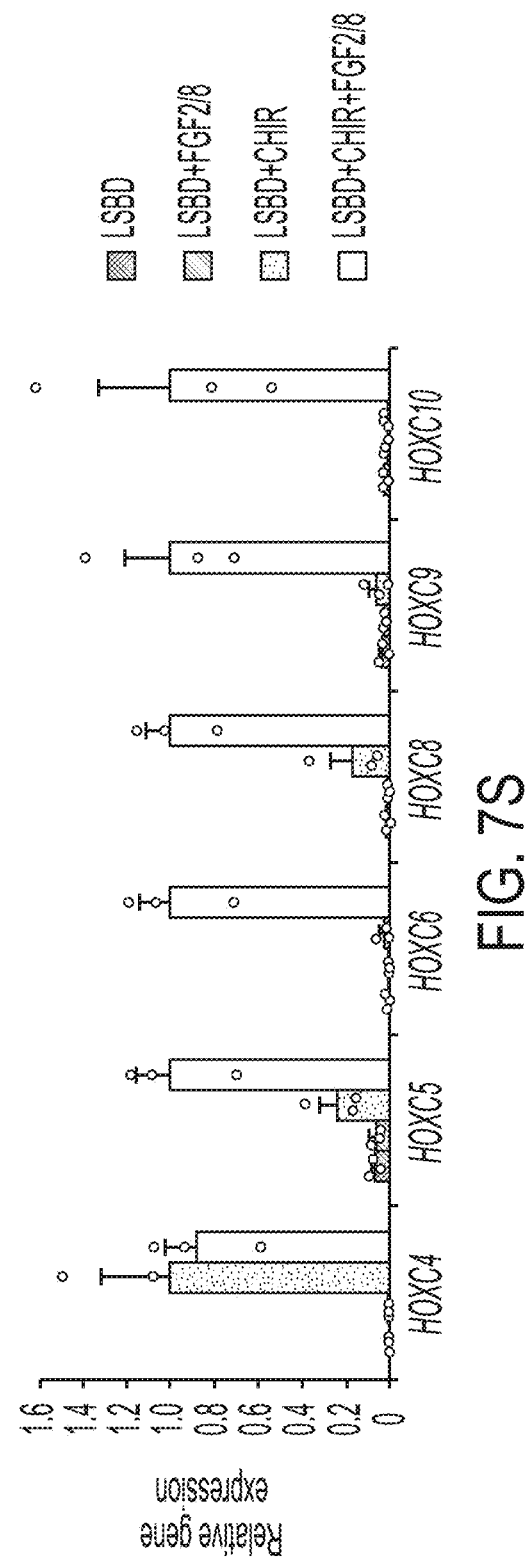

FIGS. 7A-S: Induction of Spinal Cord NSCs from H9 ES Cells. (FIGS. 7A,B) Immunolabeling for SOX2, CDX2, and PAX6 (FIG. 7A; without CHIR+FGF2/8, FIG. 7B; with CHIR+FGF2/8), ten days after neural induction. SOX2 staining is not included to simplify interpretation of the greyscale images. Scale bars=100 um. (FIGS. 7C,D) qPCR for (FIG. 7C) forebrain markers FOXG1, OTX2, IRX3, and SIX3 and hindbrain markers EGR2 (KROX20) and MAFB, and (FIG. 7D) mesodermal markers TBX6, FOXC1, and MEOX1, endodermal marker SOX17, and neural crest cell markers FOXD3, SNAI1 (SNAIL), and SOX/0, ten days after neural induction (n=3 for each gene, three independent experiments). (FIGS. 7E,F) Immunolabeling for FOXG1, Nestin (Nes), and SOX2 (FIG. 7E; without CHIR+FGF2/8, FIG. 7F; with CHIR+FGF2/8), ten days after neural induction, indicating CHIR and FGF2/8 treated cells do not express FOXG1 and do not form neural rosettes. SOX2 staining is not included to simplify interpretation of the greyscale images. Scale bars=100 µm. (FIGS. 7G-J) Immunolabeling for Brachyury (Bra) (FIG. 7G; LDN+SB+ DAPT (LSBD), FIG. 7H; LSBD+FGF2/8, FIG. 7I; LSBD+CHIR, FIG. 7J; LSBD+CHIR+FGF2/8) four days after neural induction (P0). Scale bars=100 um. (FIGS. 7K-N) Immunolabeling for brain markers OTX2 and PAX6, four days after neural induction (P0, FIG. 7K; LSBD, FIG. 7L; LSBD+FGF2/8, FIG. 7M; LSBD+CHIR, FIG. 7N; LSBD+CHIR+FGF2/8). Scale bars=100 um. (FIGS. 7O-R) Immunolabeling for CDX2 and PAX6 (FIG. 7O; LSBD, FIG. 7P; LSBD+FGF2/8, FIG. 7Q; LSBD+CHIR, FIG. 7R; LSBD+CHIR+FGF2/8), eight days after neural induction. DAPI staining is not included in g-r to simplify interpretation of the greyscale images. Scale bars=100 um. (FIG. 7S) HOX C gene expression nine days after neural induction (n=3). Spinal cord-specific HOXC 6-10 expression was dramatically up-regulated in the LSBD+CHIR+FGF2/8 condition. Each gene expression was normalized to the highest gene expressing sample (which was set at a value of 1.0). Data are presented as mean±SEM. Immunocytochemistry was independently repeated at least three times with similar results.

FIGS. 8A-S: Purity of H9-Derived Spinal Cord NSCs. (FIGS. 8A-H) Immunolabeling for the neural stem cell marker SOX2 and mesodermal stem cell marker TBX6 (FIGS. 8A,E; CHIR+FGF2/8, FIGS. 8B,F; CHIR+FGF2/8+ DAPT, FIGS. 8C,G; CHIR+FGF2/8+LDN+SB (LSB), FIGS. 8D,H; CHIR+FGF2/8+LSB+DAPT), three days (P0, FIGS. 8A-D) and four days (P1, FIGS. 8E-H) after neural induction. Scale bars=100 um. (FIGS. 8I-L) Immunolabeling for CDX2 and DAPI (FIG. 8I; CHIR+FGF2/8, FIG. 8J; CHIR+FGF2/8+DAPT, FIG. 8K; CHIR+FGF2/8+LSB, FIG. 8L; CHIR+FGF2/8+LSB+DAPT), eight days after neural induction. Scale bars=100 urn. (FIGS. 8M-O) Quantification in FIGS. 8E-H (FIG. 8M, n=4 for each group, four independent experiments) and FIGS. 8I-L (FIGS. 8N,O, n=4 for each group, four independent experiments). Two-way ANOVA ((m) $F(3,12)=19.6$, $P<0.0001$. (n) $F(3,12)=5.5$, $P=0.0129$. (o) $F(3,12)=6.2$, $P=0.0089$), followed by Tukey's multiple comparisons. *$P<0.05$; $P<0.01$, *$P<0.001$. (FIGS. 8P-S) Immunolabeling for the definitive endodermal marker CXCR4, four days neural induction (P0, p; CHIR+ FGF2/8, CHIR+FGF2/8+DAPT, r; CHIR+FGF2/8+LSB, CHIR+FGF2/8+LSB+DAPT). Scale bars=100 um. LSB blocked mesodermal and endodermal induction. DAPI staining is not included in FIGS. 8A-L, FIGS. 8P-S to make them more interpretable. Data are presented as mean±SEM.

Immunocytochemistry was independently repeated four times with similar results for FIGS. 8A-L and twice for FIGS. 8P-S.

Figure 9C:
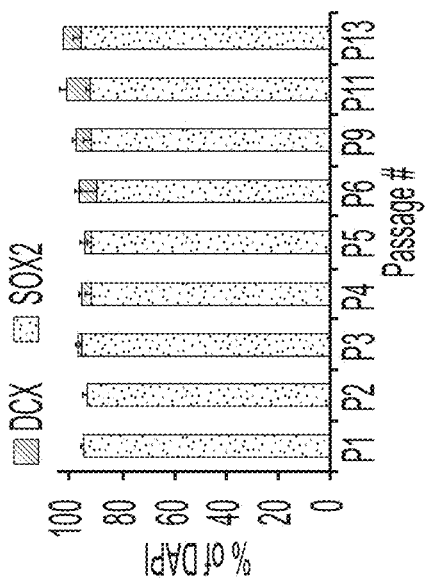
Figure 9B:
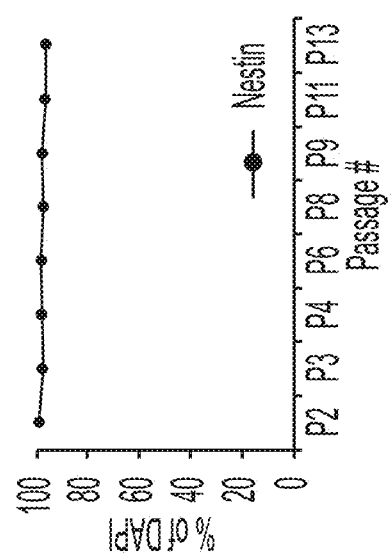
Figure 9F:
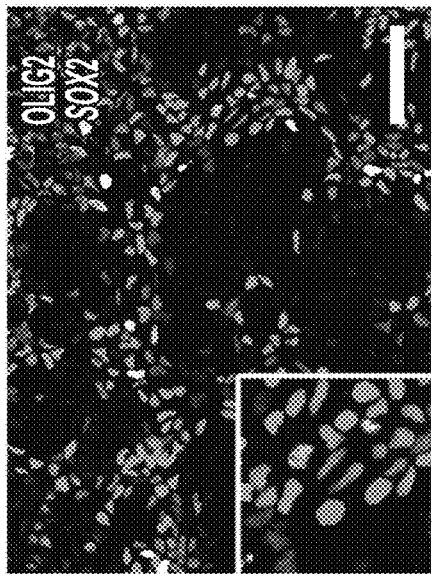
Figure 9E:
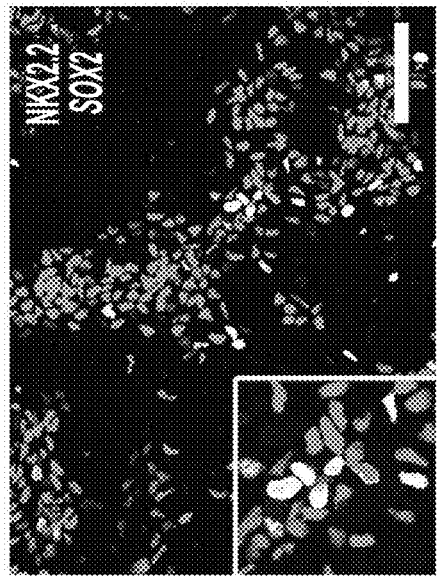

FIGS. 9A-L: Rostro-Caudal and Dorso-Ventral Axis of H9-Derived Spinal Cord NSCs. (FIG. 9A) Immunolabeling for the post-mitotic neuronal marker DCX, the neural intermediate filament Nestin (Nes), and mitotic NSC marker SOX2 at P18. DCX and DAPI staining is not included to simplify interpretation of the greyscale image. Scale bar=100 um. (FIGS. 9B,C) Temporal analysis of proportion of Nestin-expressing cells (FIG. 9B) and SOX2- or DCX-expressing cells (FIG. 9C). Almost all cells expressed Nestin, DCX, and/or SOX2 at each passage. Data were normalized to the number of DAPI+ cells (n=3). (FIGS. 9D-F) Immunolabeling for dorsal (PAX6) and ventral (NKX6.1) markers (FIG. 9D), p3 marker NKX2.2 (FIG. 9E), or pMN marker OLIG2 (FIG. 9F) with NSC marker SOX2, 20 days after neural induction. SOX2 staining in d is not included to simplify interpretation of the greyscale image. Scale bars=100 µm. (FIGS. 9G,H) Immunolabeling for NKX6.1, PAX6, and SOX2 18 days after neural induction. Insets show the higher magnification images. SOX2 staining is not included to simplify interpretation of the greyscale images. Hg-Ag1.5 (SHH) disrupted dorsal-ventral polarity of induced cells. Scale bars=100 µm. (FIG. 9I) Temporal analysis of dorso-ventral axis of H9-derived spinal cord NSCs. The number of PAX6 or NKX6.1 expressing cells were normalized to the number of SOX2-expressing cells (n=3). (FIGS. 9J-L) qPCR for HOXA (FIG. 9J), HOXB (FIG. 9K), and HOXC (FIG. 9L) genes. Gene expression was normalized to the time point of maximum expression in each gene (n=3). HOX genes were sequentially activated after neural induction. Data are presented as mean±SEM. Immunocytochemistry was independently repeated at least three times (FIG. 9A, D-F) or twice (FIGS. 9G,H) with similar results.

FIGS. 10A-Z: Differentiation of H9-derived spinal cord NSCs. (FIG. 10A) Representative traces of spontaneous activity (left panels) and action potentials (right panels). 250 nM and 1 µM TTX blocked spontaneous activity and action potentials. (FIG. 10B) Representative traces of spontaneous postsynaptic currents in the presence or absence of the glutamate receptor antagonists DNQX and APV, and the GABA-A receptor antagonist picrotoxin (PTX). There was no change in spiking of this neuron after all three drugs, suggesting that changes in spontaneous activity result from inputs onto the cell. (FIGS. 10C,D) Ten weeks after neuronal differentiation, cells differentiated into Hu-expressing neurons (FIG. 10C) and GFAP-expressing astrocytes (FIG. 10D). NeuN (FIG. 10C) and S100b (FIG. 10D) staining is not included to simplify interpretation of the greyscale images. Scale bars=100 µm. (FIGS. 10E-G) Immunolabeling for neuronal markers (MAP2, DCX, or TUJ1) and neurotransmitter phenotype markers, eight weeks after neuronal differentiation, showing that these cells have the potential to differentiate into glutamatergic (glutamate (Glu); FIG. 10E), GABAergic (GABA; FIG. 10F), and glycinergic (GlyT2, FIG. 10G) neurons. Scale bars=50 µm. (FIGS. 10H-Q) Immunolabeling for neuronal marker DCX and transcription factors that specify neuronal subtypes, including HB9 (FIG. 10H), ISL1/2 (FIG. 10I), LIM 1+2 (FIG. 10J), BRN3A (FIG. 10K), TLX3 (FIG. 10L), LBX1 (FIG. 10M), CHX10 (FIG. 10N), LHX3 (FIG. 10O), and PAX2 (FIG. 10P) two weeks after neuronal differentiation. Scale bars=40 µm. (FIGS. 10Q-Z) Clonal analysis of H9-derived spinal cord NSCs. Single GFP-expressing H9-derived spinal cord NSC was expanded on GFP negative H9-derived spinal cord NSCs and then purified by a flow cytometry. These subclones differentiated into GFAP-expressing astrocytes (FIG. 10Q) and DCX (FIG. 10R) or TUJ1 (FIG. 10S) -expressing neurons. These neurons included HB9 (FIG. 10T) or ISL1/2 (FIG. 10U) -expressing motor neurons and LIM1+2-expressing spinal interneurons (FIG. 10V). These interneurons are further characterized and included CHX10 (FIG. 10W) or LHX3 (FIG. 10X) -expressing excitatory interneurons and PAX2 (FIG. 10Y) or FOXP2 (FIG. 10Z) -expressing inhibitory interneurons. DCX staining is not included in t-z to simplify interpretation of the greyscale images. Scale bars=40 um (FIGS. 10Q, T) and 60 um (FIGS. 10R,S). Immunocytochemistry was independently repeated at least twice with similar results.

Figure 11A:
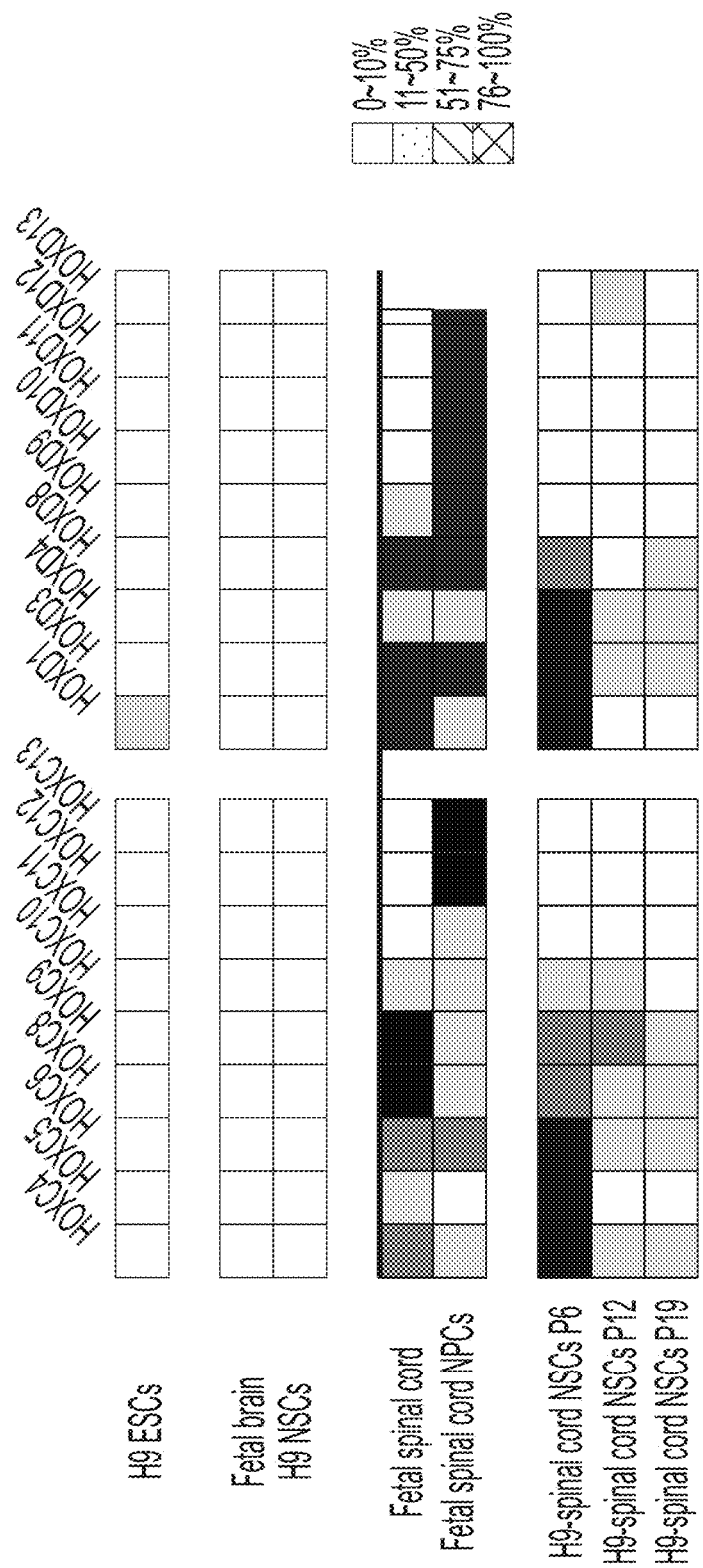
Figure 11I:
Figure 11J:
Figure 11H:
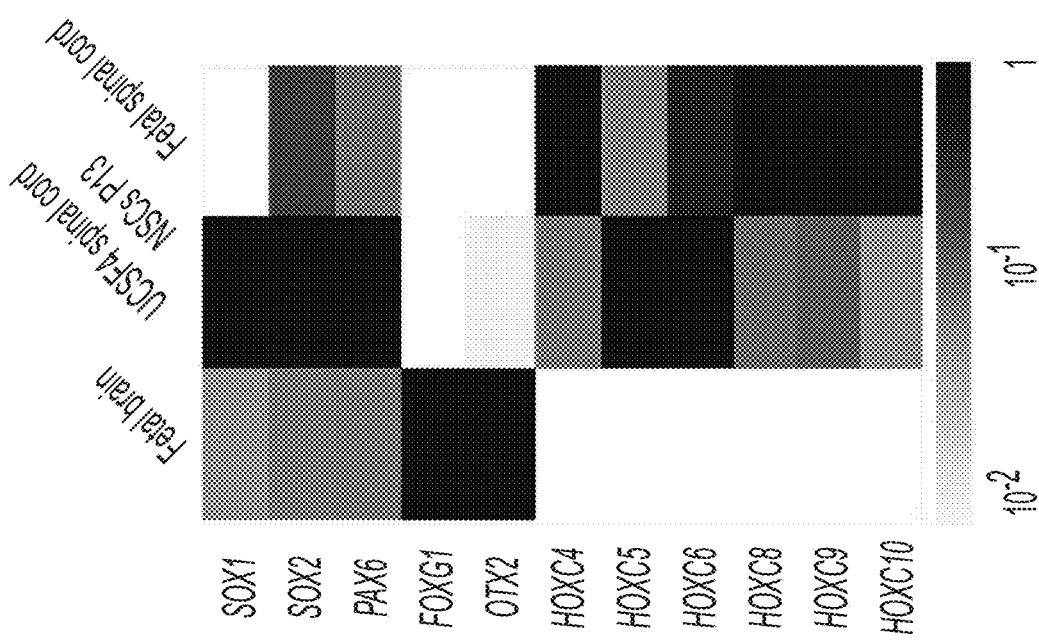
Figure 11K:
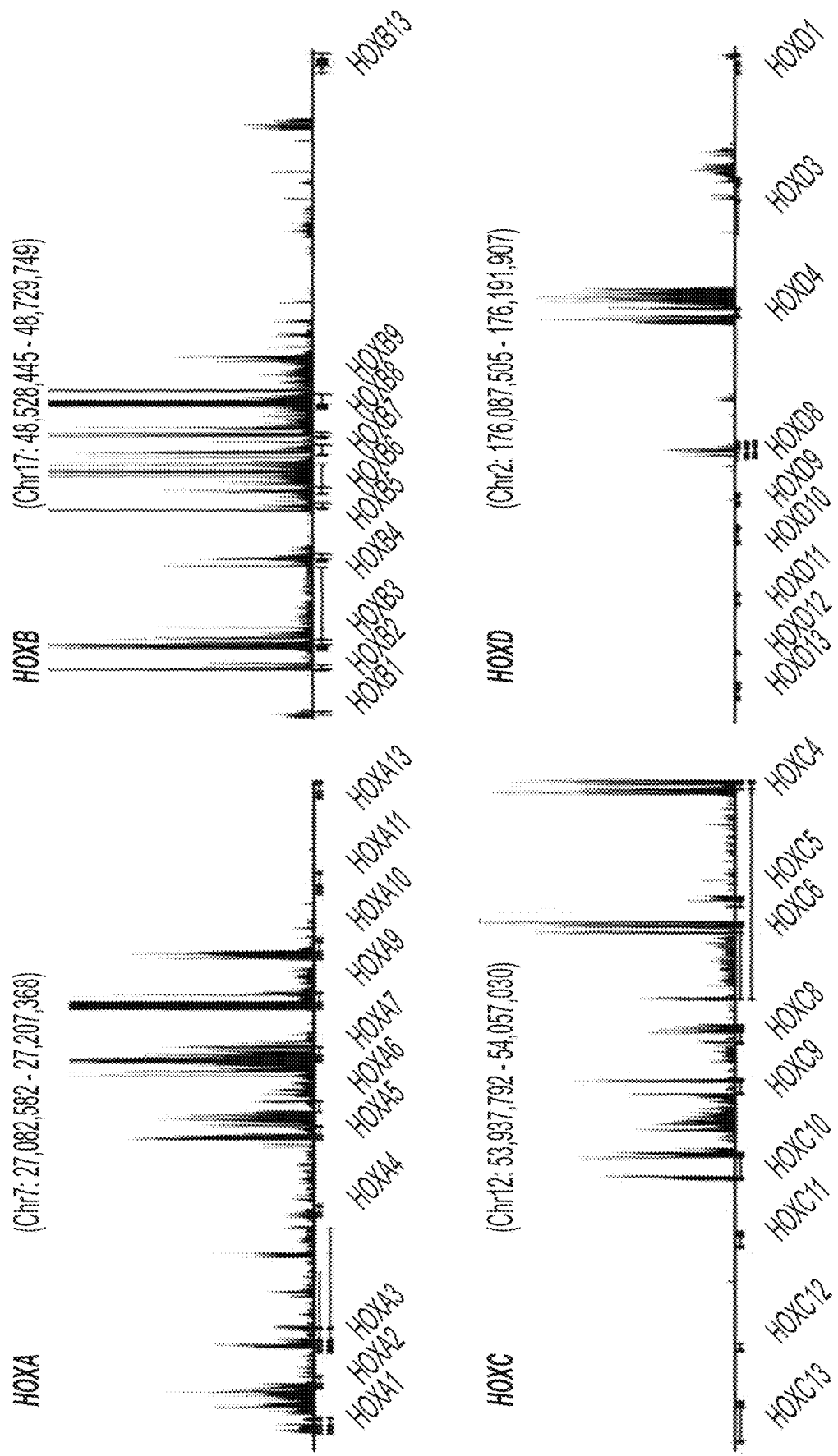

FIGS. 11A-K: UCSF4 ESC-Derived Spinal Cord NSCs. (FIG. 11A) mRNA expression of HOXC and HOXD clusters in each sample by RNA-Sequencing. Expression levels were normalized to the cell sample with the highest level (=100). (FIG. 11B) Transcriptional profiles of HOXD cluster genes in default H9-NSCs, H9-derived spinal cord NSCs, and fetal spinal cord-derived NPCs, clearly showing that H9-derived spinal cord NSCs express spinal cord-specific HOXD genes. (FIGS. 11C-E) Immunolabeling of UCSF4-derived spinal cord NSCs for CDX2, OCT4, and SOX2 (FIG. 11C, CDX2, PAX6, and SOX2 (FIG. 11D), and SOX2, FOXG1, and Nestin (Nes, FIG. 11E), ten days after neural induction. SOX2 (FIGS. 11C,D) or Nes (FIG. 11E) staining is not included to simplify interpretation of the greyscale images. Scale bars=250 µm (FIG. 11C) and 100 um (FIGS. 11D,E). (FIGS. 11G-G) qPCR for pluripotent cell markers NANOG and OCT4, neural markers SOX1 and SOX2, brain marker OTX2 and FOXG1, neural crest marker FOXD (FIG. 11F), and CDX2 and HOX genes (FIG. 11G) showing collinear HOX gene activation (n=3). Gene expression levels were normalized to expression in UCSF4 ESCs for each gene. (FIG. 11H Gene expression of fetal CNS tissues and UCSF4-derived spinal cord NSCs at passage 13 (n=3). Each gene expression was normalized to the sample with the highest expression level (=1). (FIG. 11I) Immunolabeling for neural marker SOX1, SOX2 and Nestin (Nes) at passage 12, indicating that long-term cultured UCSF4-derived cells maintain their neural identity. SOX1 staining is not included to simplify interpretation of the greyscale image. Scale bar=100 µm. (FIG. 11J) Immunolabeling for the neuronal marker MAP2 and astrocyte marker GFAP, five weeks after differentiation. DAPI staining is not included to simplify interpretation of the greyscale image. Scale bar=100 µm. (FIG. 11K) Transcriptional activities of HOXA-D clusters in UCSF4-derived spinal cord NSCs (passage 8). Data are presented as mean±SEM. Immunocytochemistry was independently repeated twice with similar results.

Figure 12K:
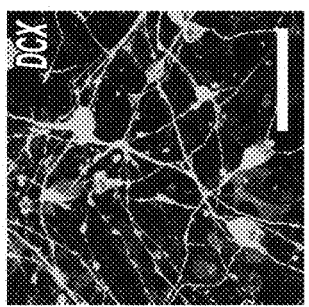
Figure 12P:
Figure 12J:
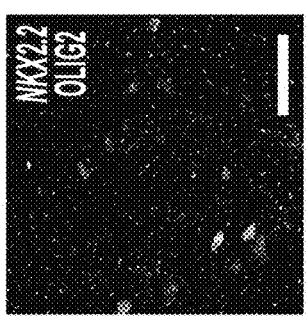
Figure 12O:
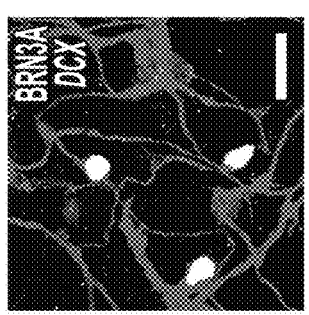
Figure 12S:
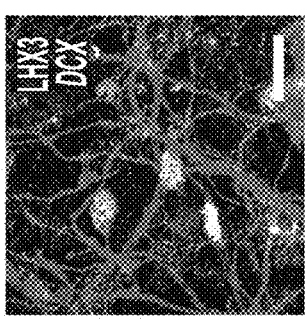
Figure 12I:
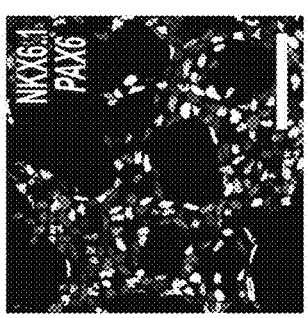
Figure 12N:
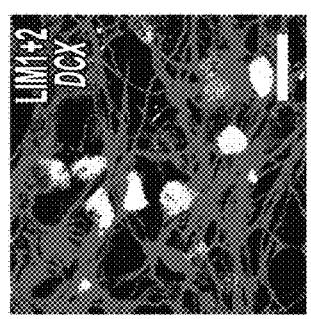
Figure 12R:
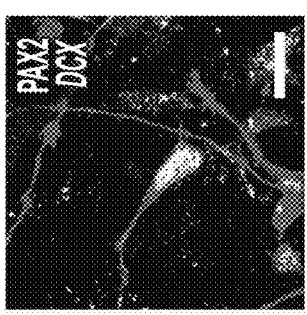
Figure 12H:
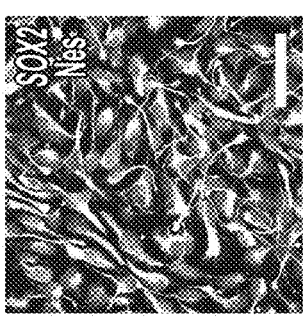
Figure 12M:
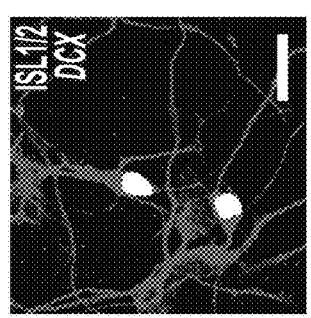
Figure 12Q:
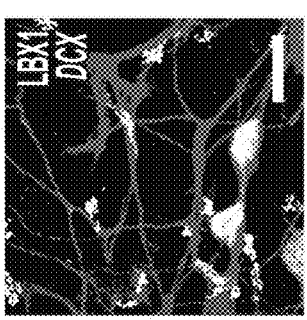
Figure 12G:
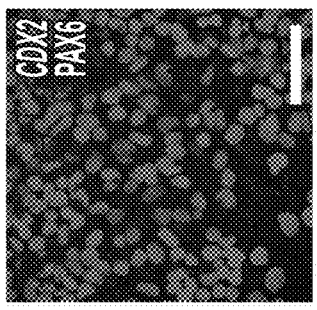
Figure 12L:
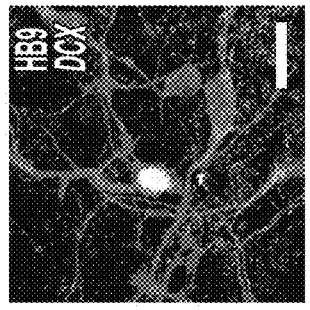

FIGS. 12A-S: Induction of Spinal Cord NSCs from human iPSCs. (FIGS. 12A-D) Immunolabeling of IPS11-derived spinal cord NSCs for Brachyury (Bra, FIG. 12A), PAX6 (FIG. 12B), and SOX2 (FIG. 12C), three days after neural induction. Co-localization of Bra and SOX2 are shown in FIG. 12D. Scale bars=20 µm. (FIG. 12E,F) qPCR of IPS11-derived cells for pluripotent cell markers NANOG and OCT4, neural markers SOX1 and SOX2, mesodermal marker T (TBXT), and ectodermal marker PAX6 (FIG. 12E), and spinal cord marker CDX2 and HOXC genes (FIG. 12F, n=3). Gene expression levels were normalized to expression in H9 ESCs for each gene. (FIG. 12G) Immunolabeling for CDX2, SOX2, and PAX6 nine days after induction. SOX2 staining is not included to simplify interpretation of the greyscale image. Scale bar=50 µm. (FIG. 12H) Immunolabeling for SOX2, SOX1, and Nestin (Nes) in passage 12 IPS11-derived spinal cord NSCs. SOX1 staining is not included to simplify interpretation of the greyscale image. Scale bar=50 μm. (FIGS. 12I,J) Triple immunolabeling for NKX6.1, PAX6 and SOX2 (FIG. 12I) and NKX2.2, OLIG2, and SOX2 (FIG. 12J), 18 days after neural induction. SOX2 staining is not included. Scale bar=100 μm (FIG. 12I) and 50 um (FIG. 12J). (FIG. 12K) Immunolabeling for the neuronal markers DCX and MAP2 in passage 15 IPS11-derived NSCs after ten days of neuronal differentiation, suggesting that they maintain their neuronal identity over several passages. MAP2 staining is not included to simplify interpretation of the greyscale image. Scale bar=50 um. (FIGS. 12L-S) Immunolabeling for DCX and transcription factors that specify neuronal subtypes, including HB9 (FIG. 12L), ISL1/2 (FIG. 12M), LIM1+2 (FIG. 12N), BRN3A (FIG. 12O), TLX3 (FIG. 12P), LBX1 (FIG. 12Q), PAX2 (FIG. 12R), and LHX3 (FIG. 12S), two weeks after neuronal differentiation. Scale bar=20 um. Data are presented as mean±SEM. Immunocytochemistry was independently repeated at least twice with similar results.

Figure 13D:
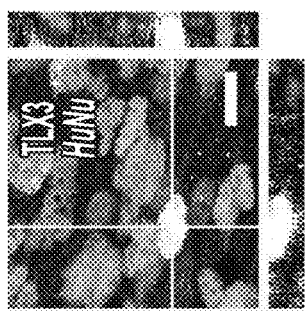
Figure 13C:
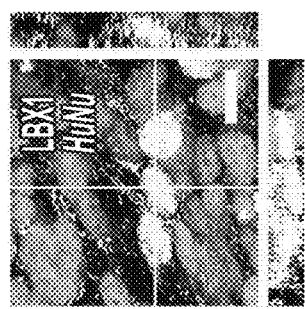
Figure 13G:
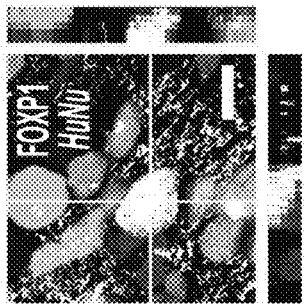
Figure 13J:
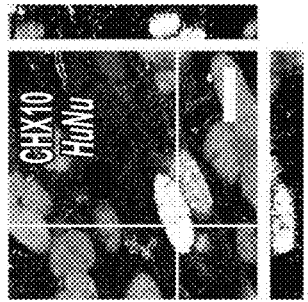
Figure 13B:
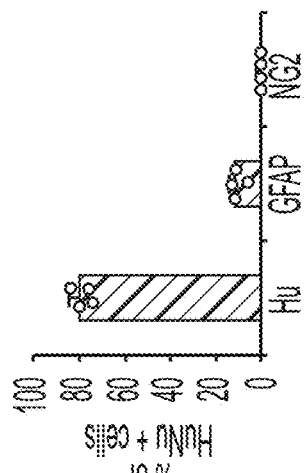
Figure 13F:
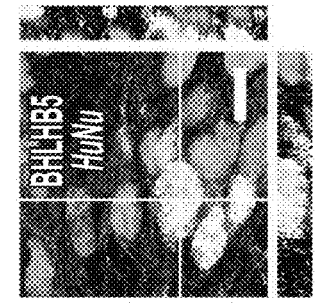
Figure 13I:
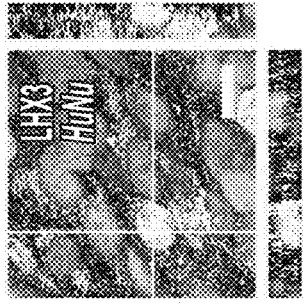
Figure 13A:
Figure 13E:
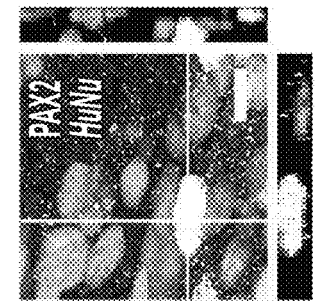
Figure 13H:
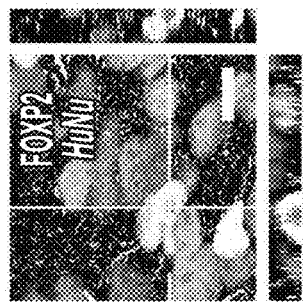
Figure 13K:
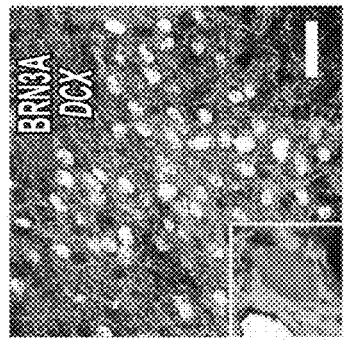
Figure 13L:
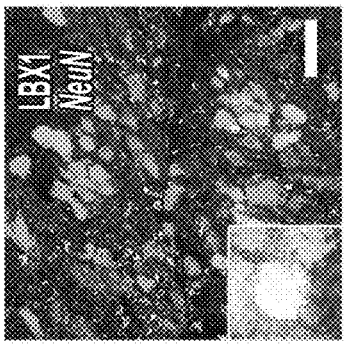
Figure 13M:
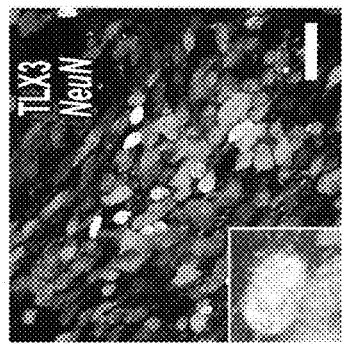
Figure 13N:
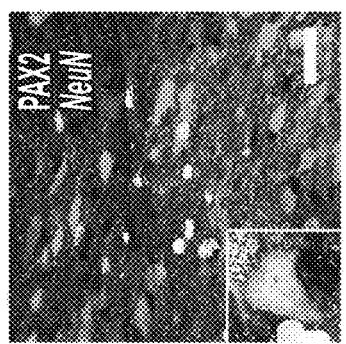
Figure 13O:
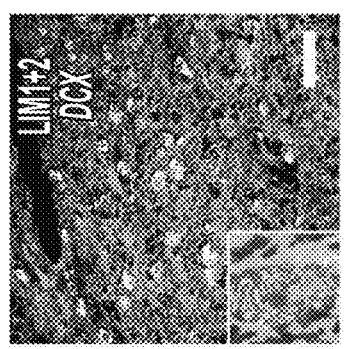
Figure 13P:
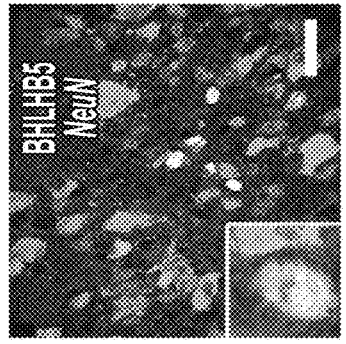
Figure 13Q:
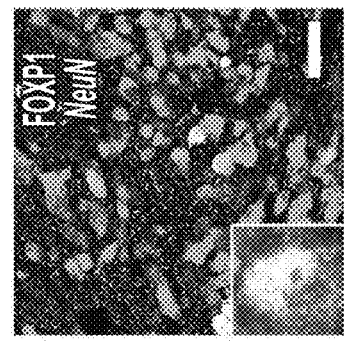
Figure 13R:
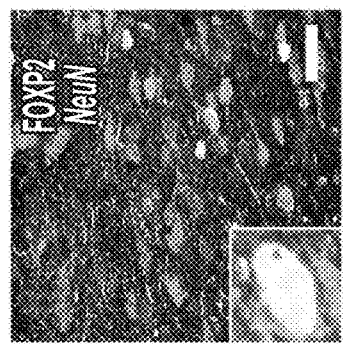
Figure 13S:
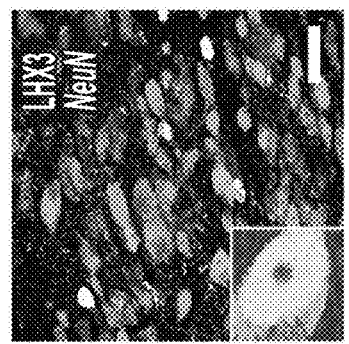
Figure 13T:
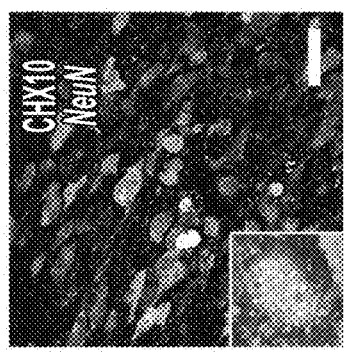

FIGS. 13A-T: Neuronal Subtypes Generated from H9-Derived Spinal Cord NSCs. (FIG. 13A) Confocal images at graft-host border (dashed line: left; graft, right; host), six weeks post-grafting reveals that grafted cells express the neuronal markers DCX and NeuN. Scale bar=200 μm. (FIG. 13B) Neuronal and glial phenotype quantification. 81% of grafted cells express the neuronal marker Hu when assessed three months post-grafting, whereas 11% of grafted cells express the mature astrocyte marker, GFAP, and 1% of cells express the oligodendrocyte precursor cell marker, NG2 (n=4). (FIGS. 13C-J) Confocal images of co-localization of the human-specific nuclear marker, HuNu with spinal cord neuronal subtype-specific transcription factors: sensory interneurons (LBX1 (FIG. 13C) and TLX3 (FIG. 13D)), inhibitory neurons (PAX2 (FIG. 13E), or motor interneurons (BHLHB5 (FIG. 13F), FOXP1 (FIG. 13G, FOXP2 (FIG. 13H), LHX3 (FIG. 13I), and CHX10 (FIG. 13J)). Scale bars=10 μm. (FIGS. 13K-T) Confocal images from center of graft reveal co-localization of the neuronal markers DCX or NeuN with neuronal subtype-specific transcription factors of dorsal neurons (BRN3A (FIG. 13K), LBX1 (FIG. 13L), and TLX3 (FIG. 13M)), inhibitory neurons (PAX2 (FIG. 13N)), or intermediate-ventral neurons (LIM 1+2 (FIG. 13O), BHLHB5 (FIG. 13P), FOXP1 (FIG. 13Q), FOXP2 (FIG. 13R), LHX3 (FIG. 13S), and CHX10 (FIG. 13T), three months post-grafting. Insets show triple labeling of GFP, neuronal markers, and subtype-specific transcription factors. Scale bars=25 μm.

Figure 14A:
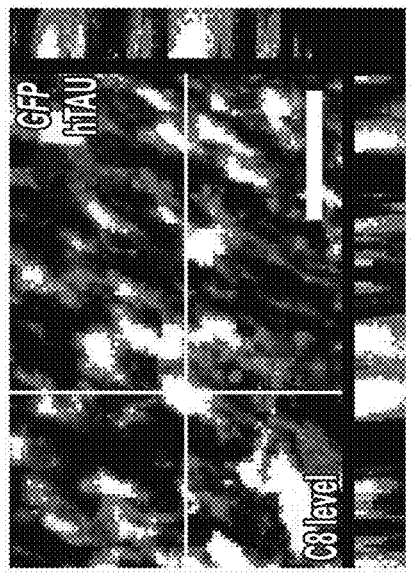
Figure 14B:
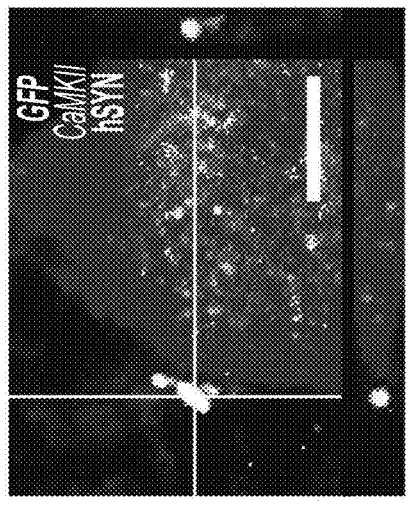
Figure 14C:
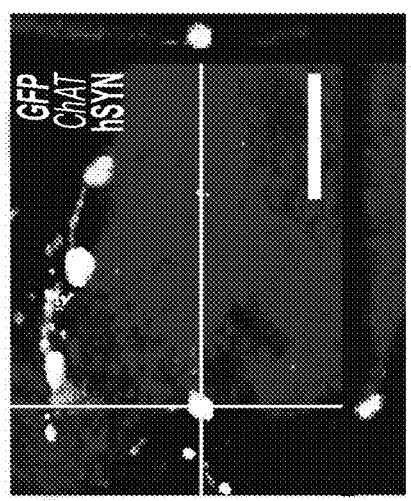
Figure 14D:
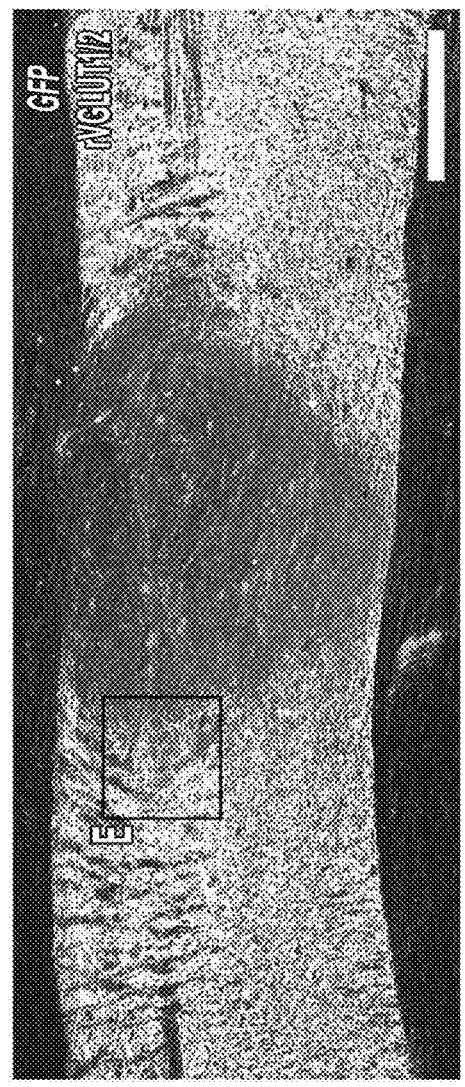
Figure 14E:
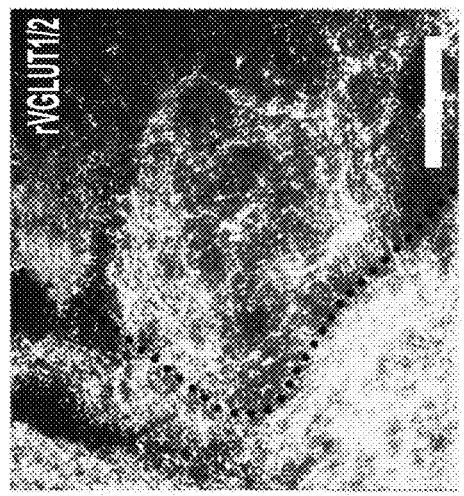
Figure 14G:
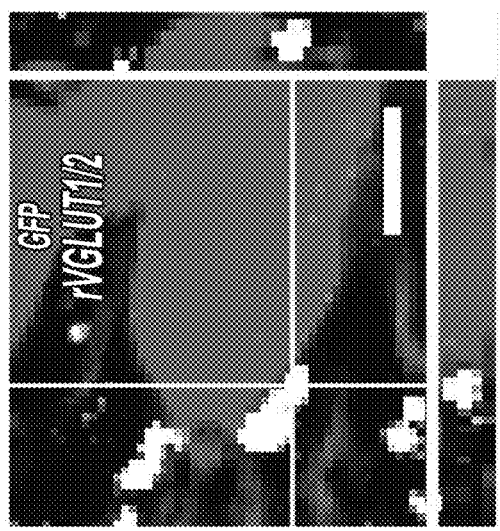
Figure 14F:
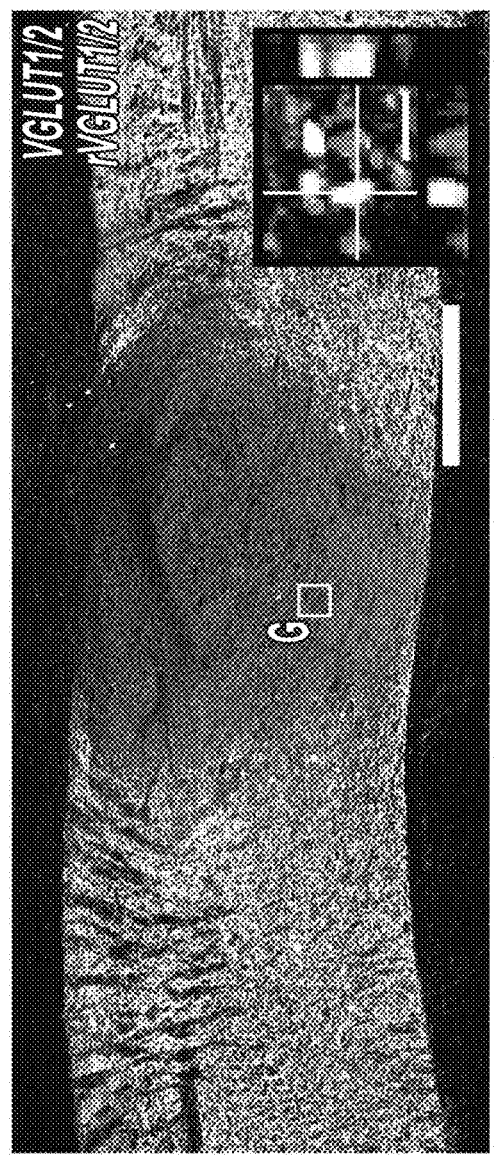

FIGS. 14A-G: Synaptic connectivity of host and H9-Derived Spinal Cord NSCs. (FIG. 14A) Confocal image of co-localization of the graft (GFP) and human-specific axonal TAU (hTAU) at C8 level. Scale bar=20 um. (FIGS. 14B,C) Triple labeling for GFP, human SYN (hSYN), and CaMKII (FIG. 14B) or ChAT (FIG. 14C), indicating co-association of graft-derived human axon terminals with a synaptic marker in direct association with host neurons. Scale bars=5 μm. (FIGS. 14D-F) Sagittal sections triple-labeled for GFP, rat VGLUT1/2 (rVGLUT1/2), and VGLUT1/2, three months post-grafting. Scale bars=500 μm (FIGS. 14D,F) and 100 um (FIG. 14E). High-magnification views of boxed area in FIG. 14D is shown in FIG. 14E. Inset shows higher magnification in boxed area in FIG. 14F. Scale bar=5 μm. Rat VGLUT1/2 (rVGLUT1/2)-expressing rat excitatory presynaptic elements were present at host-graft border (FIGS. 14D,E) (dashed line: left; host, right; graft) and inside the graft (FIG. 14F). VGLUT1/2 is immunoreactive for both human and rat antigens; rVGLUT1/2 labels only rat antigen. (FIG. 14G) Close apposition of rat VGLUT1/2 (rVGLUT1/2) axons terminals in graft onto GFP-expressing cell bodies or dendrites, suggesting host-graft excitatory connection. Scale bar=5 μm. Immunohistochemistry was independently repeated at least twice with similar results.

Figure 15C:
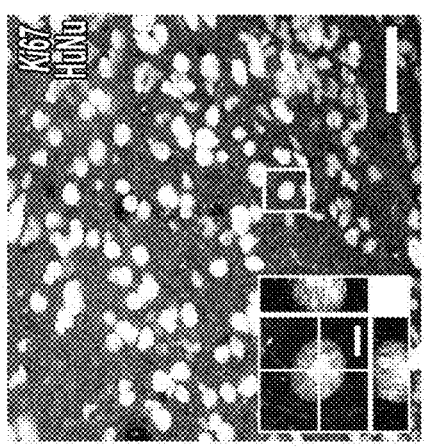
Figure 15B:
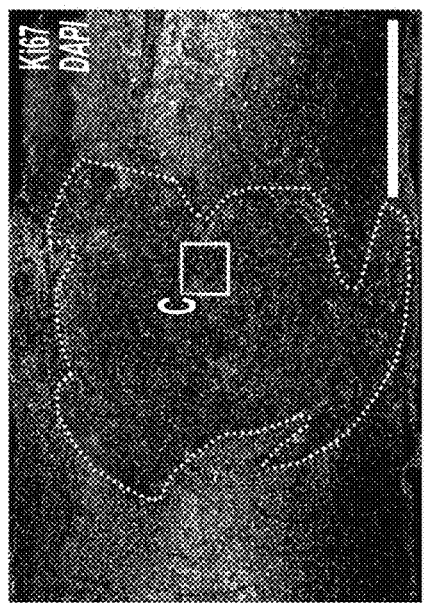
Figure 15A:
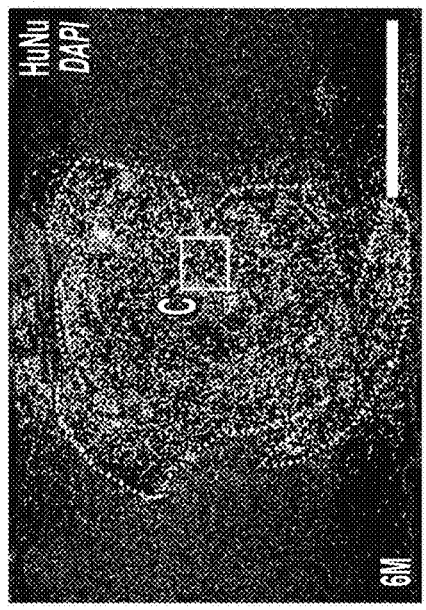
Figure 15D:
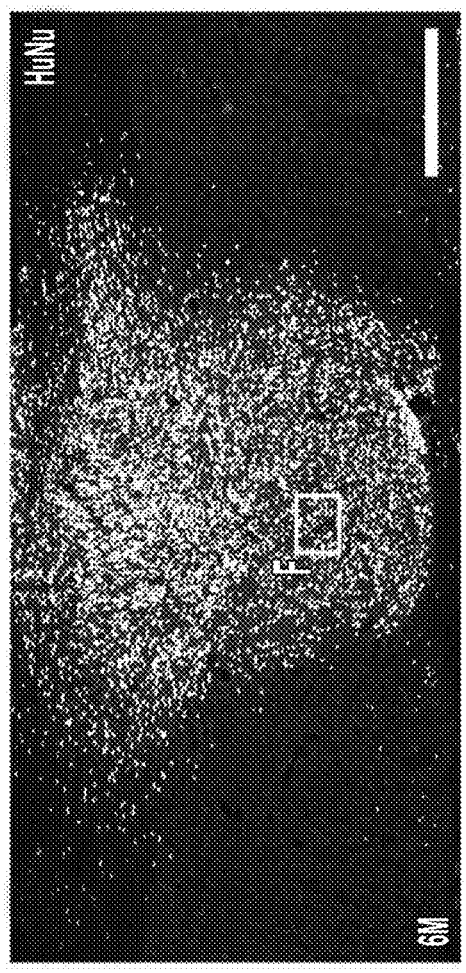
Figure 15E:
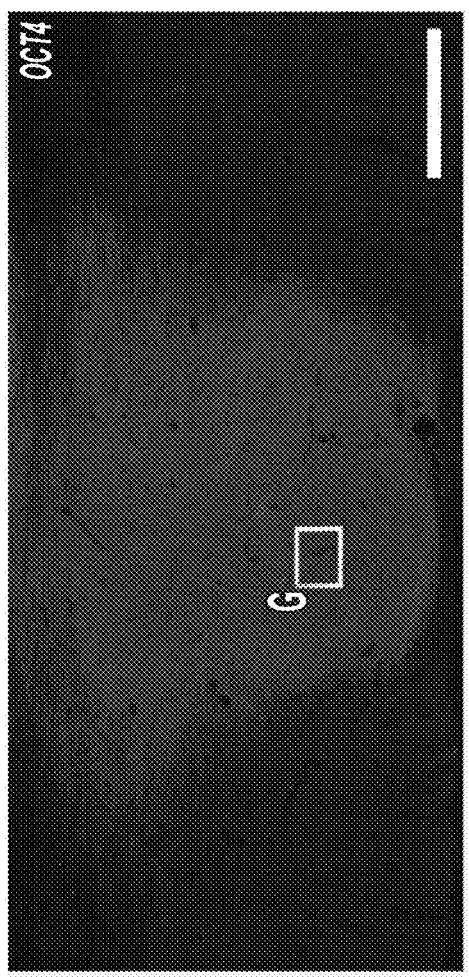
Figure 15H:
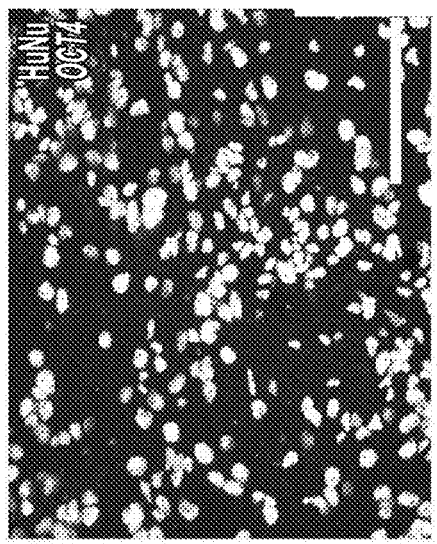
Figure 15G:
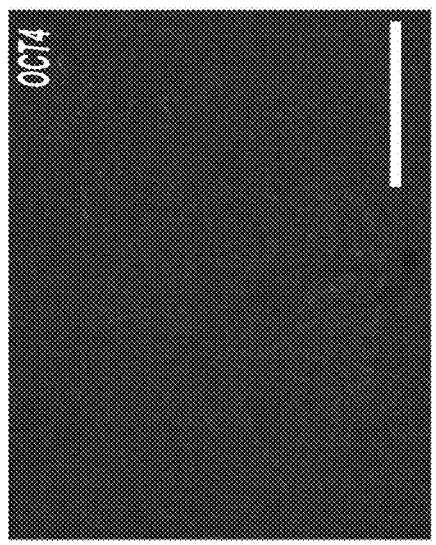
Figure 15F:
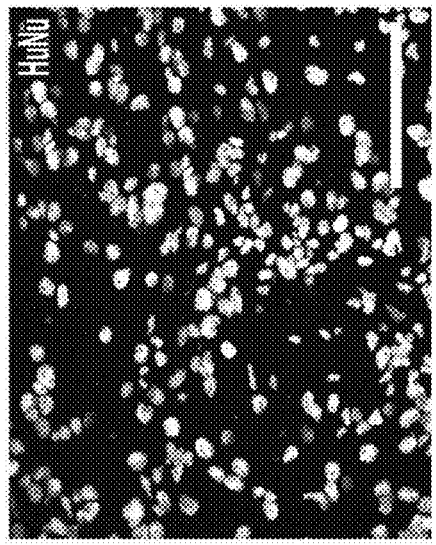

FIGS. 15A-H: Growth of H9-Derived Spinal Cord NSC Grafts. (FIG. 15A-C) Immunolabeling for the human nuclear marker HuNu, proliferation marker Ki67, and DAPI, six-months after grafting. Dashed line indicates the graft-host border. Scale bars=1 mm (FIGS. 15A,B) and 50 um (FIG. 15C). Inset shows higher magnification of boxed area in c. Scale bar=5 um. The graft occupies the lesion cavity without extending beyond it. Only 0.61±0.29% of HuNu-expressing human cells expressed Ki67 (n=3 grafts sampled). (FIGS. 15D-H) Immunolabeling for HuNu and the pluripotent marker OCT4 six-months after grafting. OCT4-expressing cells were not detected. FIG. 15F-H show higher magnification of boxed areas in FIG. 15D and FIG. 15E. Scale bars=500 um (FIGS. 15D,E) and 100 um (FIGS. 15F-H). Data are presented as mean±SEM. Immunohistochemistry was independently repeated twice with similar results.

Figure 16A:
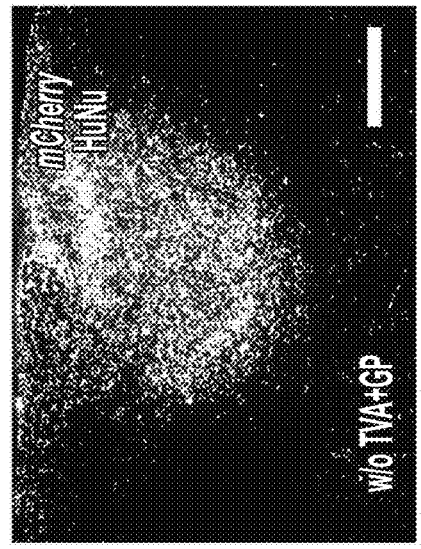
Figure 16B:
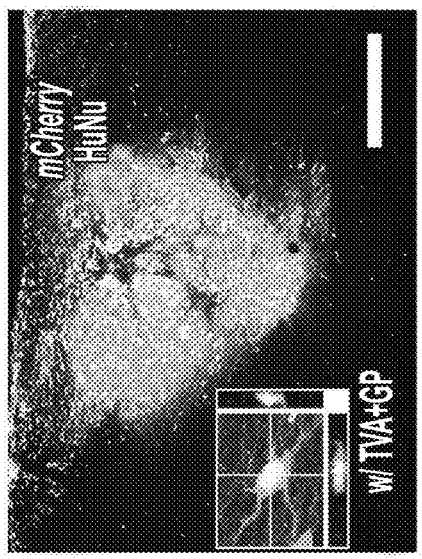
Figure 16C:
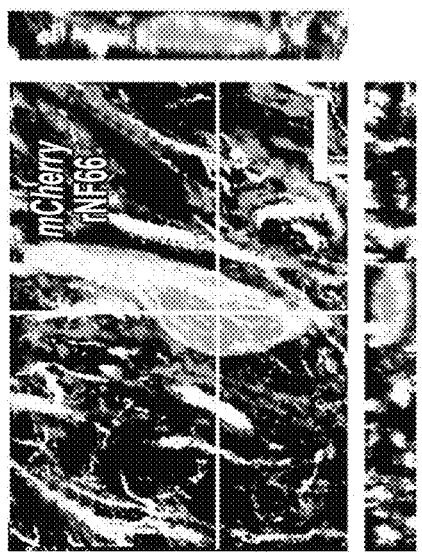
Figure 16D:
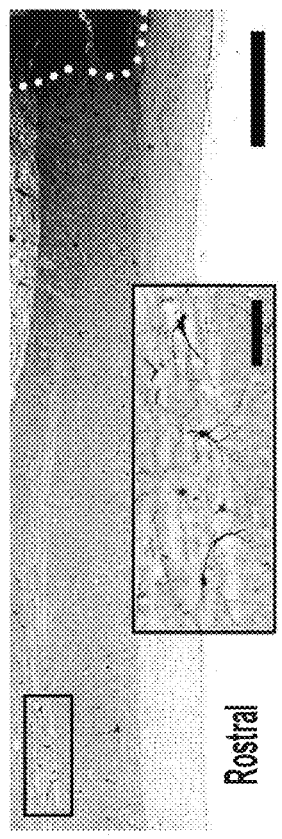
Figure 16E:
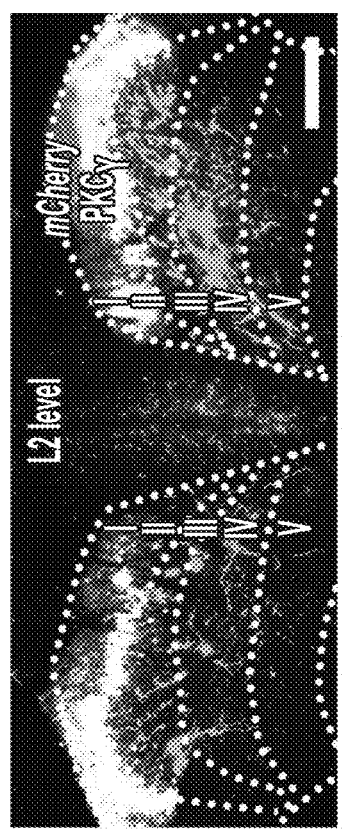
Figure 16F:
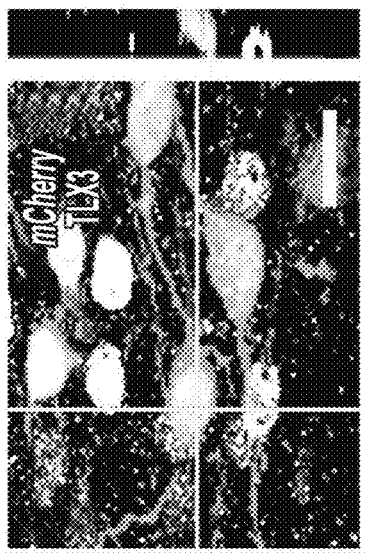
Figure 16G:
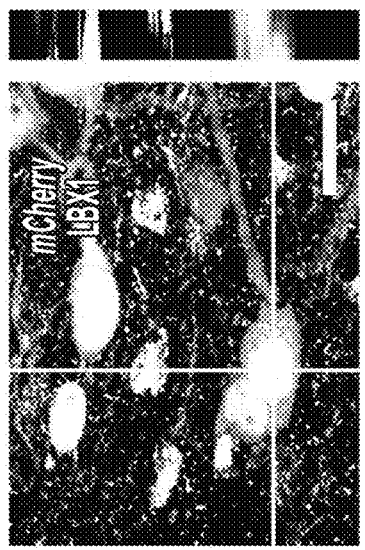
Figure 16H:
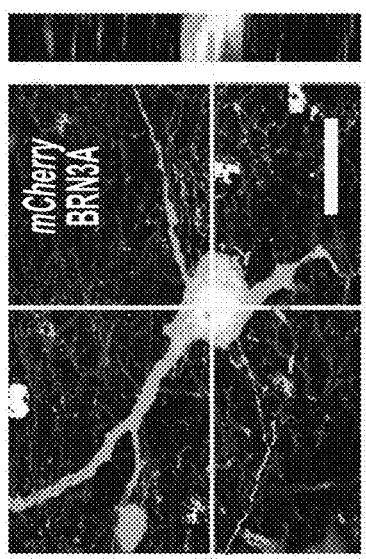
Figure 16J:
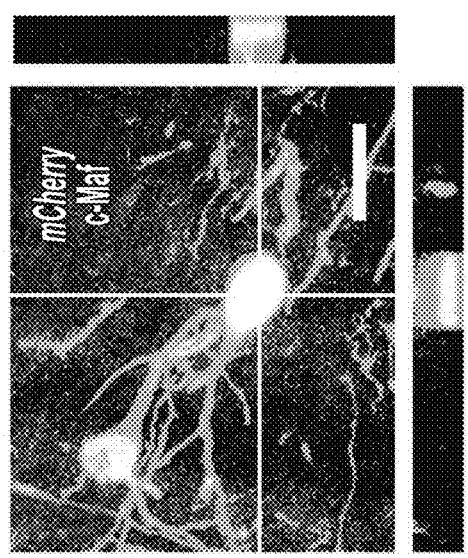
Figure 16I:
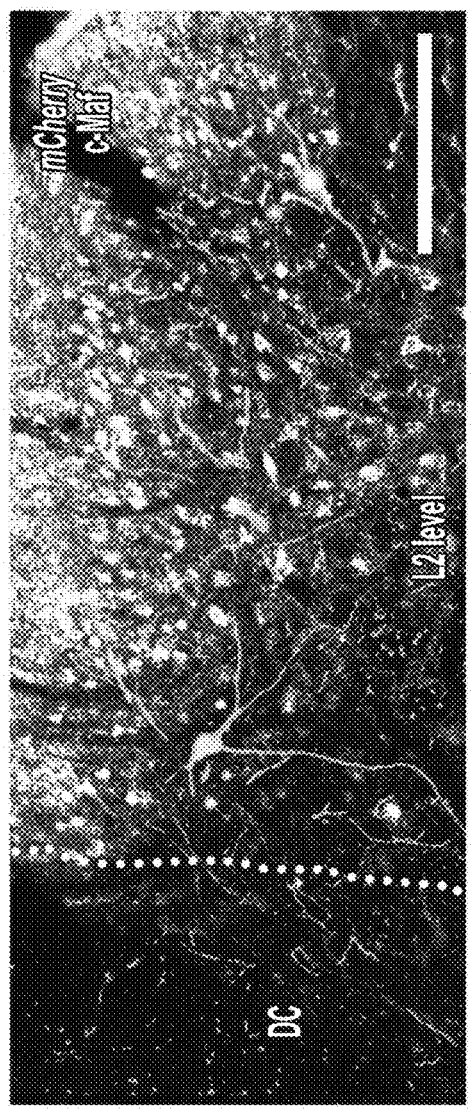

FIGS. 16A-J: Connectivity of Host Intraspinal Neurons with H9-Derived Spinal Cord NSC Grafts. (FIGS. 16A,B) Double immunostaining of mCherry and HuNu for control (w/o TVA+G-protein (GP)) and experimental (w/TVA+GP) rats. No mCherry-expressing cells were founded in control animals. Scale bars=500 μm. (FIG. 16C) Confocal image shows co-localization of rodent-specific alpha-internexin (rNF66) and mCherry. GFP staining is not included to simplify interpretation of the greyscale image Scale bar=10 um. (FIG. 16D) Sagittal section showing retrogradely, trans-synaptically traced host mCherry-expressing cells in the cervical spinal cord rostral to the C4 dorsal column SCI site. Connected host neurons are scattered throughout gray matter. Scale bar=1 mm; inset shows the boxed region. Scale bar=200 um. (FIG. 16E Trans-synaptically labeled cells at the L2 level mainly located in lamina Inner lamina II is indicated by PKCγ staining. Scale bar=250 μm. (FIGS. 16F-H) Characterization of mCherry+ host cells in the cervical spinal cord. Synaptically connected mCherry+ host neurons include somatosensory interneurons labeled for TLX3 (FIG. 16F), LBX1 (FIG. 16G, and BRN3A (FIG. 16H). Scale bars=20 μm. (FIGS. 16I,J Sensory interneurons at the L2 host spinal cord level are synaptically connected with the spinal cord NSC graft, indicated by double labeling for mCherry and sensory interneuronal marker c-Maf. DC; dorsal column. Scale bar=100 μm (FIG. 16I) and 20 μm (FIG. 16J).

Figure 17B:
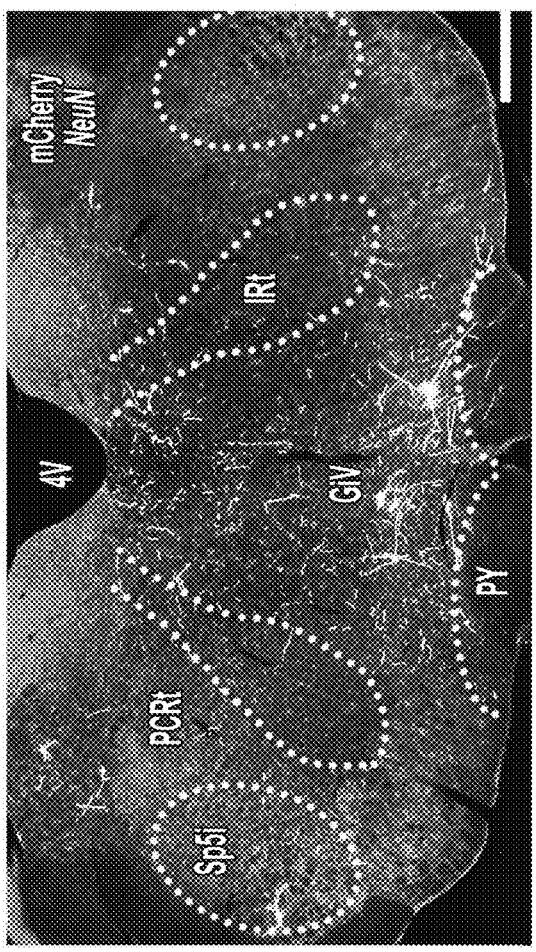
Figure 17A:
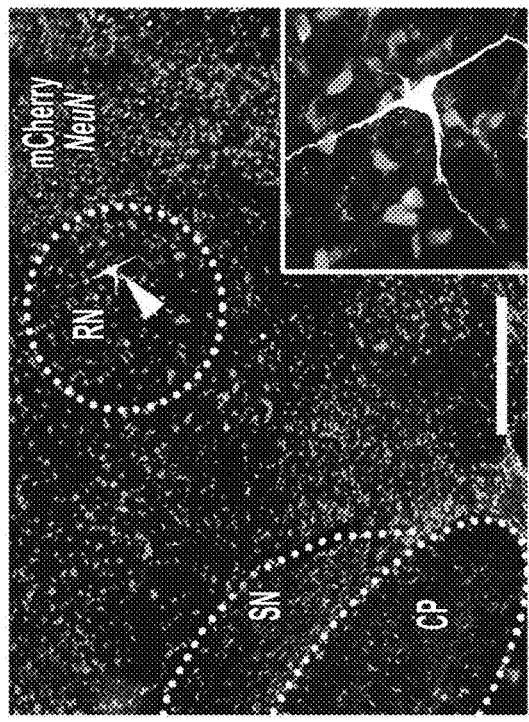
Figure 17E:
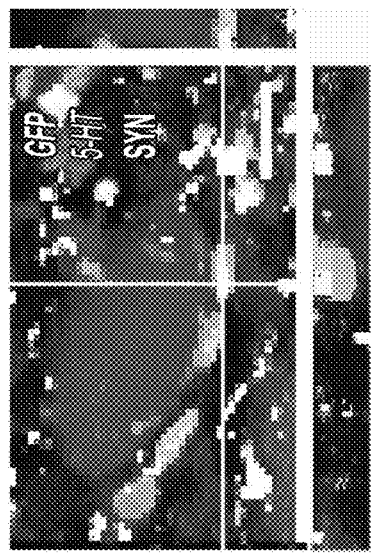
Figure 17D:
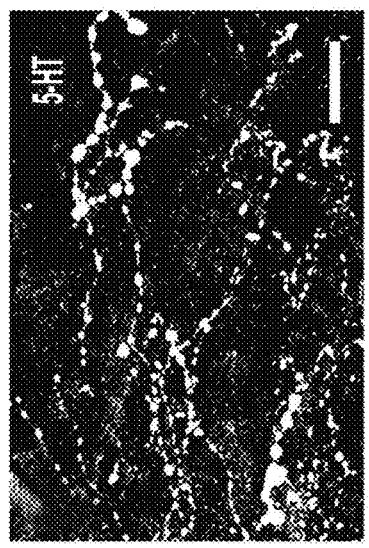

FIGS. 17A-E: Connectivity of Host Supraspinal Neurons with H9-Derived Spinal Cord NSC Grafts. (FIG. 17A Neurons of the red nucleus (RN) in the pons were connected to the graft, indicated by mCherry labeling. Scale bar=500 μm. Inset is high magnification of arrow head. CP; cerebral peduncle. SN; substantia nigra. (FIG. 17B) In the reticular formation, host neurons in the gigantocellular reticular nucleus ventral part (GiV) are synaptically connected to the human graft. Scale bar=500 μm. IRt; intermediate reticular nucleus, PCRt; parvocellular reticular nucleus, PY; pyramidal tract, Sp5i; spinal trigeminal nucleus, interpolar part, 4V; fourth ventricle. (FIGS. 17C-E) Host raphespinal axons (labeled for 5-HT) regenerate into GFP+ H9-derived spinal cord NSC grafts in the lesion site (FIG. 17C); the boxed region is shown in (FIG. 17D). These regenerating axons express the presynaptic marker synaptophysin (SYN) in close association with graft cell somata (FIG. 17E). Scale bars=50 μm (FIG. 17C), 10 μm (FIG. 17D), and 5 um (FIG.

17E). Immunohistochemistry was independently repeated at least twice with similar results.

FIGS. 18A-F: Connectivity of Host DRG Neurons with H9-Derived Spinal Cord NSC Grafts. (FIGS. 18A-C) Neurons in multiple dorsal root ganglia (DRG) in proximity to the graft at C4 are labeled for mCherry, indicating connectivity with the human NSC graft. (FIG. 18A Cervical, (FIG. 18B) thoracic, and (FIG. 18C) lumbar DRGs. Scale bars=1 mm. (FIGS. 18D,E) High magnification images of mCherry-expressing cells in C7 (FIG. 18D) and L3 (FIG. 18E) DRGs. Scale bars=500 urn. (FIG. 18F) Double immunolabeling for mCherry and NF200 in C5 DRGs showing co-localization of large diameter DRG neurons with mCherry. Scale bar=100 µm. Similar pattern was observed in all experimental animals (n=4).

Figure 19G:
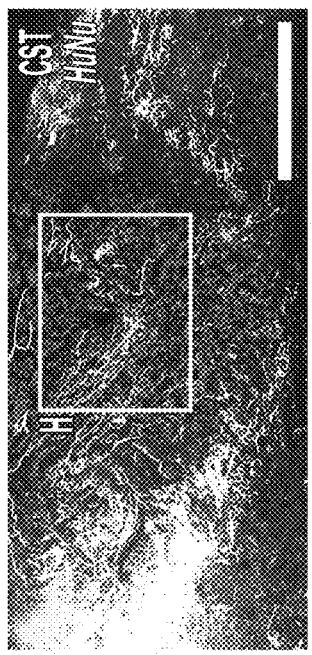
Figure 19F:
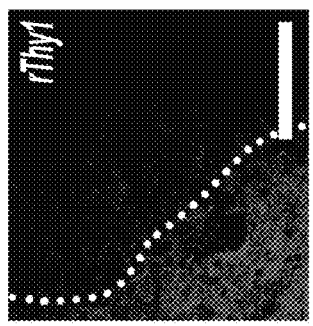
Figure 19E:
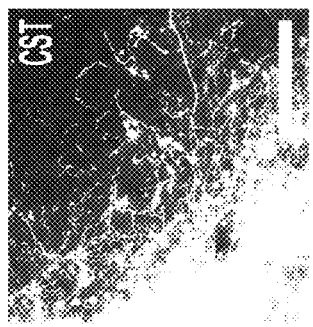
Figure 19H:
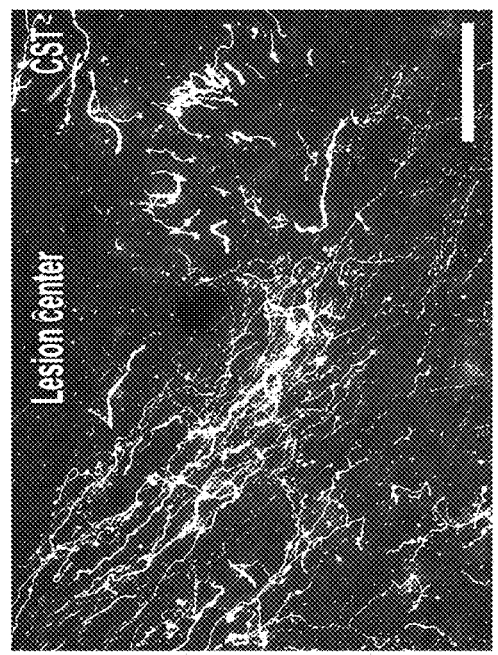

FIGS. 19A-H: Corticospinal Regeneration into H9-Derived Spinal Cord NSC Grafts. To demonstrate that rat corticospinal axons clearly regenerate into the human neural stem cell graft within the lesion site, double labeling for rat Thy1 (rThy1) and host corticospinal axons was performed. (FIG. 19A) Rat Thy1 is expressed in host gray matter and is absent from the lesion site containing the human neural stem cell graft. (FIG. 19B) In the same section, corticospinal axons regenerate into the lesion site containing the human neural stem cell graft, which lacks Thy1 labeling. (FIG. 19C) Dual color composite of 19A and 19B. Boxed area in 19C is enlarged as FIG. 5J. Scale bars=500 um (FIGS. 19A-C). (FIGS. 19D-F) Host corticospinal axons regenerating in a human neural stem cell graft occupying the lesion site; the graft does not label for rThy1. Boxed area in FIG. 19D is enlarged as FIG. 19E and FIG. 19F. Scale bars=250 um (FIG. 19D) and 100 um (FIGS. 19E,F). (FIGS. 19G,H) The graft in the lesion site is labeled for the human-specific nuclei marker HuNu. Host corticospinal axons (CST) regenerate into the graft. Boxed area (the lesion center) is shown in FIG. 19H. Scale bars=500 um (FIG. 19G) and 100 um (FIG. 19H). Corticospinal tracing experiments were independently repeated twice with similar results.

Figure 20B:
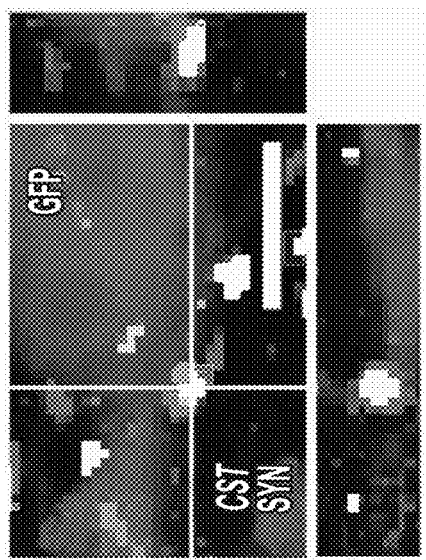
Figure 20F:
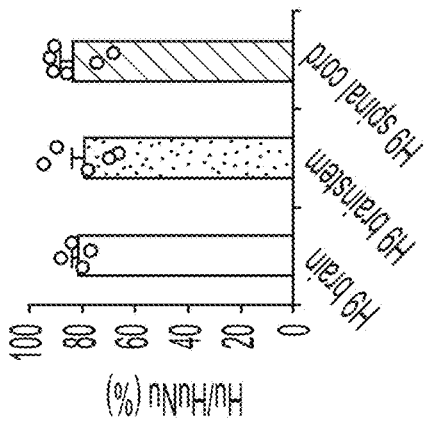
Figure 20A:
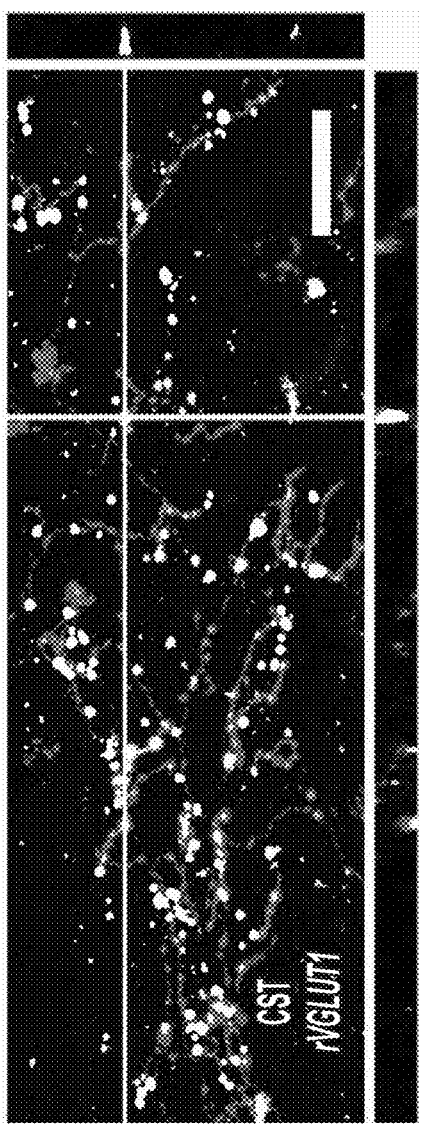
Figure 20E:
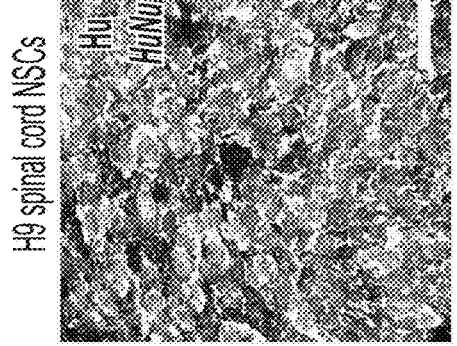
Figure 20D:
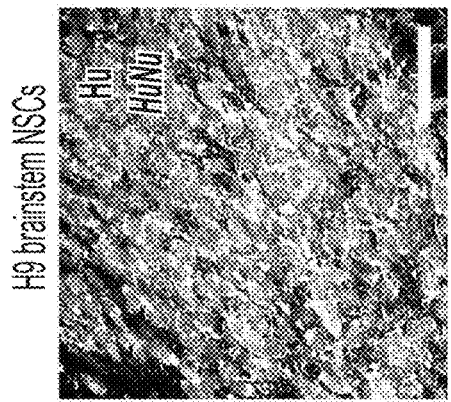
Figure 20C:
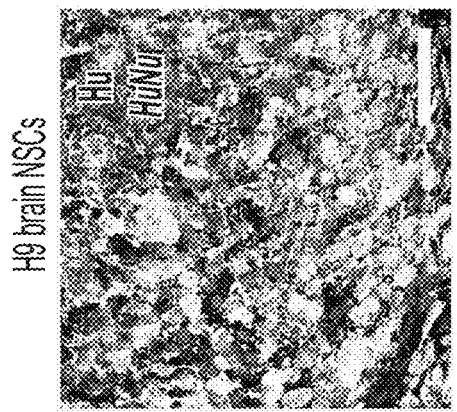

FIGS. 20A-F: Corticospinal Regeneration into H9-Derived Spinal Cord NSCs. (FIG. 20A) Double labeling for corticospinal axons and rat-specific VGLUT1 (rVGLUT1) within spinal cord NSCs. Scale bar=20 µm. (FIG. 20B) Immunolabeling for GFP, corticospinal axons, and SYN reveals co-localization of regenerating corticospinal axon terminals with rat SYN, suggesting synaptic connectivity. Scale bars=5 µm. (FIGS. 20C-F) Quantification of graft-derived neurons (Hu$^+$/HuNu$^+$ cells) (FIG. 20F) among H9-brain (FIG. 20C, n=4), brainstem (FIG. 20D, n=5), and spinal cord NSCs (FIG. 20E, n=6). Hu labels all neurons (human or rodent; images are from within graft which contains only human neurons), whereas HuNu exclusively labels the nuclei of human cells. There were no statistical differences among groups (One-way ANOVA, $F_{(2, 12)}$=0.28, P=0.78), indicating that differences in the proportion of neurons among graft types did not account for the support of corticospinal regeneration. Scale bars=50 µm. Data are presented as mean±SEM. Data was obtained from independent two experiments with similar results.

Figure 21G:
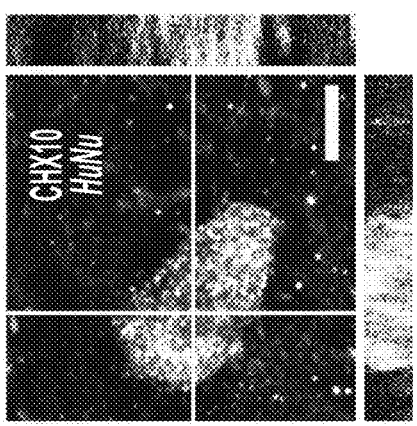
Figure 21H:
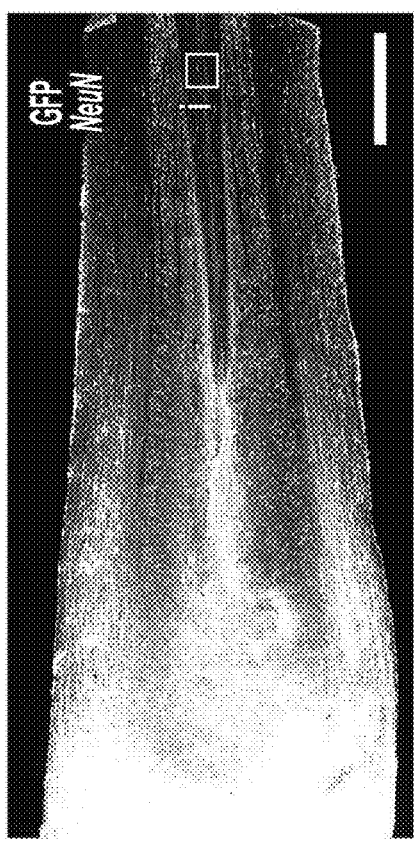
Figure 21I:
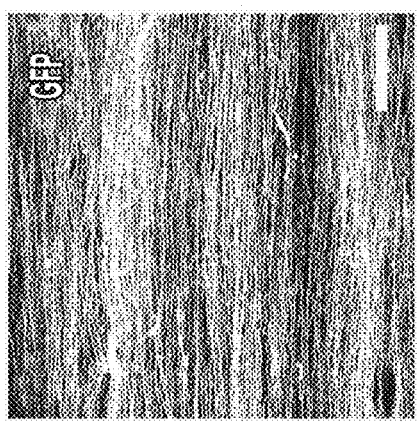
Figure 21J:
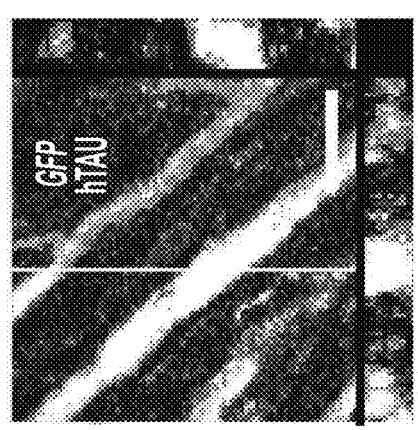
Figure 21K:
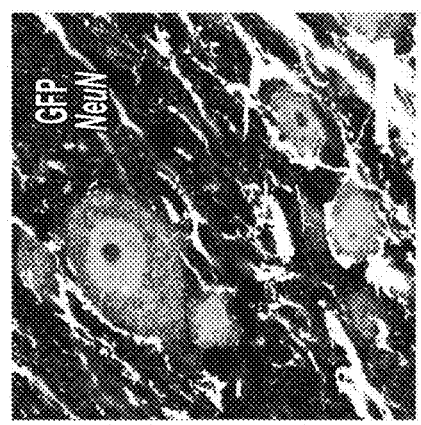
Figure 21L:
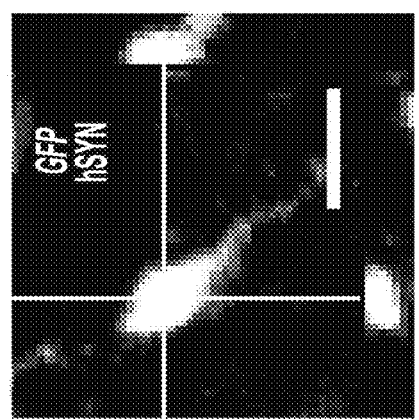
Figure 21M:
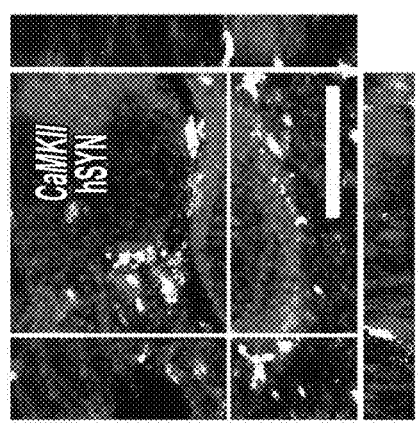

FIGS. 21A-M: Survival, Differentiation, and Axonal Extension of H9-Derived Spinal Cord NSCs Grafted to Thoracic Contusions. (FIG. 21A) GFP-labeled H9-spinal cord NSCs were grafted into sites of T10 spinal cord contusion. Horizontal section labeled for GFP and NeuN, showing graft fill of the lesion cavity assessed five months after grafting. Scale bar=1 mm. Rostral is to left, and caudal is to right. (FIG. 21B) Ungrafted T10 contusion cavity. Scale bar=1 mm. (FIGS. 21C,D) Immunolabeling for doublecortin (DCX) and human nuclei (HuNu) around the center of grafts, indicating neuronal differentiation of grafted cells. Scale bars=50 um (FIG. 21C) and 5 um (FIG. 21D). (FIG. 21E) Immunolabeling for the neuronal marker NeuN and GFP. GFP-expressing grafts differentiate into neurons expressing a mature neuronal marker. Scale bar=50 um. Separate images of boxed area are shown in right panels. Scale bars=10 um. (FIGS. 21F,G Confocal images show the human-specific nuclear marker HuNu co-localizing with the neuronal marker NeuN (FIG. 21F) and the V2a interneuronal marker CHX10 (FIG. 21G). Scale bars=5 um. (FIGS. 21H,I) Horizontal section labeled for GFP and NeuN showing very large numbers of GFP-labeled axons that extend caudally into the host. Scale bar=1 mm. Dashed line indicates caudal graft-host border. Boxed region is shown in FIG. 21I. Scale bar=100 urn. (FIG. 21J) Confocal image shows co-localization of GFP and human specific axonal marker TAU (hTAU). Scale bar=5 um. (FIG. 21K) High magnification image of GFP-expressing axons in the host gray matter caudal to the lesion. Scale bar=20 um. (FIG. 21L) Confocal image shows GFP-labeled human axon terminal expresses human specific pre-synaptic marker synaptophysin (hSYN). Scale bar=2 um. (FIG. 21M Confocal image shows human synaptophysin (SYN)-expressing human synaptic terminals in close apposition with the host CaMKII-expressing neurons caudal to the lesion, indicating graft-host connectivity. Scale bar=10 um. Immunohistochemistry was independently repeated twice with similar results.

FIGS. 22A-B. Presents a table (in two parts, 22A and 22B) of antibodies used in the experiments.

FIG. 23. Presents a table of primers used in the experiments.

DETAILED DESCRIPTION

Recent findings reveal that appropriately patterned neural stem cells (NSCs), which can provide tissue-specific developing microenvironments, have superior potential to reconstitute damaged neural circuitry and enable axonal regeneration. For treating disorders of the spinal cord, including spinal cord injury (SCI), amyotrophic lateral sclerosis (ALS), spinal muscular atrophy (SMA), and other spinal cord-specific disorders, a source of cells of regional spinal cord identity that is capable of generating multiple neuronal and glial derivatives is needed. However, protocols to derive and maintain regionalized spinal cord NSCs from human pluripotent stem cells (hPSCs) have not existed.

The importance of generating NSCs of regional spinal cord identity is illustrated by the fact that corticospinal axons, the most important system for human voluntary motor function, only regenerate into neural grafts of spinal cord identity. This homologous reconstitution of the lesioned adult spinal cord with spinal cord multipotent neural progenitor cells (NPCs) was achieved using developmental primary spinal cord tissue, and these grafted cells formed synaptic relays across lesion sites to significantly improve functional outcomes. In contrast, corticospinal axons did not regenerate into rostrally-fated (brain) neural progenitors. Human embryonic stem cell (hESC) lines are readily available as a source for human clinical trials and are more broadly accepted ethically than primary human neural tissue, highlighting the importance of generating spinal cord NSCs from such cell lines.

Recent progress in spinal cord developmental research has revealed that SOX2$^+$/Brachyury(T)$^+$ neuromesodermal progenitors (NMPs) reside in a caudal stem zone and are the endogenous cellular source of the spinal cord. Early epiblasts acquire neural fates either in the anterior neural plate, which contributes brain progenitors, or via the induction of primitive streak-associated neuromesodermal progenitors, which contribute spinal cord progenitors. The brain and spinal cord therefore have independent origins early in development. Although retinoic acid has been used to generate caudalized cells, retinoic acid activates only rostral homeobox (HOX) genes (HOX1-5 paralog), which pattern brain neuroepithelial cells (NEPs) with a broad brainstem-to-rostral cervical spinal cord identity. In contrast, synergistic wingless-type MMTV integration site protein family (WNT) and fibroblast growth factor (FGF) signals are necessary and sufficient to induce more caudal neuraxis spinal HOX gene expression (HOX6-9 paralog) and specify cervical and thoracic spinal cord identity.

The herein disclosed methods induce and maintain functional human spinal cord NSCs. Importantly, these NSCs include all six dorsal spinal cord neuronal progenitor cell types (pd1-6), and all of the ventral spinal cord neuronal progenitor cell types (pV0-3 and pMN) and can yield a broad range of identified spinal cord neuronal phenotypes (DI1-6, V0-3, and Motor neurons), but not rostral identity cells. The ability to create spinal cord motor neurons and interneurons can facilitate disease modeling and drug screening for several disorders with extensive spinal cord pathology, including ALS, SMA, progressive muscular atrophy, hereditary spastic paraplegia, Friedreich's ataxia, tabes *dorsalis*, and others.

Stem cells are cells that can differentiate into other cell types, but that can also self-renew indefinitely, to replace themselves. Totipotent and pluripotent stem cells can differentiate into all, or a wide array, of cell types influenced by signals present in the environment. In an early stage in differentiation, stem cells retain their "sternness", but become restricted to giving rise to a particular lineage of cell types, for example, hematopoietic stem cells and NSC. However, these cells still give rise to many cell types and are termed multipotent. Stem cells can also acquire patterning, giving the a positional identity within the body of an organism, such as spinal cord NSC, as distinct from other types of NSC that, for example give rise to neuronal cells in various regions of the brain. In a further stage of differentiation, the ability to self-renew becomes finite and the cells give rise to only one or a few cell types. These are unipotent and oligopotent progenitor cells.

Of further importance, human embryonic stem cell-derived NSCs are an appropriate cell type for clinical translation for spinal cord "replacement" strategies in spinal cord injury and other disorders. Only spinal cord-fated cells enable regeneration of corticospinal axons, but an hPSC-derived spinal cord NSC cell line has not been previously derived. It is demonstrated herein that spinal cord NSCs enable host corticospinal regeneration and synapse formation in the injury site, and in turn, grafted human NSCs extended very large numbers of axons into the host spinal cord over long distances. These extending human axons form synapses with the host spinal cord below the lesion, establishing a potential neural relay across the lesion site. By using a retrograde monosynaptic rabies tracing system, it is shown that human spinal cord NSC grafts establish connectivity with all of the classic brainstem and cortical host neurons that influence motor function, together with a diverse population of intrinsic spinal cord neuronal populations as well as primary sensory neurons.

Described herein are spinal cord NSCs from hESCs or other hPSC. In some embodiments, methods are described to determine whether these cells can reconstitute damaged spinal neural circuitry and support corticospinal regeneration. In some embodiments, described is a derivation of spinal cord NSCs from hESCs by activation of WNT and FGF signaling, together with dual inhibition of SMAD signaling, that is, inhibition of both BMP and TGF-β. These human spinal cord NSCs generated motor neurons and a diversity of spinal interneurons comprising multiple positions in the spinal cord dorso-ventral axis, which could be maintained in vitro for prolonged time periods, and survived in lesioned rat spinal cords where they enabled robust corticospinal regeneration. Furthermore, grafts interconnected with multiple intraspinal and supraspinal systems, as assessed by glycoprotein-deleted rabies trans-synaptic virus tracing. Together, hPSC-derived spinal NSCs could represent an optimal cell type for spinal cord study and therapeutic transplantation for several spinal cord disorders.

Access to cells providing "spinal cord neurons" enable a broad range of biomedical applications in vitro and these newly generated hPSC-derived spinal cord NSCs thus constitute the optimal cell type for clinical translation for spinal cord "replacement" strategies in several spinal cord disorders.

Induction of Spinal Cord Neural Stem Cells

Pluripotent stem cells (for example, hESC or induced pluripotent stem cells (iPSC)) are grown to about 70% confluence in an appropriate medium (such as an hESC growth medium, for example, mTeSR medium, but any complete media for human ESC or iPSC could be used). In some embodiments the culture plates are coated with MATRIGEL® or vitronectin. No feeder cells are required and in some embodiments none are used. The culture medium is then switched to an induction medium containing inhibitors of bone morphogenetic protein (BMP), activin, and transforming growth factor β (TGF-β), as well as one or more caudalizing morphogens. Some embodiments further include an inhibitor of Notch signaling. In some embodiments the base medium for the induction medium is N2B27 medium. (N2B27 medium is knockout Dulbecco's Modified Eagle's Medium (DMEM)/F12: Neurobasal (1:1), 1×N2, 1×B27, 1x penicillin/streptomycin, 1x Glutamax). In some embodiments, the BMP signaling inhibitor is LDN-19318. In some embodiments, the activin and TGF-β signaling inhibitor is SB-431542. In some embodiments, the one or more caudalizing morphogens are fibroblast growth factor 2 and fibroblast growth factor 8 (FGF2/8), and an activator of WNT signaling. In some embodiments, the activator of WNT signaling is a GSK3β inhibitor, for example, CHIR99021. In some embodiments, the inhibitor of Notch signaling is a γ-secretase inhibitor, for example, DAPT. In some embodiments, the cells are cultured in induction medium for 10 days, the cells are split and fresh medium is added at regular intervals, for example daily. This culture protocol induces the hPSC to develop into neural stem cells and, ultimately, into spinal cord neural stem cells.

In some embodiments, SB-431542 is used at a concentration of 5-10 μM, or any integral value therein. In some embodiments, CHIR99021 is used at a concentration of 3-4 μM, or any integral value therein. In some embodiments, FGF2 and FGF8 are used at a concentration of 25-100 ng/ml each, or any integral value therein. In some embodiments no inhibitor of Notch signaling, such as DAPT, is used. Other components may be used at the concentrations described in the Examples below. Generally, use of the various components at the lower end of the above concentration ranges leads to greater genetic and phenotypic stability, including stability of the spinal cord NSC phenotype and lower potential for tumorigenicity. This consideration also applies in the maintenance and expansion phase. In some particular embodiments, the concentration of SB-431542 is 5 µM, the concentration of CHIR99021 is 3 µM, the concentrations of FGF2 and FGF8 are 25 ng/ml, and no DAPT is used. In a further aspect of these embodiments, no inhibitor of Notch signaling is used. In some embodiments the plate coating is changed to CELLSTART® (ThermoFisher Scientific) at passage 4 and to poly-L-ornithine at passage 6.

Maintenance and Expansion of Spinal Cord Neural Stem Cells

Once the spinal cord neural stem cell phenotype is obtained, the cells can be further expanded and the phenotype maintained in culture by switching to a neural maintenance medium (a neurobasal medium; that is, a basal medium that meets the cell culture requirements of neuronal cells) containing inhibitors of activin and TGF-β signaling, and activators of WNT and SHH signaling. In some embodiments the base medium of the neural maintenance medium is N2B27 medium. In some embodiments the activin and TGF-β signaling inhibitor is SB-431542. In some embodiments the activator of WNT signaling is a GSK3β inhibitor, for example, CHIR99021. In some embodiments the activator of SHH is Hh-Ag1.5.

In some embodiments, the concentration of SB-431542 is 2 µM. In some embodiments, the concentration of CHIR99021 is reduced to 2 µM from the amount used during induction. In some embodiments the concentration of Hh-Ag1.5 is 100 nM. In some embodiments, components may be used independently at the concentrations described in the Examples below.

One of the major impediments to the development of practical biomedical uses of neural stem cells for humans has been the rapidity with which they undergo terminal differentiation in culture. This has made it impractical to generate the number of cells needed, and have them available, for transplant. While neural stem cells and neural progenitor cells can survive implantation and engraftment, cells that have already differentiated past the progenitor cell stage do not survive. Although spinal cord NSC cultured and expanded in the disclosed maintenance medium do not retain a stem cell phenotype indefinitely, eventually differentiating into neural, astrocyte, and oligodendrocyte progenitor cells, they do not differentiate past the progenitor cell stage. Additionally they retain their spinal cord positional identity. Thus it becomes possible to generate substantial numbers of cells, sufficient for implantation and capable of survival and engraftment.

It is important that the differentiation into progenitor cells produces progenitors for all three types of neuronal cell types: neurons, astrocytes, and oligodendrocytes. In repairing neuronal lesions, whether due to injury, disease or disorder all three cell types play a role. Neurons replace neurons that have been destroyed or damaged beyond repair. Astrocytes support the engraftment and survival of the neurons and can also reconstitute the blood-brain barrier. Oligodendrocytes mediate myelination of the axons of the new neurons and remyelination of damaged neurons.

Source of Human Pluripotent Stem Cells

Generally, any source of hPSC can be used in the induction of spinal cord NSC, but spinal cord NSC (including progenitor cells) generated from different sources offer different advantages. Established hESC lines are well-characterized and readily obtainable. They are suited to a wide variety of laboratory application. However, if used in biomedical applications (that is, for implantation into a patient), they will generally not provide an immunological, major histocompatibility complex (MHC) match (that is, they will be allogenic) to any particular patient, so treatment with allogeneic hESCs will typically need to include immune suppression.

iPSC can also be used and avoid ethical issues related to the acquisition of human embryonic tissue. They are similarly suitable for laboratory applications. In biomedical use, iPSC offer the possibility of autologous sourcing, ensuring an MHC match and thus obviating immune suppression. iPSC can be used for allogeneic donation as well. However, the risk of tumorigenicity is greater than with hESC-derived cells.

Another approach to obtaining MHC-matched hPSC for individual patients is to establish a bank of MHC-typed hPSC lines of diverse types. Both hESC and iPSC, or a mixture thereof, could be used to establish the bank.

Spinal Cord Neural Stem Cell Compositions

The induction culture results in a population of cells with a spinal cord neural stem cell phenotype. This positional identity or patterning sets these cells apart from previously obtained neural stem cell cultures, which all had forebrain or hindbrain positional identities (patterning). Spinal cord neural stem cells exist in nature, but only as integrated into a complete (if possibly still developing) organism. Nor has it been feasible to isolate and culture them. The presently disclosed spinal cord NSC cultures represent more highly-enriched populations of spinal cord NSC than has been previously achieved. In some embodiments the cells are >95% spinal cord NSC. However, any population will typically comprise multiple kinds of NSC, such as, SOX1$^+$/SOX2$^+$ NSCs, SOX1$^-$/SOX2$^+$ NSCs, SOX2$^+$/PAX6$^+$ NSCs, SOX2$^+$/NKX6.1$^+$ NSCs, and SOX2$^+$/OLIG2$^+$ NSCs. Thus, enriched or homogenous populations of spinal cord neural stem cells, and in vitro cultures thereof, constitute embodiments disclosed herein.

Unlike earlier efforts, the present spinal cord neural stem cells can be maintained in a non-terminally differentiated state for an extended period of time of at least several months, and the number of cells can be expanded to enable laboratory and clinical uses. The maintenance of the stem cell aspect of the phenotype is not indefinite, with differentiation into the various neuronal progenitor cell types. However, because all three progenitor types (neuronal, astrocyte, and oligodendrocyte) are produced, this population of cells continue to enable uses including implantation into a patient where the cell engraft, survive, and make functional connections with the endogenous tissue. Importantly, the patterning of spinal cord positional identity is maintained. Thus, some embodiments are ex vivo populations of cells predominantly comprising (or consisting essentially of) neural stem cells and neural progenitor cells with spinal cord positional identity patterning. Other embodiments are ex vivo populations of cells predominantly comprising (or consisting essentially of) neural progenitor cells with spinal cord positional identity patterning. In aspects of these embodiments, the neural progenitor cells are a mixture of neuronal progenitor cells, astrocyte progenitor cells, and oligodendrocyte progenitor cells. In further aspects the neural progenitor cells include motor neuron progenitor cells. In further aspects the neural progenitor cells can comprise dorsal and ventral spinal cord progenitors.

In various embodiments the cell compositions comprise pharmaceutically acceptable diluents, excipients, or carriers. These can include culture media and buffered saline solutions. In still further embodiments the cell compositions comprise a cryopreservative so that they may be stored frozen. In some embodiments the cryopreservative (or cryoprotectant) comprises glycerol or dimethyl sulfoxide.

Terminology such as enriched, near-homogeneous, consisting essentially of, and predominantly comprising, acknowledge that cultures and cell populations may not consist exactly of only the indicated cells types. It is used to indicate that the indicated cell type(s) make up a much larger proportion of the culture or population than would be found in any tissue sample directly obtained from a living organism, or cultured therefrom (or that exists in a living organism), and to indicate that other cell types are present in negligible amounts, whether from contamination or non-synchrony of differentiation. While these terms are used to convey that the overwhelming majority of the cells are spinal cord NSC and/or spinal cord neuronal progenitor cells, it should not be interpreted to indicate that these cells are all of the same kind or subtype that exist within the rubrics of spinal cord NSC and spinal cord neuronal progenitor cells, unless explicitly stated.

These cells, cultured neural stem cells and/or neural progenitor cells, are capable of being used for implantation into a patient for therapeutic effect, as they will survive, engraft, and form functional connections with cells of the recipient. In various embodiments survival and engraftment in a human requires implantation of at least 50 to 200 million cells. In one embodiment survival and engraftment in a human requires implantation of at least 100 million cells. They are also useful in modeling diseases and disorders impacting the spinal cord and in drug screening.

Disease Modeling and Drug Screening

To model diseases and disorders pluripotent stem cells can be obtained from a subject that is genetically determined or predisposed to develop the condition. Induced pluripotent stem cells will typically be the more readily obtained source tissue in this instance. Alternatively, pluripotent stem cells from a healthy donor can be genetically engineered to carry a genetic lesion associated with a disease or disorder, if the genetic basis of the condition is known. In this instance both iPSC and hESC are similarly suitable sources of pluripotent stem cells. In either case, these pluripotent stem cells are then cultured in the neural stem cell induction conditions. As they differentiate, their development can be compared to normal cells to identify markers of the disease process. Chemical and biological agents that might contribute to development of disease can be added to the culture. Chemical and biologic agents (including gene therapeutic agents) can then be tested for their ability to prevent, interrupt or reverse development of the disease, or at least its correlate in tissue culture.

EXAMPLES

Example 1. Human ESCs can be Efficiently Directed to a Spinal Cord Neural Stem Cell Fate Human H9 ESCs cultured under feeder-free conditions were converted into NSCs by switching from hESC growth media to N2B27 media supplemented with LDN-19318 (LDN; a BMP signaling inhibitor), SB-431542 (SB; an activin and TGF-β signaling inhibitor), DAPT (a γ-secretase inhibitor, an inhibitor of Notch signaling), CHIR99021 (CHIR; a GSK3β inhibitor, an activator of WNT signaling), and FGF2+FGF8 (FGF2/8) (FIG. 1A). qPCR analysis revealed a rapid loss of OCT4 and NANOG expression indicating loss of pluripotency, whereas SOX2 expression was persistent, consistent with neural identity (FIG. 1B). Transient up-regulation of the mesodermal marker T was observed three days after neural induction, and gradual up-regulation of neural progenitor marker SOX/occurred from three days after neural induction (FIG. 1B), suggesting that cells acquired neuromesodermal progenitor (NMP) identity. Consistent with these results, CHIR/FGF2/8 treated cells were converted into Bra($T^+$)/SOX2$^+$ multipotent NMPs three days after neural induction (FIG. 1C,D). Neuroectoderm cell fate determinant PAX6 expression and rosette-forming neuroepithelial cells (NEPs) were not observed ten days after neural induction (FIG. 7A,B,E,F), indicating CHIR/FGF2/8 treated cells differentiated into NMPs, but not NEPs. CHIR/FGF2/8 treatment yielded substantially elevated expression of caudal-type homeobox protein 2 (CDX2), a master regulator of caudal HOX genes (FIG. 1E), together with activation of spinal cord-specific caudal HOXC4-10 genes and HOXB6 (FIG. 1E, but there was no activation of rostral patterning genes or floor plate marker genes (FIG. 7C) as demonstrated by the steady or decreased level of expression of FOXG1, OTX2, IRX3, SIX3, KROX20, and MAFB. Up-regulation of mesodermal markers TBX6, FOXC1, and MEOX1, endodermal marker SOX17, and neural crest cell markers FOXD3, SNAI1 (SNAIL), and SOX10, were also not observed (FIG. 7D). In line with the gene expression pattern of caudal patterning genes, 90.1±3.1% of SOX2$^+$ cells expressed CDX2 (n=3, FIG. 1F), and expression of the forebrain marker FOXG1 was no longer detected ten days after neural induction (FIGS. 7E,F). These results demonstrate that hESCs induced with the herein disclosed spinal cord protocol acquired a caudalized, spinal cord positional identity.

Example 2. Long-Term Self-Renewal of Spinal Cord Neural Stem Cells

Figure 9D:
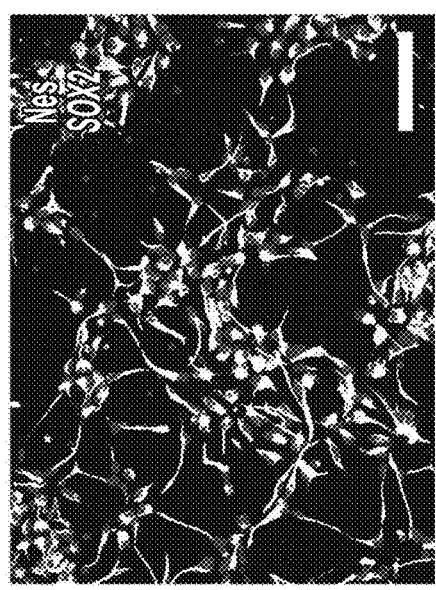

Any differentiation protocol faces the challenge of maintaining cells for extended time periods in vitro, which is important to the generation of sufficient quantities of cells to fill human-sized spinal cord lesion sites. WNT and Sonic hedgehog (SHH) are potent mitogens, whereas bone morphogenetic protein (BMP) directs cells to differentiate into the neural crest lineage in the developing spinal cord. Activation of WNT/SHH and suppression of BMP could specify cells to become spinal cord NSCs and maintain their stemness for prolonged time periods. The neural induction media as described above was changed to N2B27 media supplemented with CHIR, SB, and Hh-Ag1.5 (a potent SHH agonist) ten days after neural induction. In this chemically defined condition, SOX1$^+$/SOX2$^+$/Nestin$^+$ NSCs could be expanded over four months in vitro, through passage 30 (FIG. 1G). Omission of Hh-Ag1.5 or CHIR resulted in a failure to sustain cultures over time due to their differentiation (data not shown). Twenty days after neural induction, cells differentiated into PAX6$^+$/SOX2$^+$ dorsal and NKX6.1$^+$/SOX2$^+$ ventral spinal cord progenitors (FIG. 9D). Induced cells also included OLIG2$^+$/SOX2$^+$ motor neuron progenitors (pMN) and NKX2.2$^+$/SOX2$^+$ p3 progenitors (FIGS. 9E,F), demonstrating that induced cells include all major known classes of spinal cord neuronal progenitors. Temporal qPCR analysis of rostrocaudal patterning gene expression revealed that these cells maintain a spinal cord phenotype and do not acquire a brain phenotype over serial passages (FIG. 1H).

To further confirm these results, the gene expression profile of human H9 ESC-derived spinal cord NSCs (H9-derived spinal cord NSCs) was examined two months after neural induction. When compared to expression profiles of human fetal brain and spinal cord, cultured H9-derived spinal cord NSCs expressed high levels of caudal HOX genes and low levels of the telencephalic markers FOXG1, SIX3, and OTX2 (FIG. 1I). Thus, the spinal cord NSCs expanded over time maintained their spinal cord positional identity. These long-term cultured cells could differentiate into functionally mature neurons (FIGS. 1J-L and FIG. 10K) and astrocytes (FIG. 10L) after spontaneous neuronal differentiation (see Example 7). Notably, differentiated neurons under retinoic acid- and SHH-free conditions expressed a diversity of neuronal markers (FIGS. 10M-P) and spinal cord neuronal subtype-specific transcription factors (FIGS. 10Q-X), including spinal interneurons and motor neurons (MNs). These results demonstrate that H9-derived spinal cord NSCs can be maintained over a long time period without losing their regional identity and capacity to generate spinal cord neurons.

Example 3. RNA-Sequencing of Spinal Cord Neural Stem Cells

To further examine the regional identity of H9-derived spinal cord NSCs along the rostrocaudal axis, their gene expression profiles were compared to human fetal central nervous system (CNS) tissues, fetal spinal cord-derived NPCs, and to "default" H9-NSCs that were induced by conventional methods that lead to a default brain identity (see Example 7) using RNA-Sequencing. HOX cluster (HOX A-D) expression was observed in H9-derived spinal cord NSCs, but not in default H9-NSCs (FIGS. 2A,B and FIGS. 11A,B). H9-derived spinal cord NSCs expressed cervical and thoracic spinal cord HOX genes, but not lumbar HOX genes, suggesting that the cells acquired a cervical-to-thoracic identity. Additionally, H9-derived spinal cord NSCs were clustered closely with human fetal spinal cord-derived NPCs, but separately from human fetal brain-derived NPCs and default H9-NSCs on hierarchical clustering analysis (FIG. 2C), indicating gene expression profiles of H9-derived spinal cord NSCs resemble human fetal spinal cord-derived NPCs, but are dissimilar to human fetal brain-derived NSCs. These results confirm that the spinal cord NSCs exhibit a spinal cord, but not brain, identity.

To assess the robustness of the differentiation protocol, it was repeated in another hESC line, UCSF4-ESCs, and in two human episomal induced pluripotent cell (iPSC) lines: RNA induced PSCs (RiPSCs) and IPS11 cells (see Example 7). hPSC-derived NSCs from these three additional cell lines acquired a spinal cord positional identity and maintained their regional identity and neurogenic potential over a long time period (>2 months; FIGS. 11C-K, 12A-S). The disclosed protocol is thus reproducible in multiple hPSC lines.

Example 4. Engraftment, Survival and Reciprocal Synapse Formation with Host

Figure 9A:
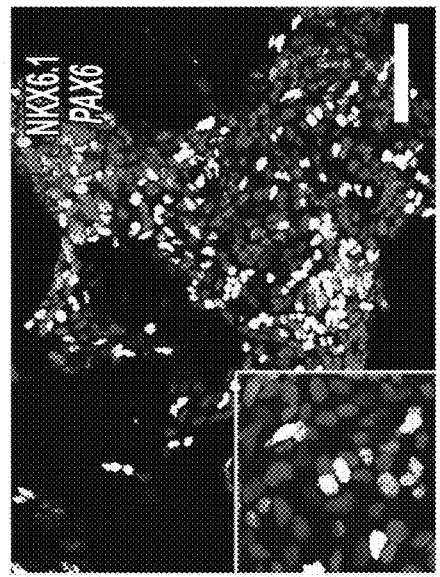

A major challenge to the field of NSC transplantation is the development of NSC types that are optimized to treat a specific disease indication. In the case of spinal cord injury (SCI), driving grafted cells to spinal cord identities has been a key limiting factor to advancement of transplantation therapies. To examine whether the disclosed human spinal cord NSCs exhibit properties in this context, they were grafted into models of rat SCI. Adult athymic rats underwent cervical level 4 (C4) lesions of the dorsal spinal cord, which interrupt corticospinal projections, the most important voluntary motor system in humans. H9-derived spinal cord NSCs expressing green fluorescent protein (GFP) were grafted into lesion sites two weeks following injury (see Spinal Cord Surgeries in Example 7). When examined up to three months post-transplantation, grafted cells survived and extended very large numbers of axons (labeled with NF70) into the injured host spinal cord (FIG. 3A). These human axons gave off branches that penetrated host gray matter (FIG. 3B). The majority of graft-derived cells expressed the neuronal markers βIII-tubulin (TUJ1), doublecortin (DCX), and NeuN by six weeks post-grafting (FIGS. 3C-D and FIG. 9A). Grafts also expressed the mature astrocyte marker glial fibrillary acidic protein (GFAP) six weeks post-grafting (FIG. 3E). In addition, cells of the early oligodendrocyte lineage (labeled for NG2) were detected by three months post-grafting (FIG. 3F). By six months post-grafting mature oligodendrocyte markers were present (labeled for adenomatous polyposis coli, APC) in the host white matter (FIG. 3G). Quantified three months post-grafting, 80.1±4.0% of cells expressed neuronal markers (FIG. 13B). These results indicate that H9-derived spinal cord NSCs can generate the three cardinal neural lineages (neuronal cells (neurons), astrocytes, and oligodendrocytes) in vivo.

The specific neuronal lineages adopted by H9-derived spinal cord NSCs were identified. H9-derived spinal cord NSCs generated a variety of spinal interneuronal subtypes (FIGS. 13C-T), including CHX10+ excitatory V2a interneurons (FIGS. 13J-T), a type of propriospinal neuron, three months post-graft. Six months post-grafting, cells also expressed calcium-calmodulin kinase 2 (CaMKII, for excitatory neurons, FIG. 3H), choline acetyltransferase (ChAT, for cholinergic motor neurons and premotor interneurons, FIG. 3I), GABA (for GABAergic inhibitory neurons, FIG. 3J), and GlyT2 (for glycinergic inhibitory neurons, FIG. 3K). These are all typical markers of mature spinal cord neurons. Grafts did not express 5-hydroxytryptamine (5-HT) or tyrosine hydroxylase (TH), indicating the absence of cells normally found at more rostral levels of the brainstem (serotonergic and dopaminergic neurons, respectively; data not shown). Interestingly, the disclosed spinal cord NSCs predominantly adopted excitatory neuronal fates (FIG. 3L), while brain NSCs predominantly adopted inhibitory GABAergic phenotypes. Graft-derived ChAT-expressing cells expressed the transcription factor FOXP1 much more than LHX3 (FIGS. 10U-W), suggesting that graft-derived motor neurons adopt the identity of lateral motor neuron columns which normally innervate the limbs, rather than medial motor neuron columns which normally innervate the axial (trunk) musculature. Six months post-engraftment, human spinal cord NSC grafts exhibited no evidence of overgrowth, and only 3.5±0.6% of graft cells expressed the proliferation cell marker Ki67 (Ki67$^+$/HuNu$^+$ cells), an amount similar to the proportions found in grafts of primary human fetal spinal cord-derived NPCs (unpublished data).

GFP-expressing human axons emerged from the lesion site in very large numbers and over very long distances (more than 10 spinal segments, a distance of 45 mm). Axons co-expressed human TAU, confirming their identity as axons, and grew in organized, linear rostro-caudal trajectories in the host dorsal column white matter (FIGS. 3M-O and FIGS. 8A-G). Throughout the course of their white matter projections, human axons gave off branches that penetrated host gray matter (FIG. 3B). Many human axons terminated throughout laminae IV-VII levels at all levels of the spinal cord for which human axons extended (FIG. 3P). GFP-labeled human axons formed bouton-like terminals in host rat gray matter, which co-localized with the human-specific presynaptic marker synaptophysin (SYN; FIG. 3O). These human axon terminals also closely associated with the dendrites of CaMKII-expressing host excitatory neurons (FIG. 14B) and ChAT-expressing motor neurons (FIG. 14C). These results suggest the existence of graft-host synaptic connectivity. Rat-specific vesicular glutamate transporter (VGLUT) 1/2 host excitatory terminals were observed at the host-graft border (FIGS. 14D and E, FIGS. 10B and 10C) and within the graft core (FIGS. 14F and 14G).

Figure 4J:
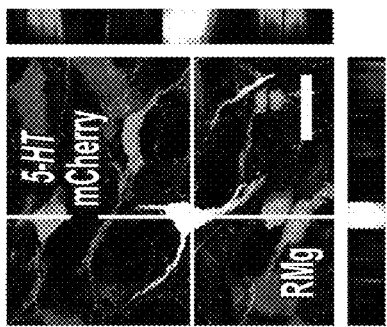
Figure 4K:
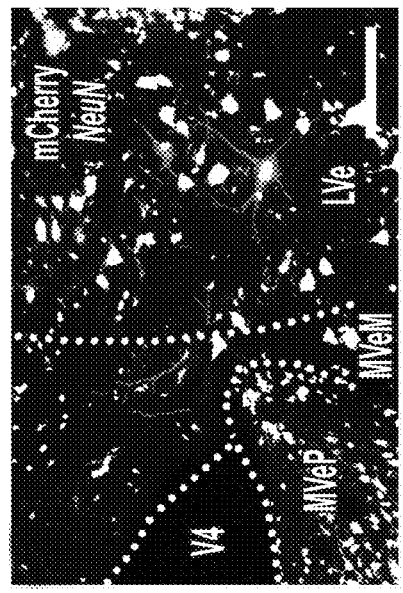
Figure 4L:
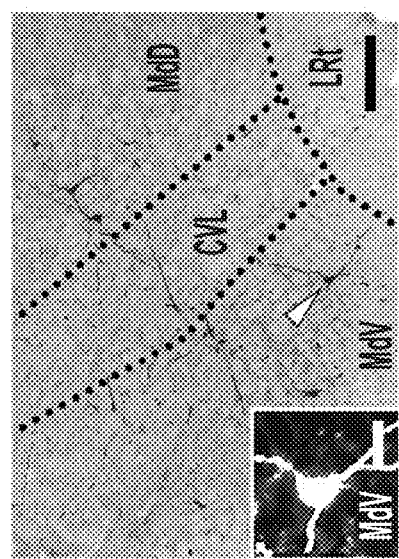
Figure 4M:
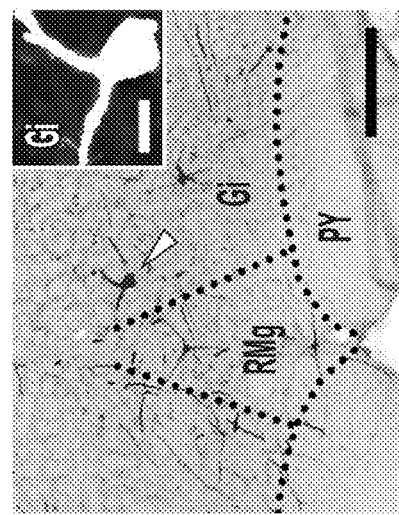

Example 5. Monosynaptic Rabies Virus Tracing Mapping of Host-to-Graft Connectivity To examine whether synapses were functional between host and the human neural graft, and the pattern of connectivity with host, mono-trans-synaptic rabies virus technology was utilized. A critical feature of this retrograde tracing system is exclusive transfer through functional synaptic connections, permitting unambiguous identification of interconnected neuronal circuitry. An H9-derived spinal cord NSC line was established that stably expressed: 1) GFP, 2) the TVA receptor, and 3) rabies glycoprotein. This vector allows for retrograde trans-synaptic spread of rabies expressing mCherry across one synapse following injection of glycoprotein deleted rabies virus (RVdG); moreover, rabies is exclusively transmitted by grafted human neural cells because only they possess the rabies TVA and glycoprotein to allow primary viral uptake and synaptic transport. This H9-derived spinal cord NSC line was grafted into sites of SCI two weeks after C4 spinal cord dorsal column lesions (n=4). Control animals were grafted with H9-derived spinal cord NSCs lacking the rabies glycoprotein and TVA (n=2). Animals received injections of RVdG into grafts four months post-transplantation, and were perfused a week later. In control animals, there were no mCherry$^+$ cells in the host spinal cord, brainstem, or brain (FIGS. 16A,B). In animals that received grafts expressing rabies glycoprotein and TVA receptor, trans-synaptically labeled host neurons were present throughout entire length of their spinal cords in all experimental animals (FIGS. 4A-G and FIGS. 16D and 16E). An absence of expression of the human nuclear-specific marker HuNu confirmed that these mCherry$^+$ cells were host neurons and not graft-derived neurons (FIG. 4D). These findings indicate that human spinal cord NSCs integrated into de novo intraspinal circuits. Among the phenotypes of host neurons that formed functional synapses with human neurons in the spinal cord were CHX10$^+$ V2b (FIG. 4I) and ChAT$^+$ V0c motor interneurons (FIG. 4J). In addition, sensory neurons of several classes were integrated into the graft circuitry, including TLX3$^+$ excitatory interneurons (FIG. 4K), BRN3A+DI1-3 interneurons (FIG. 4L), and LBX1$^+$ DI4-6 interneurons (FIG. 4M). In the lumbar spinal cord, mCherry$^+$/HuNu$^-$ cells were present in lamina VII, most likely representing long ascending propriospinal neurons (FIG. 4G), together with CMAF$^+$ sensory interneurons located in lamina IV (FIGS. 16D-F). Thus, in the spinal cord, H9-derived spinal cord NSCs integrates into both long-projecting and local spinal cord circuitries.

Figure 17C:
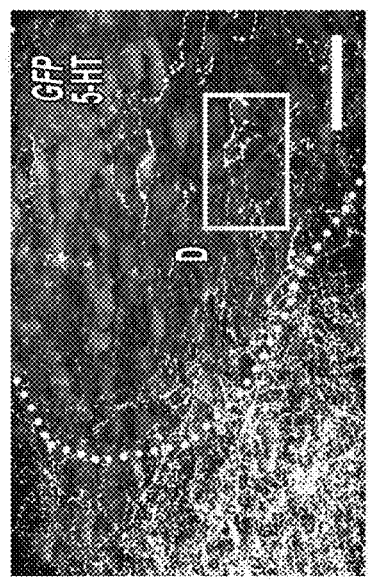
Figure 18A:
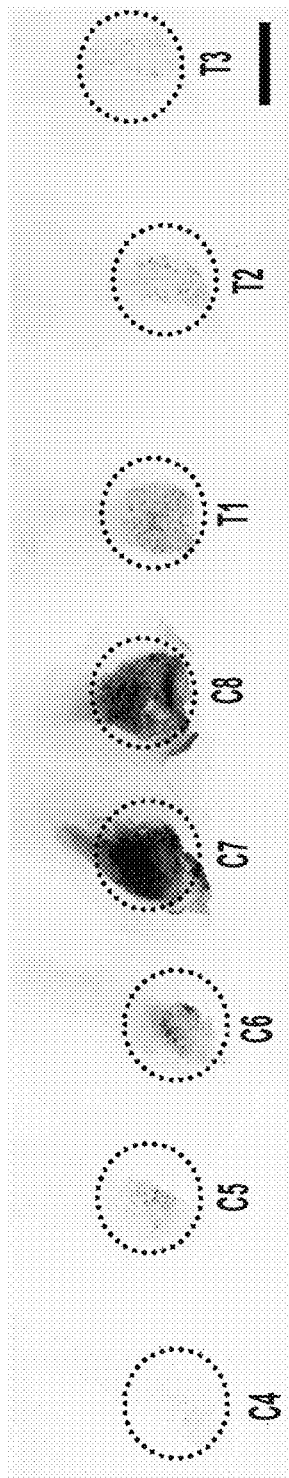
Figure 18B:
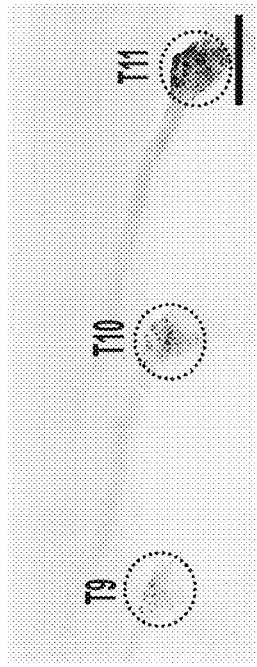
Figure 18F:
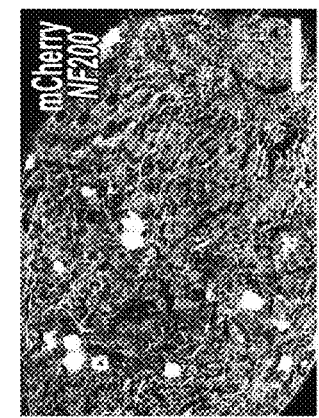
Figure 18E:
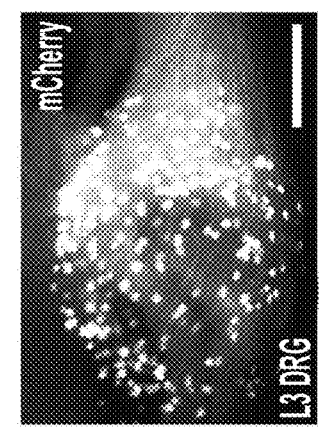
Figure 18D:
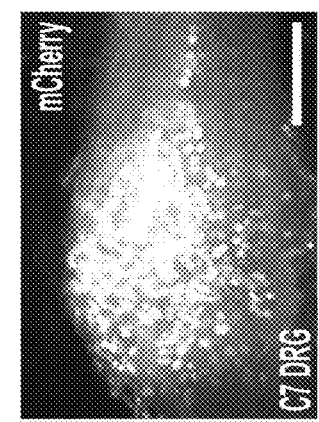
Figure 18C:

Graft connectivity was further assessed with host supraspinal (brain and brainstem) axonal systems. Of substantial importance was the observation that numerous mCherry-labeled neurons were observed in layer V of the motor cortex (FIG. 4H,I), indicating that host corticospinal motor axons regenerated into and connected with spinal cord NSC grafts. Because the corticospinal motor projection is the most important system for voluntary movement in humans, these findings are of substantial translational relevance. Diverse brainstem premotor populations were also mono-trans-synaptically labeled (FIGS. 4J-M, FIGS. 17A, B, including neurons in the red nucleus (RN; FIG. 17A), raphe magnocellular nucleus, and reticular nuclei (including ventral medullary reticular nucleus ventral part, MdV (FIG. 4L); gigantocellular reticular nucleus (Gi, FIG. 4K), and vestibular nucleus (FIG. 4M). Consistent with these results, 5-HT serotonergic fibers penetrated and connected grafts (FIGS. 17C-E). Several of these descending brainstem systems, including reticular and raphe projections, control and modify voluntary movement. We did not detect the presence of mCherry$^+$ cells in the cerebellum, consistent with the lack of monosynaptic projections from cerebellum to spinal cord. Primary sensory neurons in the dorsal root ganglia (DRG) also established connectivity with grafts (FIGS. 18A-E), consisting primarily of large diameter, NF200-expressing neurons (FIG. 18F). These results demonstrate graft derived neurons receive inputs from upstream motor control centers, local and distant spinal cord interneurons, and primary sensory neurons, providing strong support for their functional similarity to the endogenous spinal cord neurons.

Example 6. Robust Corticospinal Regeneration into PSC-Derived Spinal Cord Neural Stem Cells Corticospinal axons are of critical importance in controlling human voluntary movement, and spinal cord, but not forebrain, neural progenitor cells support robust corticospinal regeneration. To determine whether H9-ESCs driven to spinal cord identities support corticospinal regeneration, these cells were grafted to sites of SCI and compared their effects to H9-ESCs driven to rostral neuraxis identities. In the absence of the caudalizing morphogens CHIR and FGF2/8, H9-ESC-derived NSCs adopted a forebrain identity. Omission of only FGF2/8 resulted in NSCs of hindbrain identity. These results were confirmed by immunolabeling for the brain-specific marker OTX2 and the spinal cord-specific marker CDX2 (FIGS. 7K-R), and by qPCR utilizing probes detecting rostral and caudal neuraxis genes (FIGS. 5A and 7I). After confirmation that NSCs retained their respective regional identities over several passages (>15; FIG. 5B), they were grafted into immunodeficient rats with C4 dorsal column lesions (that remove >98% of corticospinal axons; n=6 spinal cord-NSC recipients; n=5 hindbrain-NSC recipients; and n=4 forebrain-NSC recipients). As above, grafts were placed two weeks after spinal cord lesions. Two months post-grafting, corticospinal axons were traced by injecting AAV8 expressing codon-optimized, membrane-targeted TdTomato (rCOMET) into bilateral motor cortices. Indeed, significant differences in the ability of corticospinal regeneration were observed in H9 grafts having different neuraxis level identities: host corticospinal axons extensively penetrated grafted H9-derived NSCs with spinal cord identities; fewer axons penetrated H9 NSCs with hindbrain identities; and corticospinal axons largely failed to penetrate H9 NSCs with forebrain identities (P<0.05, ANOVA with Bonferroni correction; FIGS. 5C-L). Host corticospinal axons regenerating into H9-derived spinal cord NSC grafts exhibited bouton-like terminals that co-localized with rat VGLUT1 (FIG. 5M and FIG. 20A) and synaptophysin (FIG. 20B), suggesting the presence of excitatory host synapses on human spinal cord NSC-derived neurons. In all graft types, ~80% of grafted cells expressed the neuronal marker Hu (FIGS. 20C-F), indicating that differences in the proportion of neurons among graft types did not account for the support of corticospinal regeneration. Since one of the characteristics of spinal cord NSC grafts is their capacity to support robust corticospinal regeneration, these results further validate the identity and utility of our H9-derived spinal cord NSCs.

Example 7. Methods

Pluripotent Cell Culture hES cells (WA-09 (H9) provided from WiCell Research Institute; passages 33-41, UCSF4 provided by Dr. Susan Fisher (UCSF); passages P13-P23) were cultured in mTeSR medium (Stem Cell Technologies) on MATRIGEL® (Corning Inc.)—coated plates. Cells were passaged using Versene (Thermo Fisher Scientific), washed and replated at a dilution of 1:10. Two human episomal IPSC lines were used in this study. IPS11 was purchased from ALSTEM and RIPSCs was provided from Allele Biotechnology. IPS11 (passages; 1*-10*) were cultured under the same conditions to hES cells. RiPSC line (passages 23-30) was cultured in E8 TeSR media (Stem Cell Technologies) on vitronectin (Stem Cell Technologies)—coated plates and passaged at a dilution of 1:6 using Gentle Cell Dissociation Reagent (Stem Cell Technologies).

Spinal Cord Neural Induction

For spinal cord stem cell induction, at about 70% confluence, mTeSR medium was changed to N2B27 medium (knockout Dulbecco's Modified Eagle's Medium (DMEM)/F12: Neurobasal (1:1), 1×N2, 1×B27, 1× penicillin/streptomycin, 1× Glutamax) supplemented with 100 nM LDN193189 (Stemgent), 10 µM SB431542 (Stemgent), 4 µM CHIR99021 (Stemgent), 1 µM DAPT (Stemgent), 100 ng/ml fibroblast growth factor (FGF) 2 (Peprotech, Rocky Hill, N.J.) and 100 ng/ml FGF8 (Peprotech). The medium was replaced the following day with fresh neural induction media every day and cells were split 1:3 with Accutase (Innovative Cell Technologies Inc.). 10 µM Y-27632 (ROCK inhibitor; Stemgent) was used to enhance cell survival. 10 days after neural induction, neural induction media was switched to neural maintenance media (N2B27 medium supplemented with 2 µM SB431542, 3 µM CHIR99021, and 200 nM Hh-Ag 1.5). At passage 4, plate coating was changed from MATRIGEL® or vitronectin to CELLSTART® (Thermo Fisher Scientific), changed again at passage 6 to poly-L-ornithine (PLO; Sigma-Aldrich)/laminin (LAM; Sigma-Aldrich). The change in coating will accelerate neural differentiation, as MATRIGEL® and vitronectin tend to retain the immature stage while CELLSTART® and PLO favor differentiation into NSC. Neuronal differentiation was performed in N2B27 medium supplemented with 300 ng/mL cAMP (Sigma-Aldrich) and 0.2 mM vitamin C (Sigma-Aldrich) from passage 10 to passage 15 spinal cord NSCs. While cAMP and vitamin C can accelerate neuronal differentiation, these agents are not required for differentiation to occur.

Human Fetal Derived Spinal Cord NSC and Default H9-NSC Culture

The human spinal cord NPC line UCSD1113 (Passages; 4-18) generated from a 9-week-old fetal spinal cord cultured on plates coated with CELLSTART, using N2B27 medium supplemented with 2% of STEMPRO Neural Supplement (all from Life Technologies), 20 ng/ml FGF2, 20 ng/ml epidermal growth factor (EGF), and 10 ng/ml leukemia inhibitory factor (LIF). Default H9-NSCs (Passages; 1*-8*) purchased from Life Technologies were cultured with 20 ng/ml FGF2 and 20 ng/ml EGF on PLO/LAM coated plates.

Induction and Maintenance of H9-Forebrain and Hindbrain NSCs

To induce H9-forebrain NSCs, mTeSR medium was changed to N2B27 medium supplemented with 100 nM LDN193189 and 10 µM SB431542. Neural induction media was changed every day and cells were split 1:3 with Accutase. Seven days after neural induction, induction media was switched to N2B27 medium supplemented with 20 ng/ml FGF 2, 20 ng/ml EGF, and 10 ng/ml LIF. At passage 4, plate coating was changed from MATRIGEL® to poly-D-lysine/laminin. To induce H9-forebrain NSCs, mTeSR medium was changed into N2B27 medium supplemented with LDN193189, 10 µM SB431542, 4 µM CHIR99021, and 1 µM DAPT. From 10 days after neural induction, cells were cultured with exactly the same condition to H9-spinal cord NSCs.

Immunocytochemistry

Cultures were fixed for 30 minutes in 4% paraformaldehyde (PFA) in 0.1M PB at room temperature and post-fixed in methanol for 15 minutes. After being washed three times with Tris-buffered saline (TBS), fixed samples were permeabilized with 0.25% Triton X-100 with 5% normal horse serum in TBS for 1 h. Primary antibodies in the blocking solution were applied overnight. The primary antibodies used for immunolabeling are listed in FIG. 22. After rinsing, samples were incubated with donkey Alexa Fluor secondary antibodies (1:500, Invitrogen) for 1 h at room temperature. Nuclear counterstaining was performed using 4',6-diamidino-2-phenylindole (DAPI).

Quantitative Reverse Transcription-Polymerase Chain Reaction (RT-PCR)

Total RNA was isolated from cultures using the RNeasy Mini kit (Qiagen) following the manufacturer's protocol. Human fetal brain and spinal Cord Poly $A^+$ RNA (Clontech Laboratories, Inc.) were used for control. Total RNA was quantified with NanoDrop® (Thermo-Fischer). For cDNA synthesis, the reverse transcription reaction was performed using the PrimeScript™ RT Master Mix (Perfect Real Time, Clontech) and quantitative PCR was performed using primers specific for the genes of interest (see FIG. 23) and SYBR® Premix Ex Taq™ II (Tli RNase H Plus, Clontech) in 20 µL reactions. Data were normalized to glyceraldehyde-3-phosphate dehydrogenase (GAPDH) expression.

Electrophysiology

H9-derived spinal cord NSCs were cultured on glass coverslips coated with POL/LAM and infected with lentivirus expressing GCaMP5 under control of the MAP2 promoter (generous gift from Russell C. Addis, UPenn). Cells on coverslips transferred into a recording chamber. Recordings were made in a submersion-type recording chamber and perfused with oxygenated ACSF containing (in mM) 119 NaCl, 2.5 KCl, 2 $MgCl_2$, 2.5 $CaCl_2$, 1.3 $NaH_2PO_4$, 26.0 $NaHCO_3$, 20 glucose (~295 mOsml) at 23° C. at a rate of 2-3 ml/minute. Whole-cell patch clamp recordings were obtained using Multiclamp 700B patch amplifiers (Molecular Devices) and data was analyzed using pClamp 10 software (Molecular Devices). Data were low-pass filtered at 2 kHz, and digitized at 10 kHz. Whole-cell voltage and current clamp recordings were made at room temperature using pulled patch pipettes (5-6 MO) filled with internal solution containing (150 mM K-gluconate, 1.5 mM $MgCl_2$, 5.0 mM HEPES, 1 mM EGTA, 10 mM phosphocreatine, 2.0 mM ATP, and 0.3 mM GTP).

RNA-Sequencing

Total RNA was collected using the RNeasy Mini kit and stored at −70° until needed. Total RNA integrity was examined using the Agilent Bioanalyzer 2000. TrueSeq stranded mRNA-seq libraries were prepared from 5 µg of total RNA (Illumina mRNA-seq kit, RS-122-2103) and sequenced using Illumina HiSeq 2500 PE-100 (sequences publically available from GEO, accession number: GSE83107). TrueSeq stranded mRNA-seq libraries were prepared and sequenced using Illumina HiSeq 2500 at the IGM Genomics Center, University of California, San Diego. Unsupervised hierarchical clustering was performed in Cluster 3.0. Samples were clustered using uncentered Pearson correlation and average linkage. RNA-Seq data was downloaded from GEO, accession number GSM1944034 (fetal brain-derived NPCs) and GSM1381228-1381231 (default H9 NSCs) for unsupervised hierarchical clustering.

Animals

A total of 32 athymic nude rats were subjects of this study (150-180 g, The Jackson Laboratory). NIH guidelines for laboratory animal care and safety were strictly followed. Animals had free access to food and water throughout the study. All surgery was done under deep anesthesia using a combination (2 ml/kg) of ketamine (25 mg/ml), xylazine (1.3 g/ml), and acepromazine (0.25 mg/ml).

Spinal Cord Surgeries

Rat C4 dorsal column lesions were made using a tungsten wire knife to transect all of dorsal column axons as described previously (Kadoya, K., et al. Spinal cord reconstitution with homologous neural grafts enables robust corticospinal regeneration. *Nat Med* (2016)). Briefly, the tungsten wire knife was inserted 1 mm from the dorsal surface of spinal cord and raised to transect the corticospinal tract, leaving a fragment of the most dorsal aspect of the ascending dorsal column sensory axons intact to create a closed lesion cavity with intact dura. Two weeks after C4 corticospinal lesions, a 2 μl suspension of $10^6$ NSCs (viability >90%) were injected into the lesion site using a four growth factor cocktail consisting of 50 μg/ml BDNF (Peprotech), 10 μg/ml FGF2, 10 μg/ml VEGF (Peprotech), and 50 μM MDL28170. The following groups and subject numbers were studied.

To investigate survival, differentiation, and growth, GFP-expressing H9-spinal cord NSCs were injected into the lesion site (n=11), followed by perfusion 6 weeks (n=3), 3 months (n=4), and 6 months (n=4) later.

To assess graft-host connectivity, GFP-expressing H9-spinal cord NSCs were injected into the lesion site (experimental group, n=5; control group, n=2) and animals were perfused 4 months later.

To examine corticospinal regeneration into H9 derived graft, H9-forebrain NSCs (n=4), H9-hindbrain NSCs (n=5), or H9-spinal cord NSCs (n=6) were injected into the lesion site, followed by perfusion two months later.

Anterograde tracing of corticospinal axons, AAV8 vectors were used that expressed codon-optimized, membrane-targeted TdTomato (rCOMET, Salk Viral Vector Core Facility, La Jolla, Calif.). Briefly, AAV8-rCOMET were injected into both motor cortices using a pulled glass micropipette with injection pressure and duration controlled by a PicoSpritzer II (General Valve). AAV8-rCOMET ($5 \times 10^{13}$ genome copies/ml) was injected into 8 sites per hemisphere at a volume of 0.5 μl per site over a total period of 30-45 minutes.

Rabies Virus Mapping of Synaptic Connectivity

For the generation of NSCs expressing EnvA-pseudo-typed rabies helper proteins, H9 NSCs previously transduced with lentivirus expressing CAG-GFP were transduced with a polycistronic lentivirus expressing TVA, SAD-B19 rabies G-protein, and GFP, under control of the CAG promoter (Salk Viral Vector Core Facility). After several passages (at least 3) and caudalization, H9-derived GFP+ NSCs expressing CAG-TVA-G-protein were grafted into lesion sites After 4-5 months of graft maturation, grafts were stereotactically injected with a total of 2.5 μL EnvA pseudo-typed G-deleted (SADΔG) rabies expressing mCherry ($1E^7$ vg/mL in PBS) into the graft core and along the graft/host interface evenly across 15 sites, with three injection depths at each site (1, 0.7, and 0.5 mm), using pulled glass micropipettes and a PicoSpritzer, as guided by visualization of the graft with a GFP-excitation flashlight. Rats were perfused 7 days later.

Histology and Immunohistochemistry

Animals were perfused with 4% paraformaldehyde in 0.1 M phosphate buffer (pH 7.2). Spinal cord were removed, post-fixed and sectioned on a vibratome set at 30 μm intervals. Sections were incubated with primary antibodies overnight (see FIG. 21) then incubated in Alexa 488, 594, or 647 conjugated donkey secondary antibodies (1:500, Invitrogen) for 1 hr at room temperature. For nuclear staining, DAPI was added to the final wash. Images were captured using an Olympus AX-70 fluorescence microscope (Olympus) equipped with an Optronics Microfire A/R digital camera Microfire A/R, (Optronics), a confocal microscope (FV-1000, Olympus), or the BZ-9000 digital microscope system (Keyence).

Quantification of Corticospinal Axons or Cell Types in Grafts.

For the quantification of neural differentiation in human cell grafts, Hu, human GFAP, NG2, CaMKII, ChAT, GABA, GlyT2, FOXG1, or LHX3 and NuNu were used. By using microscopy, cells were sampled in images (100× or 200× magnification) from randomly selected regions of grafts. The proportion of neural or neuronal marker expressing cells to total number of HuNu was then calculated and averaged among groups. The number of corticospinal axons regenerating into grafts in lesion sites was quantified using images taken by BZ-9000 digital microscope system as previously described (Kadoya, K., et al. Spinal cord reconstitution with homologous neural grafts enables robust corticospinal regeneration. *Nat Med* (2016)). Briefly, 1-in-6 sections were labeled for rCOMET-traced corticospinal axons. Dorsal-to-ventral virtual lines were placed and then examined under 400× magnification. RCOMET-labeled axons that intersected the line were marked and counted. Two sagittal sections containing the corticospinal main track were quantified. In all cases, observers were blinded to group identity.

Statistical Analysis

Multiple group comparisons were made using one-way analysis of variance (ANOVA; JMP software) at a designated significance level of 95%. Non-parametric data were assessed using Mann-Whitney. Data are presented as mean±SEM. As stated above, all quantifications were performed by observers blinded to group identity.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Reference to a Sequence Listing Submitted Via EFS-Web

The content of the ASCII text file of the sequence listing named "1959169-00048 Sequence Listing_ST25.txt" which is 15 KB in size was created on Oct. 3, 2019 and electronically submitted via EFS-Web is incorporated by reference in its entirety.

---

What is claimed is:

1. A method of generating spinal cord neural stem cells comprising, culturing human pluripotent stem cells in a stem cell-appropriate medium supplemented with:
   (a) one or more SMAD inhibitors, wherein the SMAD inhibitors are inhibitors of:
      (i) bone morphogenetic protein (BMP), and
      (ii) activin and transforming growth factor β (TGF-β); and
   (b) one or more caudalizing morphogens, wherein the caudalizing morphogens comprise:
      (i) fibroblast growth factor 2 and fibroblast growth factor 8 (FGF2/8); and
      (ii) an activator of WNT signaling;
   wherein the neural stem cells produced maintain spinal cord positional identity.

2. The method of claim 1, wherein the medium is supplemented with dual SMAD inhibitors.

3. The method of claim 1, wherein the activator of WNT signaling comprises CHIR99021.

4. The method of claim 1, wherein the BMP inhibitor comprises LDN-193189.

5. The method of claim 1, wherein the inhibitor of activin and TGF-β comprises SB-431542.

6. The method of claim 1, wherein the human pluripotent stem cells are human embryonic stem cells.

7. The method of claim 1, wherein the human pluripotent stem cells are human induced pluripotent stem cells.

8. The method of claim 1, wherein the stem cell-appropriate medium is supplemented with LDN-193189, SB-431542, fibroblast growth factor 2 and fibroblast growth factor 8 (FGF2/8), and CHIR99021.

* * * * *